United States Patent [19]

Bang et al.

[11] Patent Number: 5,244,806
[45] Date of Patent: Sep. 14, 1993

[54] DNA ENCODING NOVEL TISSUE PLASMINOGEN ACTIVATOR DERIVATIVES HAVING KRINGLES 1 AND 2 DELETED, VECTORS AND HOST CELLS

[75] Inventors: Nils U. Bang; Sheila P. Little, both of Indianapolis; Brigitte E. Schoner, Zionsville; Barbara J. Weigel, Indianapolis, all of Ind.

[73] Assignee: Eli Lilly and Company, Indianapolis, Ind.

[21] Appl. No.: 614,966

[22] Filed: Nov. 19, 1990

Related U.S. Application Data

[63] Continuation of Ser. No. 348,155, May 2, 1989, abandoned, which is a continuation of Ser. No. 889,041, Jul. 24, 1986, abandoned, which is a continuation-in-part of Ser. No. 769,298, Aug. 26, 1985, abandoned.

[51] Int. Cl.$^5$ .................. C12N 9/64; C12N 9/48; C12N 5/00; C12N 15/00
[52] U.S. Cl. .................. 435/252.33; 435/226; 435/240.2; 435/320.1; 536/23.2; 536/23.4; 536/23.5
[58] Field of Search ............... 435/219, 212, 226, 320, 435/69.1, 172.3, 240.2, 252.33; 536/27, 23.2, 23.4, 23.5; 935/4, 10, 14, 29, 32, 70, 72

[56] References Cited

U.S. PATENT DOCUMENTS

| | | | |
|---|---|---|---|
| 4,766,075 | 8/1988 | Goeddel et al. | 435/172.3 |
| 4,935,237 | 6/1990 | Higgins et al. | 424/94.64 |
| 4,959,314 | 9/1990 | Mark | 435/69.1 |
| 5,106,741 | 4/1992 | Marotti et al. | 435/226 |

FOREIGN PATENT DOCUMENTS

| | | |
|---|---|---|
| 093619 | 11/1983 | European Pat. Off. |
| 174835 | 3/1986 | European Pat. Off. |
| 84/01786 | 5/1984 | World Int. Prop. O. |
| 86/01538 | 3/1986 | World Int. Prop. O. |

OTHER PUBLICATIONS

Pennica, D. et al., *Nature*, 301:214–220.
ATTC Catalogue of Bacteria, Phages and rDNA Vectors, Sixteenth edition, 1985, p. 244.
Jesty, J. et al., *J. Biol. Chem.*, 249(2):509–515, 1974.
Aldrich Chemical Company Catalog, 1990, p. 53 and 121.
Chemical Abstracts Displays for Registry Numbers 1670-14-0 and 2498-50-2 from STN commercial database.
van Zonneveld et al., *J. Cellular Biochemistry*, vol. 32, pp. 169–178, 1986.
Ny et al., 1984, Proc. Natl. Acad. Sci. USA 81:5355–5359.
Bányai et al., 1983, FEBS Letter 163(1):37–41.
Peterson et al., 1983, Proc. Natl. Acad. Sci USA 80:137–141.
Juhan-Vague et al., 1984, Thromb. Res. 33:523–530.
Collen, D., 1980, Thromb. Haemost. 43:77–89.
van Zonneveld et al., Jul. 15, 1985, 10th International Congress for the Society of Thrombosis and Haemostosis, Fibrinolysis I. Molecular Biology, Abstract 22, p. 4.
Gething, M. et al., 1986, Abstracts 15th Annual Meetings, UCLA Winter Symposia on Molec. and Cell. Biol., J. Cell Biochem., Supplement 10A, Jan. 20–Feb. 15, 1986.
Bang, N. U., et al., 1985, Blood 66(5):330a, No. 1205.

*Primary Examiner*—Robert J. Hill, Jr.
*Assistant Examiner*—Marianne Porta Allen
*Attorney, Agent, or Firm*—Thomas G. Plant; Leroy Whitaker

[57] ABSTRACT

The invention discloses modified forms of the enzyme tissue plasminogen activator (t-PA) in which recombinant DNA techniques are utilized to modify the structure of the t-PA cDNA to express a modified t-PA which retains the ability to activate plasminogen yet binds less efficiently to plasmin inhibitor. The invention provides novel DNA compounds and recombinant DNA expression vectors that encode modified human t-PA wherein all or a portion of the kringle protein domains of native human t-PA are removed. Both eukaryotic and prokaryotic expression vectors containing the modified t-PA DNA have been constructed and used to transform Chinese hamster ovary cells and *Escherichia coli* cells.

30 Claims, 32 Drawing Sheets

DNA ENCODING NOVEL TISSUE PLASMINOGEN ACTIVATOR DERIVATIVES HAVING KRINGLES 1 AND 2 DELETED, VECTORS AND HOST CELLS

CROSS-REFERENCE

This application is a continuation of application Ser. No. 07/348,155, filed on May 2, 1989 now abandoned, which is a continuation of U.S. application Ser. No. 06/889,041, filed on Jul. 24, 1986, abandoned, which is a continuation-in-part of U.S. application Ser. No. 06/769,298 filed on Aug. 26, 1985, abandoned.

BACKGROUND

In recent years tissue plasminogen activator (t-PA) has emerged as an interesting therapeutic alternative to conventional thrombolytic agents, streptokinase (SK) and urokinase (UK). The major physiological plasminogen activator, t-PA, in contrast to UK and SK, activates fluid phase circulating plasminogen inefficiently but activates fibrin-associated plasminogen very efficiently. The relative advantage of t-PA over SK and UK is best explained in the context of a brief outline of the current knowledge of the fibrinolytic enzyme system provided in the following.

FIG. 1 is a simplified scheme of the fibrinolytic enzyme system consisting of plasminogen activators, one or more plasminogen activator inhibitors (PA), the proenzyme plasminogen, the active serine protease plasmin and plasmin inhibitors. The physiological plasminogen activators t-PA and UK synthesized in and secreted by endothelial cells are inhibited by one, perhaps two, newly discovered fast acting inhibitors. One of these proteins has been purified to homogeneity and characterized in several laboratories. This plasminogen activator inhibitor is found in plasma at varying concentrations and found in platelets at high concentrations and released during platelet activation as the thrombotic process evolves. It is found in sharply increased concentrations during the third trimester of pregnancy, in patients with thromboembolism, and in patients with conditions predisposing to thromboembolic disease. Thus, different patients with different levels of plasminogen activator inhibitor may respond differently to infused t-PA or UK. All plasminogen activators act on plasminogen producing plasmin which is a nonspecific trypsin-like protease which proteolytically degrades, in addition to fibrin, several plasma clotting factors. Plasmin is counterbalanced by a major inhibitor, alpha-two plasmin inhibitor and to a lesser degree by alpha-two macroglobulin. FIG. 1 depicts the fundamental differences between the commercially available thrombolytic agents SK and UK and t-PA. SK and UK activate plasminogen adsorbed to the thrombus as well as plasma plasminogen, and the activation of plasma plasminogen results in temporary hyperplasminemia and a profound coagulation defect. The coagulation defect arises because plasmin proteolytically degrades and destroys clotting factors V and VIII as well as fibrinogen. The degradation products of fibrinogen add to the coagulation defect since these fibrinogen fragments possess potent anti-coagulant properties. In contrast, t-PA is relatively fibrin-specific. When administered at moderate doses, it activates only thrombus plasminogen and not plasma plasminogen to any significant extent. However, when given rapidly at high doses, t-PA may cause temporary systemic hyperplasminemia and a mild to moderately severe fibrinolytic coagulation defect. Intravenously administered t-PA has been shown effective in dissolving experimental venous and arterial clots in animals. In a recent preliminary report from a large prospective controlled clinical trial, t-PA administered intravenously was shown to be effective in establishing reperfusion of occluded coronary arteries in patients with acute myocardial infarction.

SUMMARY OF THE INVENTION

This invention relates to certain modified forms of the enzyme tissue plasminogen activator in which recombinant DNA techniques are utilized to modify the structure of the t-PA cDNA to express a modified t-PA (mt-PA). Some of these modified molecules exhibit functional properties superior to those of the native protein. The present invention provides novel DNA compounds and recombinant DNA expression vectors that encode a modified human tissue plasminogen activator wherein all or a portion of the "kringle" protein domains of native human t-PA are removed. The vectors promote expression of the novel DNA compounds in either eukaryotic or prokaryotic host cells. The present invention also provides host cells transformed with these novel cloning vectors. The present DNA compounds can be used to produce t-PA derivatives never before synthesized in the laboratory, or not known to exist in nature, and the present invention also comprises these unique proteins.

The modified t-PA molecules of the present invention were constructed with two goals in mind. The molecule should retain the unique fibrin-binding properties of native t-PA and possess a functional advantage over the native molecule. In this regard, some of the proteins were created such that they interacted more slowly and inefficiently with plasminogen activator inhibitor(s) as compared to the native molecule. In addition, the modified form of t-PA should be expressed in significant quantities in a prokaryotic host.

The complete predicted secondary structure and the suggested folding of t-PA is depicted in FIG. 2. The folding arrangement is deduced from sequence homologies with other proteins. The amino-terminal portion of the peptide chain contains a disulfide linked loop referred to as a "finger", highly homologous to the "finger" structure in fibronectin known to endow this protein with fibrin-binding properties. A second domain from the amino-terminus is homologous to the epidermal growth factor (EGF). Similar growth factor domains occur in other serine proteases including UK, clotting factors IX and X and protein C. A third domain in t-PA contains two complexly folded, highly disulfide-linked structures referred to as "kringles". Similar homologous kringle structures have been demonstrated in high molecular weight UK, plasminogen and prothrombin. The fourth or carboxy-terminal domain of t-PA is the serine protease portion, in the two chain form of the molecule constituting the so-called B chain. The t-PA B chain is homologous to similar domains in UK, plasma serine clotting proteases and trypsin.

To achieve the aforementioned goals, five postulates were considered. First, the finger domain of the molecule should be preserved based on the hypothesis that the finger structure is essential for fibrin binding. Preliminary evidence supporting this hypothesis came from a report from Banyai et al., 1983, *FEBS Letters* 163:37. These authors demonstrated that the t-PA finger was homologous to fingers in the fibrin binding domain of fibronectin. They also provided preliminary evidence that limited plasmin proteolysis of t-PA resulting in the release of a peptide roughly the size of the finger and EGF domains produced a t-PA variant which no longer adsorbed to fibrin. However, neither the identity of the peptide nor the exact plasmin cleavage site(s) were established. The present invention discloses the successful expression of a cDNA clone in *E. coli* encoding amino acids 1–96 of the native sequence and encompassing the finger plus the EGF domains (see example 3). The 1–96 peptide was purified and used in competitive t-PA binding studies. The results of these studies demonstrate that inhibition of native t-PA binding to fibrin by the finger-EGF peptide results in progressively increasing inhibition of plasminogen activation with increasing quantities of the peptide in the activation mixture. Thus, the finger domain is firmly established as possessing fibrin binding properties.

Secondly, the deletion of both or one of the two kringle domains should lead to an improved t-PA. According to prevalent theory voiced in many publications, including the Genentech EPO 93619 patent application, the kringle domain region in t-PA is essential for fibrin binding and the preferential activation of plasminogen associated with fibrin. In contrast, we postulate that the predominant function of the kringles in the t-PA molecule is binding of the enzyme to its newly described fast-acting inhibitor. Evidence in support of this hypothesis lies in the analogy with plasmin-alpha-two plasmin inhibitor interaction. Kinetic studies summarized in Castellino, F., 1981, *Chemical Reviews* 81:421 have shown that the reaction between plasmin and alpha-two plasmin inhibitor proceeds in two steps; an extremely fast, reversible second order reaction followed by a slower, irreversible first order reaction. The rate constant for the first step, one of the fastest so far described for protein-protein interactions at $3.8 \times 10^7$ $M^{-1}s^{-1}$ is at least one order of magnitude higher than the reaction rate between trypsin and its inhibitors. Evidence has been presented that the first two (most amino terminal) of the five kringles in plasmin are essential for binding plasmin to alpha-two plasmin inhibitor during the first of the two steps in the reaction. When three of the five kringles in plasmin are enzymatically removed with elastase treatment, the dissociation constant for the first step is dramatically changed from $10^{-10}$ by approximately two to three orders of magnitude to $10^{-7}$. The kringles in plasminogen and plasmin are also known to bind to fibrinogen and fibrin but the interaction is very weak with a dissociation constant in the high millimolar range. FIG. 3 is a schematic illustration of the plasmin alpha-two plasmin inhibitor reaction. Plasmin kringles one and probably two envisioned during step one, bind to the plasmin inhibitor (PI), thereby bringing in closer proximity the active serine which irreversibly interacts with another domain in alpha-two PI through the cleavage of a Leu-Met peptide bond and the formation of a protease enzyme-acyl inhibitor complex in analogy with trypsin, antitrypsin and thrombin antithrombin complexes. It is our postulate that the major function of the two kringles in t-PA is the binding of t-PA to its inhibitor. Inherent in this hypothesis is the prediction that removal of one or both of the kringle domains from t-PA would substantially slow the reaction rate between the enzyme and its inhibitor without completely abolishing an interaction since the second phase of the reaction involving the active serine in t-PA in the formation of the enzyme-acyl inhibitor complex, will not be affected. Based on our findings of the strong fibrin binding properties of the finger domain in t-PA, we further postulate that the two kringles in t-PA have only a minor, if any, role in t-PA fibrin binding.

Our third postulate is that any t-PA mutant should contain the entire serine protease portion of the molecule responsible for cleaving the one peptide bond which results in the conversion of plasminogen into plasmin.

Following the hypothesis originally presented by Walter Gilbert (see Gilbert, 1978, *Nature* 271:501), that the exons of eukaryotic genes code for functional domains, our fourth postulate assumes that a preferred t-PA variant should contain only domains encoded by discrete exons of the gene, i.e. that any new cDNA construct should conform with the natural exon-intron junctions of the gene. However, it is important to note that alternative forms of a modified t-PA gene may include additional amino acid residues from either exon of the respective kringle domains without increasing the reaction rate between the enzyme and its inhibitor.

Our fifth postulate is that any t-PA mutant will be functionally active whether it is glycosylated or not. This assumption is based on work in our laboratory (Little et al., 1984, *Biochemistry* 23:6191). In this investigation we produced highly purified t-PA almost free of carbohydrate either through enzymatic treatment with endoglycosidase H of highly purified t-PA or through tunicamycin treatment of Bowes melanoma cells in culture, a cell line which synthesizes and secretes human t-PA at high levels. The deglycosylated t-PA was found to activate plasminogen in the presence of fibrin very efficiently and to activate plasminogen in the absence of fibrin very inefficiently at rates identical with those observed for the intact fully glycosylated molecule. Indeed, it would appear from a recent PCT publication, WO84/01786, that the chemical removal of carbohydrate side chains in t-PA endows this protein with a significantly prolonged biological half-life when compared to intact, fully glycosylated t-PA.

On the basis of these five postulates we describe in the following examples the cloning and expression in prokaryotic and eukaryotic cells of a t-PA mutant containing the finger, EGF, and serine protease domains but lacking either the first or both of the kringle domains. The fibrin-dependent functional properties of this new protein as well as its decreased ability to interact with plasminogen activator inhibitors is also presented in detail.

For purposes of the present invention, as disclosed and claimed herein, the following terms are as defined below.

ApR—the ampicillin-resistant phenotype or gene conferring same.

Exon—a portion of a gene that is transcribed and appears in the final mRNA transcript that codes for a protein.

Intron—a portion of a gene that is transcribed but does not appear in the final mRNA transcript.

Kringle—a characteristic triple disulphide structure.

KnR—the kanamycin-resistant phenotype or gene conferring same.

Poly A Addition Site—a DNA sequence encoding a polyadenylation signal.

Promoter—a DNA sequence that directs transcription of DNA into RNA.

Protein Domain—a structurally discrete unit of a protein molecule.

Recombinant DNA Cloning Vector—any autonomously replicating agent, including, but not limited to, plasmids and phages, comprising a DNA molecule to which one or more additional DNA segments can be or have been added.

Recombinant DNA Expression Vector—any recombinant DNA cloning vector into which a promoter has been incorporated.

Restriction Fragment—any linear DNA sequence generated by the action of one or more restriction enzymes.

Sensitive Host Cell—a host cell that cannot grow without a DNA segment encoding a selectable resistance characteristic.

Structural Gene—any DNA sequence that encodes the amino acids comprising a functional polypeptide, inclusive of translational start and stop signals.

TetR—the tetracycline-resistance phenotype or gene conferring same.

Transformation—the introduction of DNA into a recipient host cell that changes the genotype of the recipient cell.

Translational Activating Sequence—any DNA sequence, inclusive of that encoding a ribosome binding site and translational start codon, that provides for the translation of a mRNA transcript into a peptide or polypeptide.

Translational Stop Signal—any DNA triplet that codes for a translational stop codon.

The following amino acids are abbreviated as follows:
ALA is Alanine,
ARG is Arginine,
ASN is Asparagine,
ASP is Aspartic acid,
CYS is Cysteine,
GLN is Glutamine,
GLU is Glutamic acid,
GLY is Glycine,
HIS is Histidine,
ILE is Isoleucine,
LEU is Leucine,
LYS is Lysine,
MET is Methionine,
PHE is Phenylalanine,
PRO is Proline,
SER is Serine,
THR is Threonine,
TRP is Tryptophan,
TYR is Tyrosine, and
VAL is Valine.

DETAILED DESCRIPTION OF THE INVENTION

Figure 1:
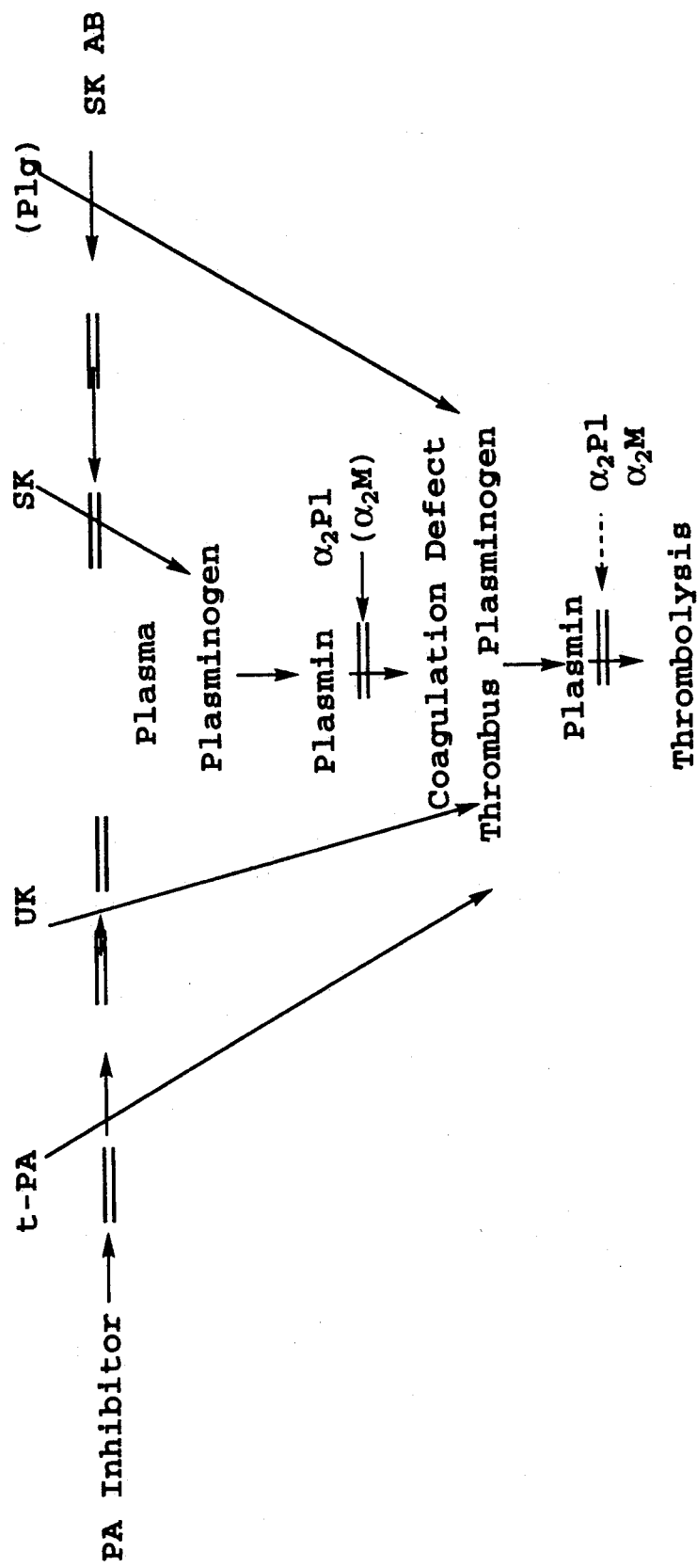
FIG. 1 is a schematic illustration of the fibrinolytic enzyme system.
Figure 2:
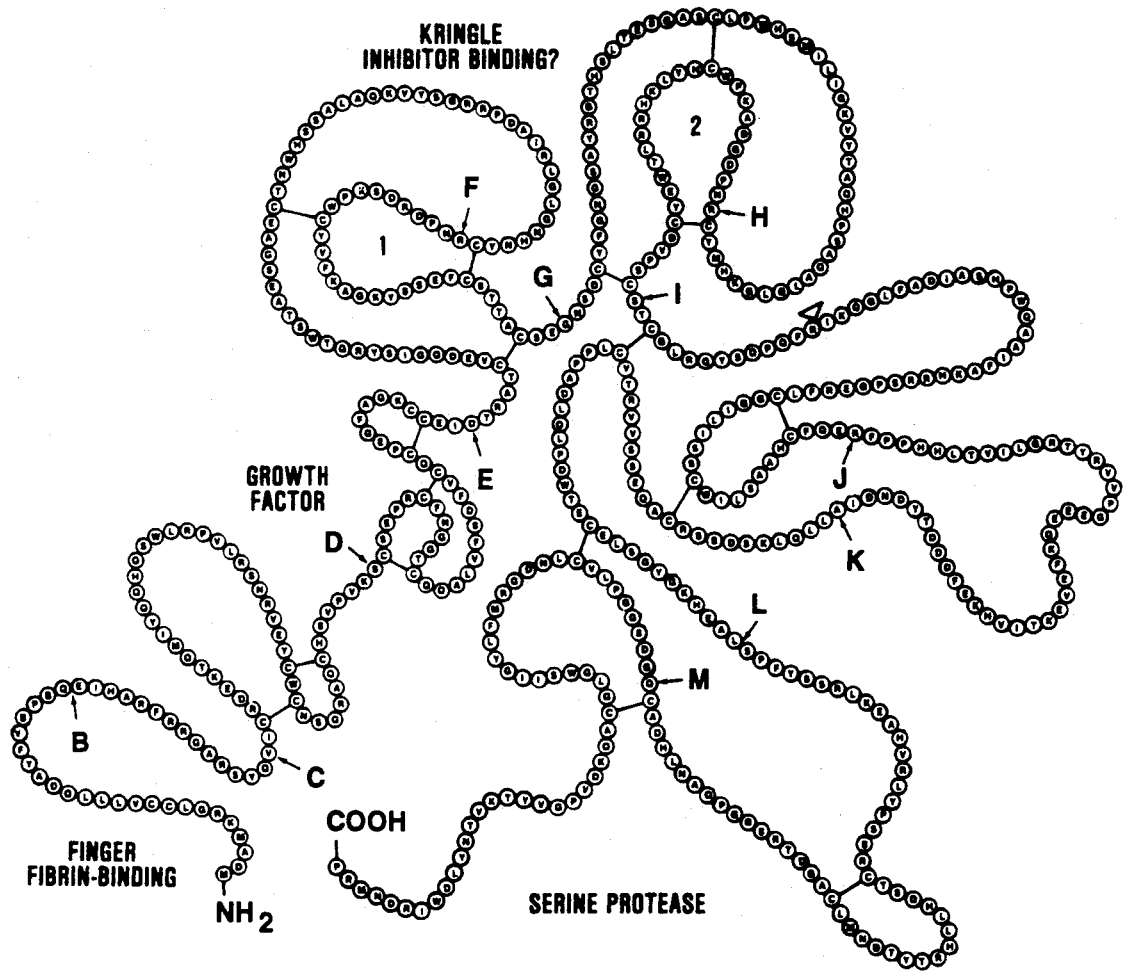
FIG. 2 shows a diagram of the predicted secondary structure of t-PA. The inverted triangle represents the cleavage site that separates the light chain from the heavy chain.
Figure 3:
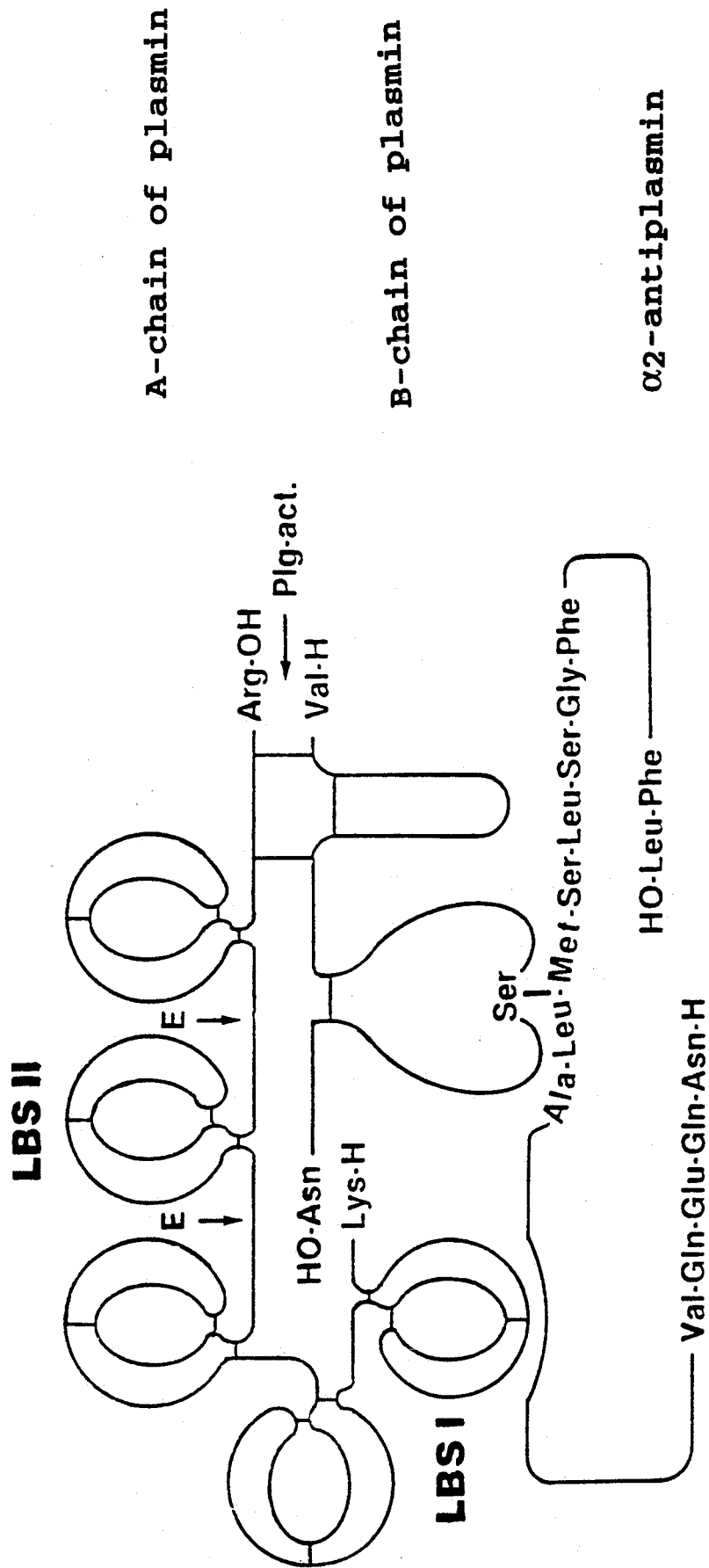
FIG. 3 shows a diagram of the plasmin alpha-two plasmin inhibitor reaction.

The present invention comprises novel DNA compounds encoding a modified human tissue plasminogen activator. Depicting only the coding strand of the molecule for convenience, two of the novel compounds comprise the sequence:

```
          10          20          30
5'-R—TCT TAC CAA GTG ATC TGC AGA GAT GAA AAA ACG CAG
 40          50          60          70
ATG ATA TAC CAG CAA CAT CAG TCA TGG CTG CGC CCT
        80          90          100
GTG CTC AGA AGC AAC CGG GTG GAA TAT TGC TGG TGC
110         120         130         140
AAC AGT GGC AGG GCA CAG TGC CAC TCA GTG CCT GTC
    150         160         170         180
AAA AGT TGC AGC GAG CCA AGG TGT TTC AAC GGG GGC
          190         200         210
ACC TGC CAG CAG GCC CTG TAC TTC TCA GAT TTC GTG
 220         230         240         250
TGC CAG TGC CCC GAA GGA TTT GCT GGG AAG TXC TGT
       260         270         280
GAA ATA TCC ACC TGC GGC CTG AGA CAG TAC AGC CAG
290         300         310         320
CCT CAG TTT CGC ATC AAA GGA GGG CTC TTC GCC GAC
    330         340         350         360
ATC GCC TCC CAC CCC TGG CAG GCT GCC ATC TTT GCC
          370         380         390
AAG CAC AGG AGG TCG CCC GGA GAG CGG TTC CTG TGC
 400         410         420         430
GGG GGC ATA CTC ATC AGC TCC TGC TGG ATT CTC TCT
       440         450         460
GCC GCC CAC TGC TTC CAG GAG AGG TTT CCG CCC CAC
470         480         490         500
CAC CTG ACG GTG ATC TTG GGC AGA ACA TAC CGG GTG
    510         520         530         540
GTC CCT GGC GAG GAG GAG CAG AAA TTT GAA GTC GAA
          550         560         570
AAA TAC ATT GTC CAT AAG GAA TTC GAT GAT GAC ACT
 580         590         600         610
TAC GAC AAT GAC ATT GCG CTG CTG CAG CTG AAA TCG
       620         630         640
GAT TCG TCC CGC TGT GCC CAG GAG AGC AGC GTG GTC
650         660         670         680
CGC ACT GTG TGC CTT CCC CCG GCG GAC CTG CAG CTG
    690         700         710         720
CCG GAC TGG ACG GAG TGT GAG CTC TCC GGC TAC GGC
          730         740         750
AAG CAT GAG GCC TTG TCT CCT TTC TAT TCG GAG CGG
 760         770         780         790
CTG AAG GAG GCT CAT GTC AGA CTG TAC CCA TCC AGC
       800         810         820
CGC TGC ACA TCA CAA CAT TTA CTT AAC AGA ACA GTC
830         840         850         860
ACC GAC AAC ATG CTG TGT GCT GGA GAC ACT CGG AGC
    870         880         890         900
GGC GGG CCC CAG GCA AAC TTG CAC GAC GCC TGC CAG
          910         920         930
GGC GAT TCG GGA GGC CCC CTG GTG TGT CTG AAC GAT
 940         950         960         970
GGC CGC ATG ACT TTG GTG GGC ATC ATC AGC TGG GGC
```

-continued 980 990 1000
CTG GGC TGT GGA CAG AAG GAT GTC CCG GGT GTG TAC 1010 1020 1030 1040
ACC AAG GTT ACC AAC TAC CTA GAC TGG ATT CGT GAC

1050
AAC ATG CGA CCG TGA-3' wherein
A is deoxyadenyl,
G is deoxyguanyl,
C is deoxycytidyl,
T is thymidyl,
R is

5'-ATG GAT GCA ATG AAG AGA GGG CTC TGC TGT

-continued
GTG CTG CTG CTG TGT GGA GCA GTC TTC GTT
TCG CCC AGC CAG GAA ATC CAT GCC CGA TTC
AGA AGA GGA GCC AGA-3' or 5'-ATG GGA-3' or, and $\phi$
$X_{248}$ is G or C.

The amino acid sequence, numbered to facilitate further discussion of the present mt-PA is:

$H_2N$—R—SER TYR GLN VAL ILE CYS ARG ASP GLU LYS THR GLN MET ILE
5 10

TYR GLN GLN HIS GLN SER TRP LEU ARG PRO VAL LEU ARG SER
15 20 25

ASN ARG VAL GLU TYR CYS TRP CYS ASN SER GLY ARG ALA GLN
30 35 40

CYS HIS SER VAL PRO VAL LYS SER CYS SER GLU PRO ARG CYS
45 50 55

PHE ASN GLY GLY THR CYS GLN GLN ALA LEU TYR PHE SER ASP
60 65 70

PHE VAL CYS GLN CYS PRO GLU GLY PHE ALA GLY LYS Z CYS
75 80

GLU ILE SER THR CYS GLY LEU ARG GLN TYR SER GLN PRO GLN
85 90 95

PHE ARG ILE LYS GLY GLY LEU PHE ALA ASP ILE ALA SER HIS
100 105 110

PRO TRP GLN ALA ALA ILE PHE ALA LYS HIS ARG ARG SER PRO
115 120 125

GLY GLU ARG PHE LEU CYS GLY GLY ILE LEU ILE SER SER CYS
130 135 140

TRP ILE LEU SER ALA ALA HIS CYS PHE GLN GLU ARG PHE PRO
145 150

PRO HIS HIS LEU THR VAL ILE LEU GLY ARG THR TYR ARG VAL
155 160 165

VAL PRO GLY GLU GLU GLU GLN LYS PHE GLU VAL GLU LYS TYR
170 175 180

ILE VAL HIS LYS GLU PHE ASP ASP ASP THR TYR ASP ASN ASP
185 190 195

ILE ALA LEU LEU GLN LEU LYS SER ASP SER SER ARG CYS ALA
200 205 210

GLN GLU SER SER VAL VAL ARG THR VAL CYS LEU PRO PRO ALA
215 220

ASP LEU GLN LEU PRO ASP TRP THR GLU CYS GLU LEU SER GLY
225 230 235

TYR GLY LYS HIS GLU ALA LEU SER PRO PHE TYR SER GLU ARG
240 245 250

LEU LYS GLU ALA HIS VAL ARG LEU TYR PRO SER SER ARG CYS
255 260 265

THR SER GLN HIS LEU LEU ASN ARG THR VAL THR ASP ASN MET
270 275 280

```
       LEU CYS ALA GLY ASP THR ARG SER GLY GLY PRO GLN ALA ASN
                       285                 290

LEU HIS ASP ALA CYS GLN GLY ASP SER GLY GLY PRO LEU VAL
       295             300                 305

CYS LEU ASN ASP GLY ARG MET THR LEU VAL GLY ILE ILE SER
       310                 315                 320

TRP GLY LEU GLY CYS GLY GLN LYS ASP VAL PRO GLY VAL TYR
                   325             330                 335

THR LYS VAL THR ASN TYR LEU ASP TRP ILE ARG ASP ASN MET
                       340             345                 350

ARG PRO—COOH
``` wherein
R is

```
                              -30
H2N—MET ASP ALA MET LYS ARG GLY LEU

-25
CYS CYS VAL LEU LEU LEU LYS GLY ALA

-15                   -10
VAL PHE VAL SER PRO SER GLN GLU ILE

-5
HIS ALA ARG PHE ARG ARG GLY ALA ARG—COOH
``` or H₂N-MET GLY - COOH, or φ,
Z₈₃ is CYS or SER, and
H₂N— is the amino-terminus, and
—COOH is the carboxy-terminus.

The t-PA molecule used to construct the modified t-PA molecules of the present invention was derived from cDNA clones prepared from Bowes human melanoma cells. Polyadenylated messenger RNA was isolated from Bowes human melanoma cells and fractionated on agarose gels. Aliquots of mRNA were injected into *Xenopus laevis* oocytes for translation and assayed for t-PA activity.

The enriched fraction(s) of mRNA were used as a template for cDNA synthesis. Libraries of cDNA were screened with specific oligonucleotides to identify t-PA specific sequences. Because the complete t-PA sequence was not isolated in this library, another specific oligonucleotide was used to prime and extend the copying of the 5' end of the t-PA mRNA. The cDNA clones were manipulated to construct a DNA molecule comprising both the coding sequence of t-PA and also portions of the DNA complementary to the untranslated mRNA at the 5' and 3' ends of the coding region. After the 5' clone was isolated, the complete cDNA was assembled and sequenced. Thus, the complete cDNA molecule comprises both the coding sequence above, and, again depicting only one strand of the molecule, also contains this additional sequence:

```
5'-ATG GAT GCA ATG AAG AGA GGG CTC TGC TGT

GTG CTG CTG CTG TGT GGA GCA GTC TTC GTT

TCG CCC AGC CAG GAA ATC CAT GCC CGA TTC

AGA AGA GGA GCC AGA-3'
``` wherein
A is deoxyadenyl,
G is deoxyguanyl,
C is deoxycytidyl, and
T is thymidyl
at the 5' end of the coding strand of the t-PA coding sequence. Due to the complementary nature of DNA base-pairing, the sequence of one strand of a double-stranded DNA molecule is sufficient to determine the sequence of the opposing strand.

Figure 4:
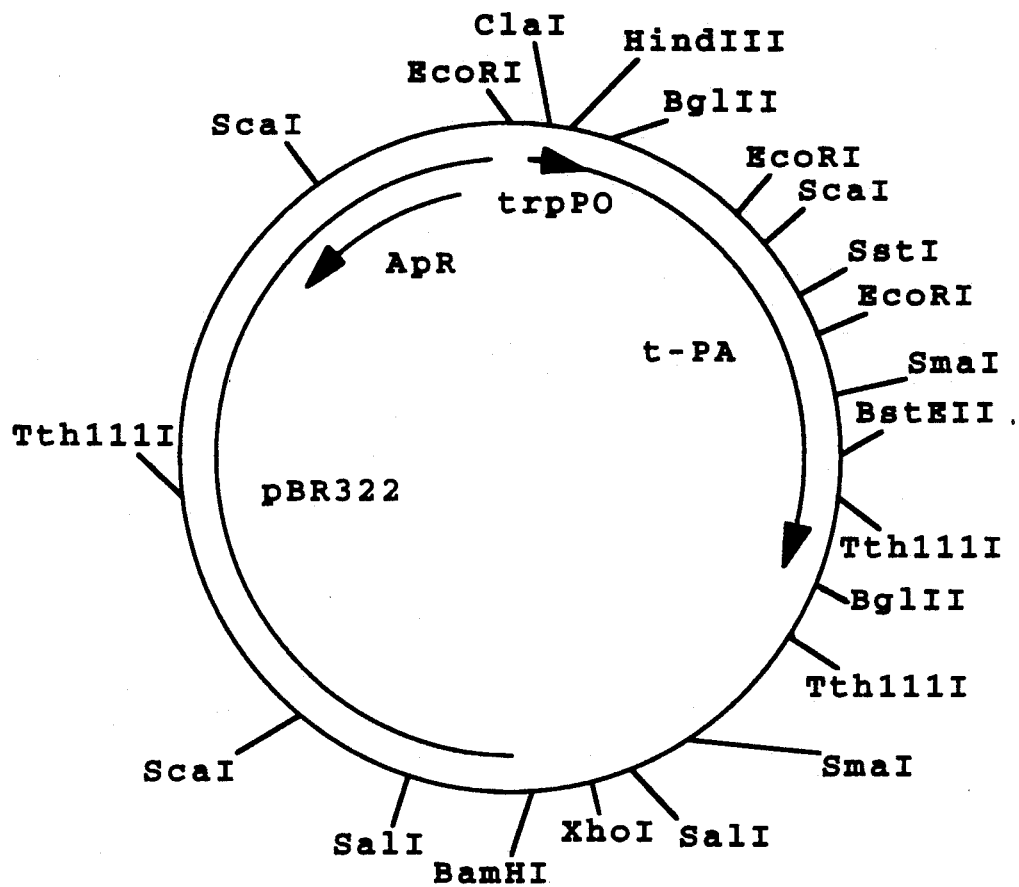
FIG. 4 is a restriction site and function map of plasmid pTPA102.

This cDNA molecule was inserted into plasmid pRC. The intermediate plasmid pRC was constructed by inserting a 288 bp EcoRI-ClaI fragment containing the tryptophan promoter and operator (trpPO) sequence into similarly digested plasmid pKC7. Plasmid pKC7 is a derivative of pBR322 that carries a determinant for kanamycin and ampicillin resistance (Rao and Rogers, 1979, *Gene* 7:79). The trpPO fragment is described in Goeddel et al., 1990, *Nuc. Acid Res.* 8:4057. The region of the cDNA clone, bounded by HindIII and BglII restriction sites, was inserted in plasmid pRC. The resulting plasmid, designated pTPA102, can be conventionally isolated from *E. coli* K12 MM294/pTPA102, a strain deposited with and made part of the permanent stock culture collection of the Northern Regional Research Laboratory (NRRL), Peoria, Illinois. A culture of *E. coli* K12 MM294/pTPA102 can be obtained from the NRRL under the accession number B-15834. A restriction site and function map of plasmid pTPA102 is presented in FIG. 4 of the accompanying drawings.

Figure 5:
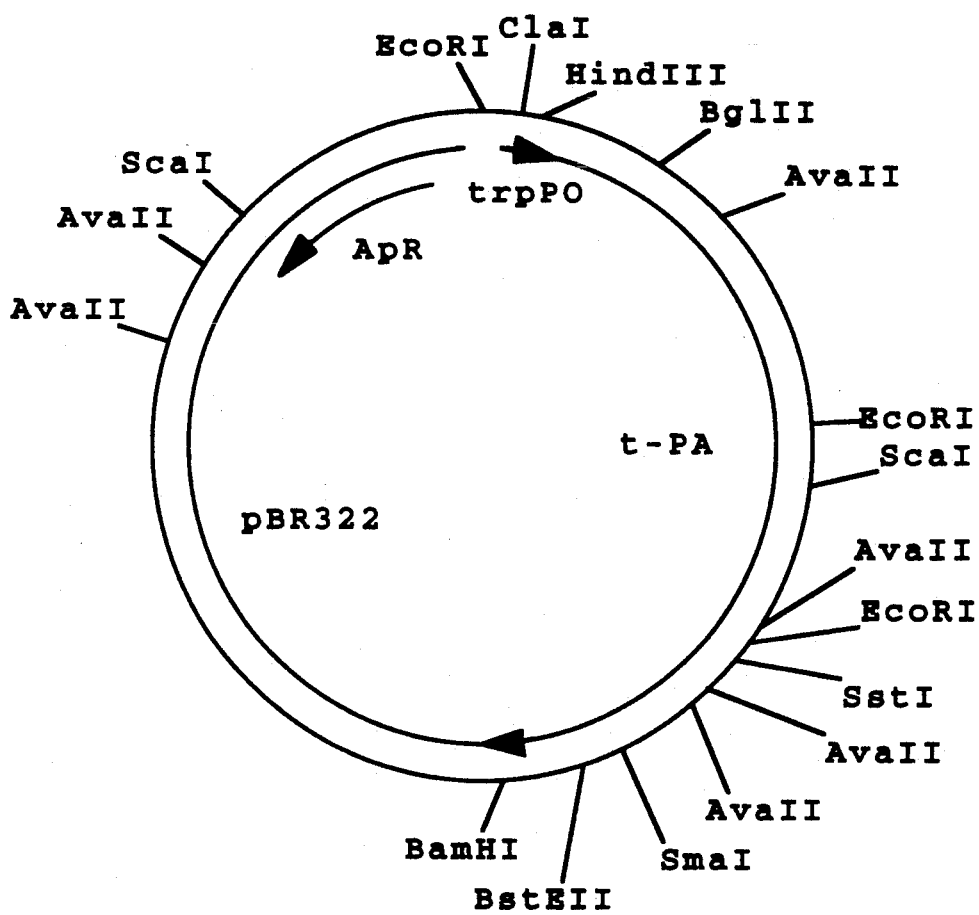
FIG. 5 is a restriction site and function map of plasmid pTPA103.

The derivation of plasmid pTPA103 from plasmid pTPA102 is described at length in Example 2A. Briefly, plasmid pTPA102 was digested with TthIII.1 restriction enzyme and the fragments were gel-purified. Next, the desired fragment was filled in with Klenow and BamHI linkers were ligated to the fragment. After ligation, the mixture was digested with BamHI and EcoRI restriction enzymes and the portion containing the t-PA gene was subcloned. The resulting plasmid, designated pTPA103, was further modified as disclosed in Example 2C. These modifications introduced the sequence, 5'-ATG-GGA-3'; thus, the ATG codon forms a translational activating sequence for the prokaryotic expression vectors disclosed herein. A restriction site and function map of plasmid pTPA103 is presented in FIG. 5 of the accompanying drawings.

Figure 6:
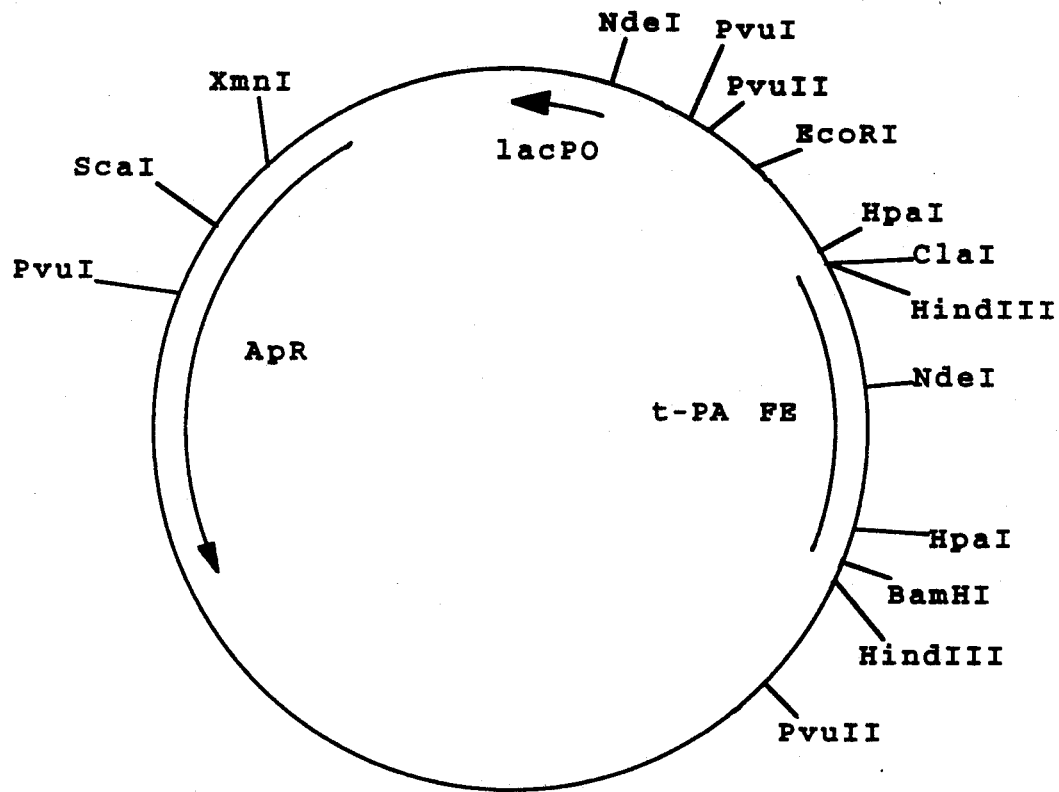
FIG. 6 is a restriction site and function map of plasmid pUC19 TPA FE.

Through a variety of manipulations, described in Examples 2 and 3, plasmid pUC19 TPA FE was derived from plasmid pTPA103. Basically, this construction was accomplished by isolating a EcoRI-AvaII restriction fragment from plasmid pTPA103 wherein the AvaII site was subsequently changed to a HpaI site. This EcoRI-HpaI fragment containing, inter alia, the amino-terminus of the TPA gene, was ligated into SmaI-and EcoRI-digested plasmid pUC19 (commercially available from Pharmacia, Inc., 800 Centennial Dr., Piscataway, N.J. 08854) to yield plasmid pUC19 TPA FE. The amino acid sequence of the t-PA protein has been renumbered in plasmid pUC19 TPA FE to be compatible with the two additional amino acid residues Met and Gly upstream from the amino acid residue Ser. A restriction site and function map is presented in FIG. 6 of the accompanying drawings.

Plasmid pUC19 TPA FE was partially digested with HpaI then completely digested with BamHI restriction enzyme and the large HpaI-BamHI fragment, containing 98 amino acid residues, was ligated to an ~1 kb ScaI-BamHI fragment of plasmid pTPA103. The fusion of this HpaI site to the ScaI site removed 482 base-pairs (bp) from the kringle domains of the now altered t-PA gene sequence. The resulting vector, pBW25, contains both the amino- and carboxy-terminal regions of the native t-PA gene excluding a substantial portion of the kringle domains.

To facilitate the effort to construct a kringle-less form of t-PA, the E. coli phage M13 was used. The M13 phage (commercially available from New England Biolabs, 32 Tozer Road, Beverly, Mass. 01915, designated MP8) contains part of the E. coli lac operon. An additional 33 base pair fragment that contains multiple unique restriction sites has been inserted into the amino terminus of the lacZ gene. An ~810 bp t-PA coding region of plasmid pBW25, spanning the carboxy terminus portion of the growth factor domain through the deleted kringle domains and into the amino terminus portion of the serine protease domain, was inserted on an EcoRI-HindIII fragment into this multiple restriction site region to yield pM8BW26. Site specific mutagenesis was carried out to further delete ~50 bp from the functional kringle domain; to this single stranded phage was hybridized a 36-mer (GGGAAGTGCTGTGA AATATC-CACCTGCGGCCTGAGA). In addition, a M13 primer was used to facilitate complete second strand synthesis. In total, 525 bp were removed from the coding sequence of t-PA. A representative phage pM8BW27 (Replicative form - RF) was isolated, sequenced and found to exhibit the predicted deletion. A new junction was thus constructed between isoleucine, amino acid residue 86 and serine, formerly amino acid residue 262 of the native molecule. This partial t-PA sequence was realigned with the native amino terminus and carboxy terminus t-PA gene sequence in plasmid pBW28.

Plasmid pBW28 was formed during a multiple ligation reaction involving four restriction fragments from four different sources. Specifically, an ~50 bp XbaI-NdeI chemically synthesized cistron linker; an ~563 bp NdeI-EcoRI fragment from RF pM8BW27 containing the amino terminus of the mt-PA gene; an ~687 bp EcoRI-BamHI fragment from plasmid pTPA103 containing the carboxy terminus of the mt-PA gene; and, an ~5.8 kb BamHI-XbaI vector segment from plasmid pL110 were ligated together and the resulting ligation mixture was used to transform E. coli. The construction of plasmid pL110 is presented in detail in Examples 19–29. A restriction site and function map of plasmid pL110 and all intermediates used in the construction of pL110 are presented in FIGS. 16–28 of the accompanying drawings. A preferred form of the present invention comprising the novel mt-PA DNA sequence, including the 5'-ATG-GGA-3' sequence can be isolated on an ~1.2 kb NdeI-BamHI. fragment from plasmid pBW28.

Figure 8:
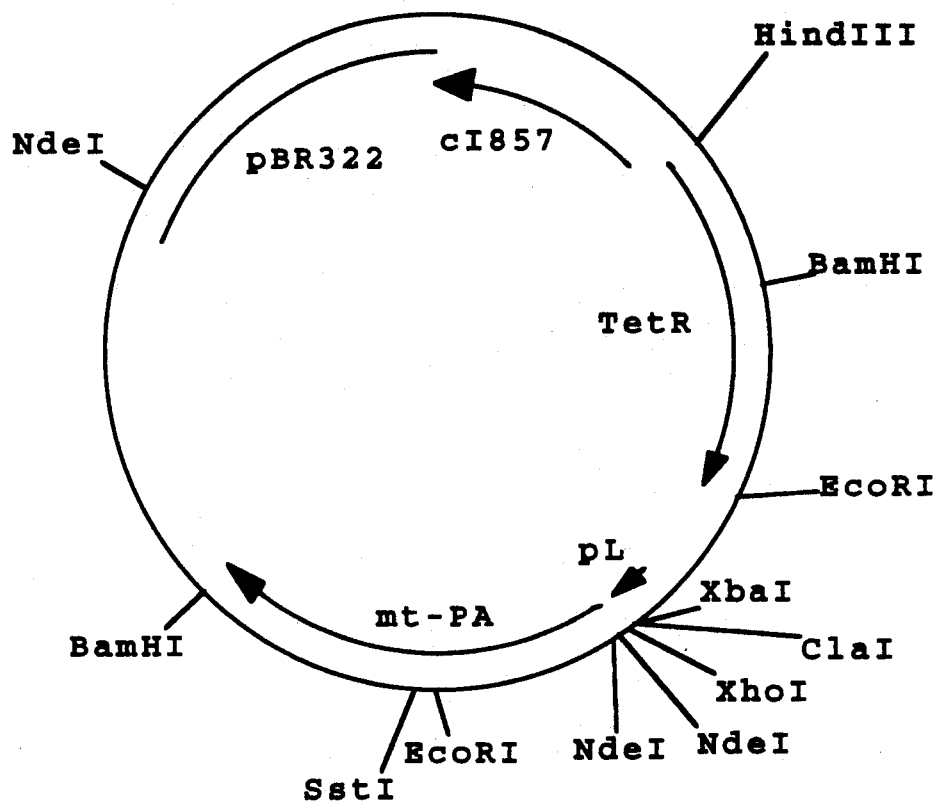
FIG. 8 is a restriction site and function map of plasmid pBW28.

The mt-PA DNA sequence present in pBW28 has been designated mt-PA2. A restriction site and function map of plasmid pBW28 is presented in FIG. 8 of the accompanying drawings.

Therefore, in a preferred embodiment of the present invention, the two kringle domains of t-PA were selectively removed at the proposed intron-exon junctions of native, human t-PA. In addition, because the junction for the first kringle domain fell within the triplet coding for aspartic acid, residue 87 was also deleted. The removal of residue 87 demonstrates that the deletion of a functional domain need not occur at precise exon/intron boundaries. One skilled in the art will realize, for purposes of the present invention, that the boundaries of protein domains are not required to be absolute in order to achieve expression of functional modified genes.

In another preferred embodiment of the present invention, the DNA encoding mt-PA2 was subjected to site specific mutagenesis to substitute a serine residue in the growth factor domain for an existing cysteine. This particular gene derivative was constructed using a synthetic oligonucleotide wherein the $CYS_{83}$ (TGC) codon was changed to a $SER_{83}$ (TCC) codon. This change was made to eliminate a potentially free sulfhydryl residue, which may facilitate the recovery of active enzyme from E. coli. The resulting mt-PA designated mt-PA3, was first transferred to a bacterial plasmid for expression in E. coli, and then to a pSV2-type vector for expression in a mammalian host.

The invention is not limited to the particular modified forms of t-PA disclosed in the following examples. Any modification of the kringle domain region which results in the removal of either kringle domain or only portions of these domains falls within the scope of the present invention. The removal of a portion of the kringle domains from the t-PA molecule, for example, at the adjacent cross-linking disulphide bridges (amino acid residues 92 through 261) will form a modified t-PA which retains the fibrin-directed properties of the native molecule. Preferred embodiments of the present invention are directed to a modification in the kringle domains wherein the binding of the plasminogen activator inhibitor to the modified t-PA is effectively reduced.

In yet another embodiment of the present invention, a modified gene. for t-PA was constructed wherein amino acid residues 87 through 175, spanning the first kringle domain of native t-PA, were selectively removed using site specific mutagenesis on a portion of the native t-PA gene. Thus, the resulting gene, designated mt-PA4, contains the $SER_{83}$ substitution and is devoid of the first kringle. The DNA coding for mt-PA4 was transferred first to a bacterial plasmid for expression in E. coli and then to a pSV2-type vector for expression in a mammalian host.

As stated above, a variety of recombinant DNA expression vectors comprising the modified t-PA-encoding DNA have been constructed. The present vectors are of two types: those designed to transform eukaryotic, especially mammalian, host cells; and those designed to transform E. coli. The present DNA compounds which encode modified t-PA are especially preferred for the construction of vectors for transformation of, and expression of mt-PA activity in, mammalian and other eukaryotic host cells.

The serine residue of the structural gene coding for native t-PA is preceded by 35 amino acids, the amino-terminal 20-23 of which probably constitute a hydrophobic signal peptide involved in the secretion of t-PA.

The remaining 12-15 hydrophilic amino acids immediately preceding the start of mature t-PA ma constitute a 'pro' sequence similar to that found for numerous mammalian proteins. These 35 residues are encoded in the eukaryotic expression vector pBW32. However, as the present mt-PA DNA compounds are readily modified to delete that portion encoding the signal and pro peptide sequences of t-PA, the present invention is not limited to the use of this particular eukaryotic signal peptide for expression of t-PA in eukaryotic host cells.

Many mammalian host cells possess the necessary cellular machinery for the recognition and proper processing of the signal peptide present on the amino-terminus of the protein encoded by plasmid pBW32. Some mammalian host cells also provide the post-translational modifications, such as glycosylation, as is observed in human t-PA present in blood plasma. A wide variety of vectors exist for the transformation of eukaryotic host cells, and the specific vector exemplified below is in no way intended to limit the scope of the present invention.

The pSV2-type vector used in the present invention comprises segments of the SV40 genome that constitute a defined eukaryotic transcription unit—promoter, intervening sequence, and polyadenylation (poly A) site. In the absence of SV40 t-antigen, the plasmid pSV2-type vector transforms mammalian and other eukaryotic host cells by integrating into the host cell chromosomal DNA. A variety of plasmid pSV2-type vectors are known in the literature (see *Eukaryotic Viral Vectors*, 1982, edited by Gluzman, published by Cold Spring Harbor Laboratories, Cold Spring Harbor, N.Y.), such as plasmids pSV2-gpt, pSV2-neo, pSV2-dhfr, and pSV2-$\beta$-globin, in which the SV40 early promoter drives transcription of an inserted gene. These vectors are available either from the American Type Culture Collection (ATCC) in Rockville, Md. or from the Northern Regional Research Laboratory (NRRL) in Peoria, Ill.

Plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification, described in a review article by Schimke, 1984, Cell 37:705, can involve DNA sequences closely contiguous with the dhfr gene. Plasmid pBW32 is a vector of the present invention comprising both the dhfr gene and also the mt-PA structural gene under the control of the SV40 early promoter.

Figure 9:
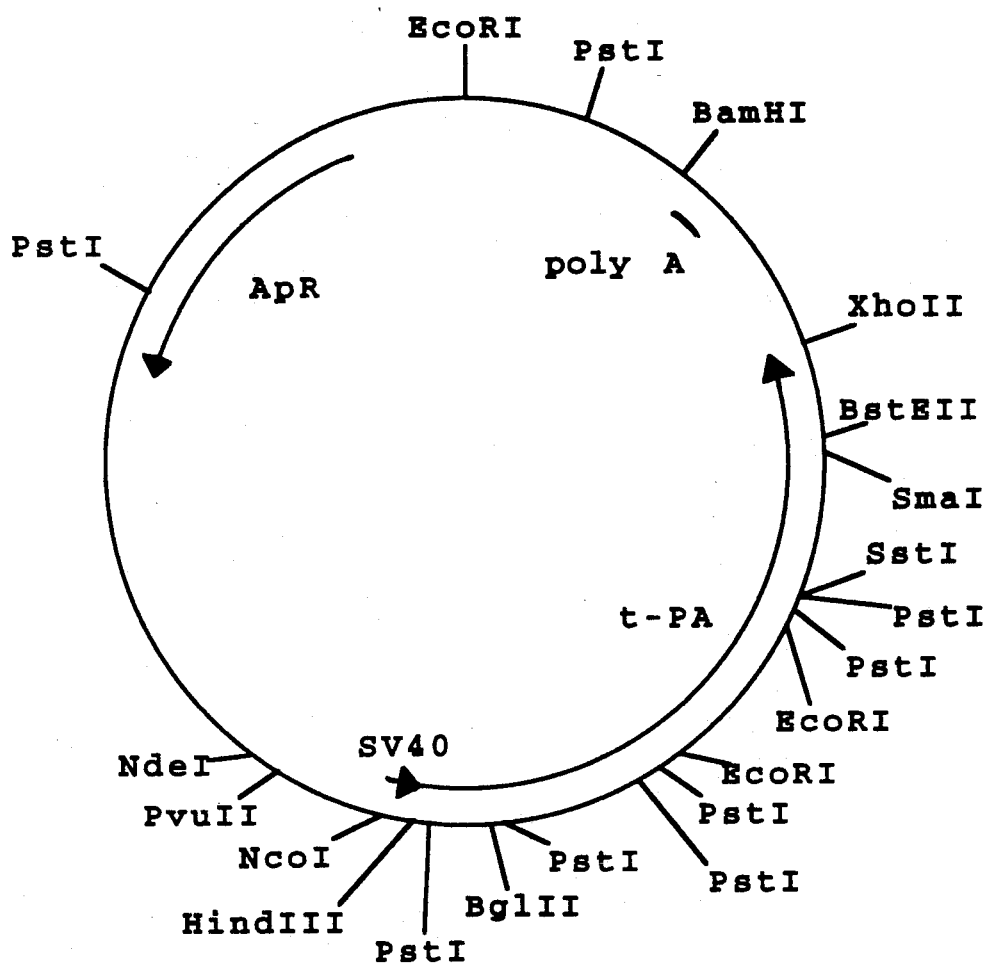
FIG. 9 is a restriction site and function map of plasmid pTPA301. The XhoII restriction site is formed during the ligation of BamHI and BglII sticky ends.
Figure 10:
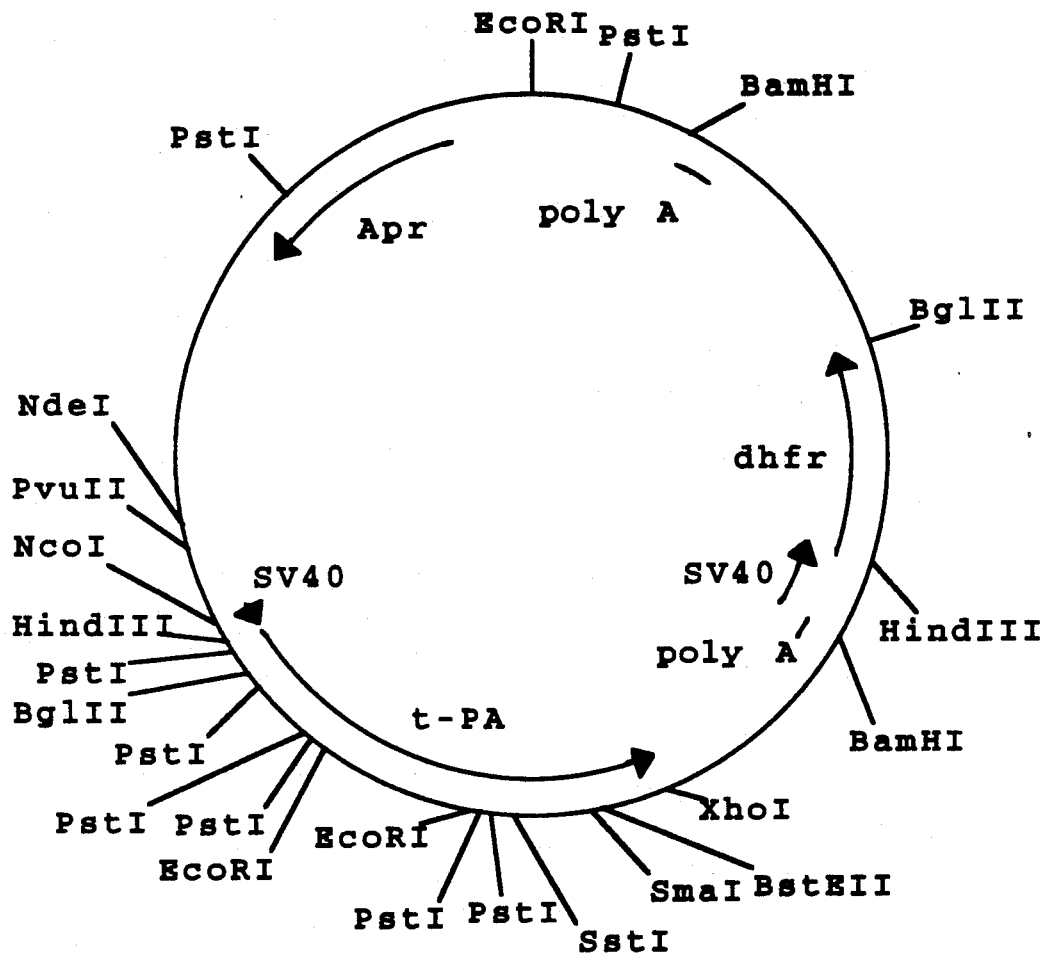
FIG. 10 is a restriction site and function map of plasmid pTPA303.
Figure 11:
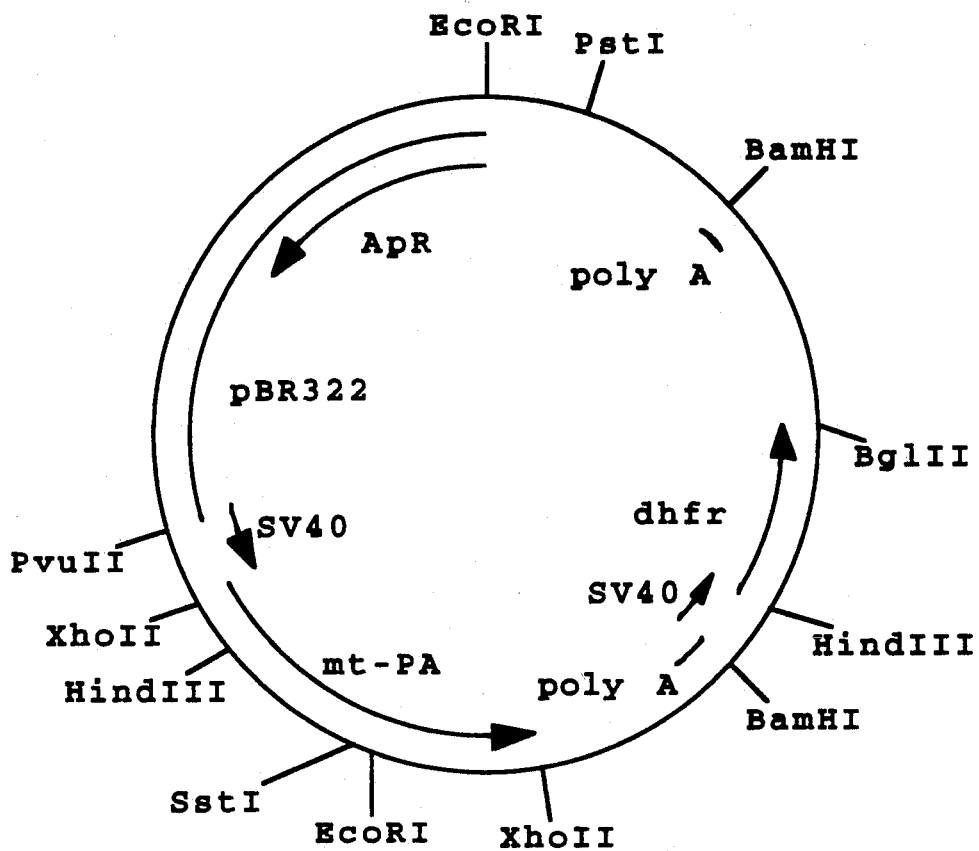
FIG. 11 is a restriction site and function map of plasmid pBW32.

A series of intermediate plasmids were initially constructed as starting materials for plasmid pBW32. Thus, an ~2.0 kb HindIII-BamHI restriction fragment of plasmid pTPA103 was ligated into BglII-HindIII-cleaved plasmid pSV2-$\beta$-globin (NRRL B-15928). The resulting plasmid, designated pTPA301, has entirely replaced the $\beta$-globin coding region with the TPA coding region. Next, a PvuII site of plasmid pSV2-dhfr (ATCC 37146) was converted to a BamHI site by the addition of DNA linkers and the ~1.9 kb BamHI fragment, comprising the cistron for the dhfr coding region, was isolated and ligated to BamHI-digested plasmid pTPA301 to form plasmid pTPA303. Restriction site and function maps of plasmids pTPA301 and pTPA303 are presented in FIGS. 9 and 10, respectively. Finally, two restriction fragments of plasmid pTPA303; an ~2.3 kb EcoRI-HindIII fragment and an ~2.0 kb SstI-HindIII fragment were isolated and ligated, along with an ~2.7 kb EcoRI-BglII fragment of plasmid pTPA301 to the ~680 bp XhoII-SstI fragment of plasmid pBW28, the latter fragment, comprising amino acid residues 1-234 of the modified t-PA gene depicted at pp. 14-15 of the present disclosure. The resultant plasmid, designated pBW32, is illustrated in FIG. 11 of the accompanying drawings; the construction is further described in Examples 8 and 9.

The illustrative plasmids of the present invention which were constructed for expression of mt-PA activity in mammalian and other eukaryotic host cells can also utilize promoters other than the SV40 early promoter. Thus, the present invention is in no way limited to the use of the particular eukaryotic promoters exemplified herein. Other promoters, such as the SV40 late promoter or promoters from eukaryotic genes, such as, for example, the estrogen-inducible chicken ovalbumin gene, the interferon genes, the glucocorticoidinducible tyrosine aminotransferase gene, the thymidine kinase gene, the major early and late adenovirus genes, the phosphoglycerate kinase gene, and the alpha factor gene can be readily isolated and modified for use on recombinant DNA expression vectors designed to produce mt-PA in eukaryotic host cells. Eukaryotic promoters can also be used in tandem to drive expression of this modified t-PA. Furthermore, a large number of retroviruses are known that infect a wide range of eukaryotic host cells. Long terminal repeats in the retrovirus DNA often encode promoter activity and can be used, in place of the SV40 early promoter described above, to drive expression of mt-PA. The only known limitation as to promoter choice, is that the expression of the present modified t-PA structural gene will occur only in those host cells in which the particular promoter associated with the modified t-PA structural gene functions. Preferred host cells for many of the eukaryotic plasmids containing the modified t-PA genes of the present invention are listed in Table I, along with appropriate comments.

TABLE I

| Host Cell | Origin | Source | Comments |
|---|---|---|---|
| *Aedes aegypti* | Mosquito Larvae | *ATCC #CCL 125 | |
| CV-1 | African Green Monkey Kidney | ATCC #CCL 70 | |
| LCC-MK$_2$ original | Rhesus Monkey Kidney | ATCC #CCL 7 | |
| LCC-MK$_2$ derivative | Rhesus Monkey Kidney | ATCC #CCL 7.1 | Grows faster than ATCC #CCL 7 |
| 3T3 | Mouse Embryo Fibroblasts | ATCC #CCL 92 | |
| CHO-K1 | Chinese Hamster Ovary | ATCC #CCL 61 | Proline-requiring. Derivatives of CHO-K1, such as the dhfr-derivative DXB11, can be generated from this host. |
| 293 | Human Embryonic Kidney | ATCC #CRL 1573 | Transformed by Adeno-5 virus |
| *Antheraea eucalypti* | Moth Ovarian Tissue | ATCC #CCL 80 | |
| HeLa | Human Cervix Epitheloid | ATCC #CCL 2 | |
| RPMI8226 | Human Myeloma | ATCC #CCL 155 | IgG lambda-type light chain secreting |
| C127I | Mouse Fibroblast | ATCC #CRL 1616 | |
| HS-Sultan | Human Plasma Cell Plasmacytoma | ATCC #CRL 1484 | |

| Host Cell | Origin | Source | Comments |
|---|---|---|---|
| *Saccharomyces cerevisiae* DBY746 | | ATCC #44773 | |

*American Type Culture Collection, 1201 Parklawn Drive, Rockville, Maryland 20852-1776

The present DNA compounds can also be expressed in prokaryotic host cells such as, for example, *E. coli*, Bacillus, and Streptomyces. This is desirable as it is generally more efficient to prepare plasmid DNA from *E. coli*. Our studies indicate that t-PA extensively depleted of carbohydrate either through tunicamycin (a glycosylation inhibitor) treatment of the cell source or through enzymatic treatment of the purified protein retains biological fibrinolytic activity. Since prokaryotic host cells usually do not glycosylate, a variety of novel modified t-PA derivatives with fibrin-binding properties can be produced by expressing the present t-PA encoding DNA in prokaryotic host cells.

A variety of prokaryotic vectors have been constructed that expressed mt-PA in *E. coli*. These vectors are derivatives of either plasmid pBW28 or pCZ106 and comprise a variety of cistron constructions, replicons and termination sequences. For example, a derivative of plasmid pBW28, designated pBW33, contains a synthetic first cistron (illustrated below) of a double cistron construction.

This XbaI-NdeI fragment replaced the ~50 bp XbaI-NdeI fragment of plasmid pBW28. The addition of the two bases, resulting from the filling in of a ClaI site present in the cistron of plasmid pBW28, changes the reading frame of the first cistron. As a result, ribosomes terminate translation of the first cistron closer to the ATG initiation site of the second cistron (encoding the mt-PA). Plasmid pBW33 expressed the modified t-PA gene in significantly greater quantities as compared to plasmid pBW28.

Figure 12:
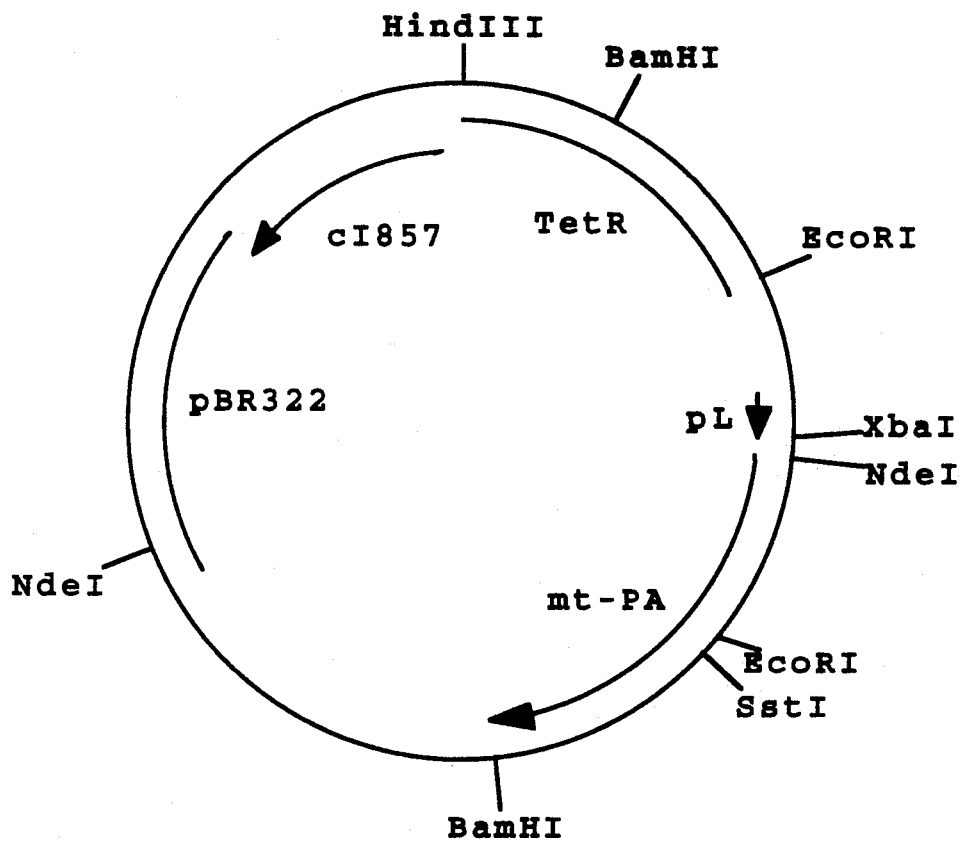
FIG. 12 is a restriction site and function map of plasmids pBW33, pBW35, and pBW36. Plasmid pBW35 is structurally similar to the restriction site map of plasmid pBW33 and pBW36, except that it does not contain the NdeI restriction site 3' to the XbaI restriction site shown in the drawing.

In plasmids pBW35 and pBW36, the first cistron has been deleted. In addition, changes were made in the translational activating sequences (described in Examples 15 and 16). These constructions also express the modified t-PA gene. A restriction site and function map of plasmids pBW33, pBW35 and pBW36 is presented in FIG. 12 of the accompanying drawings.

The cistrons depicted above, as well as the various linkers described herein, can be synthesized from single-stranded deoxyoligonucleotides by procedures well known in the art. The single-stranded deoxyoligonucleotides can be synthesized with commercially available instruments, such as the 380A DNA Synthesizer marketed by Applied Biosystems (850 Lincoln Centre Drive, Foster City, Calif. 94404), which utilizes phosphoramidite chemistry. Other procedures for synthesizing DNA are also known in the art. The conventional modified phosphotriester method of synthesizing single stranded DNA is described in Itakura et al., 1977, *Science* 198:1056 and in Crea et al., 1978, *Proc. Natl. Acad. Sci. USA* 75:5765.

In constructing suitable expression vectors, transcription termination sequences are desirable to prevent potential readthrough by the RNA polymerase. To avoid any potential interference with the transcription terminators, one skilled in the art could eliminate the 3' non-coding region of the mt-PA gene. Accordingly, plasmids pL195 and pBW44 were created to delete ~180 bp from the 3' non-coding region of on plasmid pBW33. Concurrently, one could substitute other known transcription terminators for the bacteriophage λ terminator present in plasmid pBW33. Thus, the present invention is in no way limited to the use of the particular prokaryotic transcription terminator exemplified herein. Other, transcription terminators include for example, the 1pp terminator and the phage SPO1 terminator. All of the aforementioned terminators have been previously characterized, are well known in the art, and can be constructed either synthetically or from known plasmids.

Expression of human t-PA activity in *E. coli* is in no way limited to the use of a particular promoter, since the choice of a specific promoter is not critical to the operability of the present invention. Promoters which can be substituted for the previously exemplified $\lambda P_L$ promoter include, but are not limited to, the *E. coli* lactose (lac), the *E. coli* tryptophan (trp), the *E. coli* lipoprotein (1pp), and bacteriophage $\lambda P_R$ promoters. In addition, one or more promoters can be used in tandem, such as, for example, the trp and lac promoters, or hybrid promoters, such as the tac promoter, can be used to drive expression of the modified t-PA structural gene. All of the aforementioned promoters have been previously characterized, are well known in the art, and can be constructed either synthetically or from known plasmids.

Figure 13:
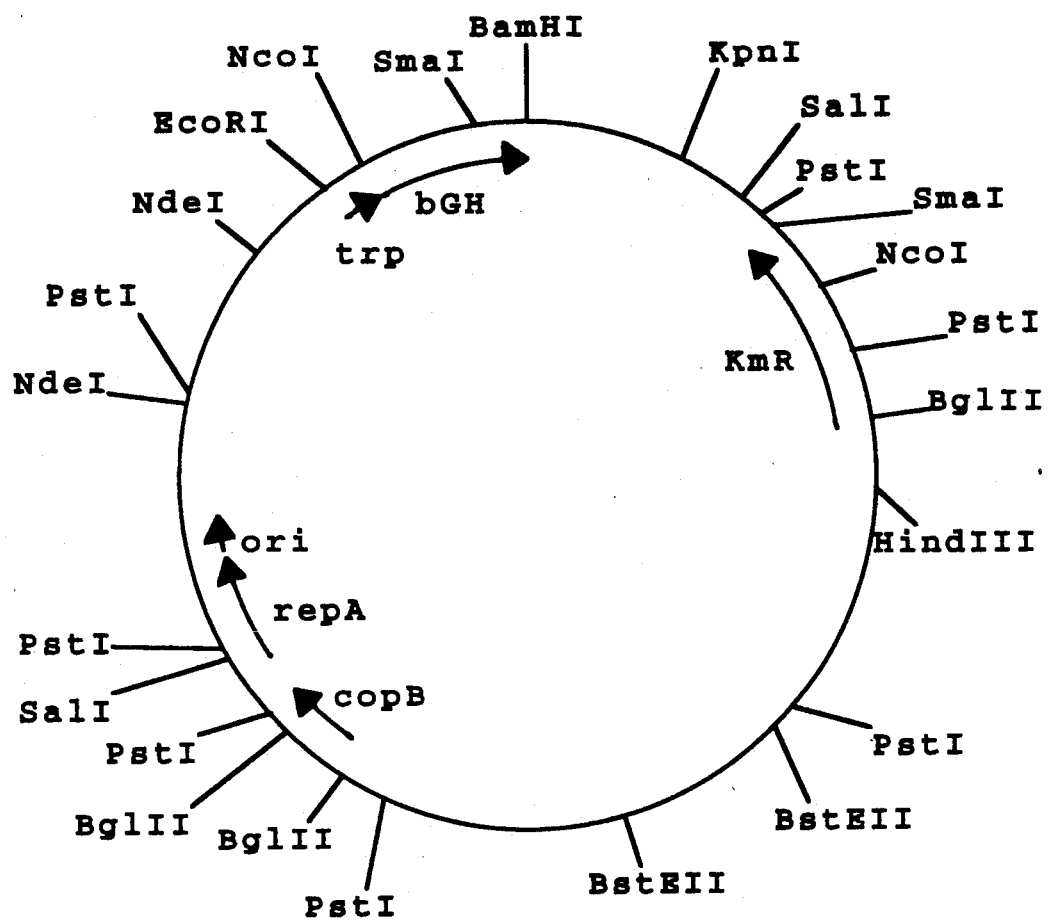
FIG. 13 is a restriction site and function map of plasmid pCZ106.

Plasmid pBW40, pBW41, or pBW42 replication is determined by a thermoinducible runaway replicon disclosed in both GB Patent Publication Number 1,557,774 and Uhlin et al., 1979, *Gene* 6:91. At temperatures below 28° C., especially 25° C., the replicon maintains a relatively low copy number of about 10–15 copies per cell. When the temperature is raised to 37° C., copy number control is completely lost and plasmids containing the replicon amplify to 1000–2000 copies per cell. The particular runaway replicon exemplified herein is contained in the plasmid pCZ106. Plasmid pCZ106 can be conventionally isolated from *E. coli* K12 RV308/pCZ106, a strain deposited with and made part of the permanent stock culture collection of the NRRL. A culture of this strain can be obtained from the NRRL under the accession number B-15959. A restriction site and function map of plasmid pCZ106 is presented in FIG. 13 of the accompanying drawings. Skilled artisans will understand that the present invention is not limited to the use of any particular runaway replicon or copy number mutant. Other inducible runaway or high copy number replicons can be obtained by appropriate selection or can be constructed in accordance with the procedure disclosed in International Publication Number WO81/02901. Such replicons can be used to construct expression vectors that are also within the scope of the present invention.

However, the present invention is not limited to the use of a runaway replicon-containing plasmid for expression of mt-PA activity in *E. coli*. Many replicons, such as those from plasmids pBR322, pACYC184, the pUC plasmids, and the like, are known in the art and are suitable for the construction of recombinant DNA cloning and expression vectors designed to drive expression of the mt-PA-encoding DNA compounds of the present invention. Neither is the present invention limited to the actual selectable markers present on the plasmid exemplified herein. A wide variety of selectable markers exist, both for eukaryotic and prokaryotic host cells, that are suitable for use on a recombinant DNA cloning or expression vector comprising a DNA compound (or sequence) of the present invention.

Many modifications and variations of the present illustrative DNA sequences and plasmids are possible. For example, the degeneracy of the genetic code allows for the substitution of nucleotides throughout polypeptide coding regions as well as for the substitution of the

```
TAA or TGA
|||    |||
ATT    ACT
``` translation stop signals for the

```
TAG
|||
ACT
``` translational stop signal specifically exemplified. Such sequences can be deduced from the now-known amino acid or DNA sequence of human t-PA and can be constructed by following conventional synthetic procedures. Therefore, the present invention is in no way limited to the DNA sequences and plasmids specifically exemplified.

The prokaryotic expression vectors and method of this invention can be applied to a wide range of host organisms, especially Gram-negative prokaryotic organisms such as *Escherichia coli, E. coli* K12, *E. coli* K12 RV308, *E. coli* K12 HB101, *E. coli* K12 C600, *E. coli* K12 SF8, *E. coli* K12 RR1, *E. coli* K12 RR1ΔM15, *E. coli* K12 MM294, *E. coli* SG936, and the like. *E. coli* SG936 is disclosed in Buell, G. et al., 1985, *Nuc. Acid Res.* 13:1923–1938. Two of the genetic mutations introduced in this strain, the lon and htpR mutations are known to promote the expression of desired proteins (see, for example, Goff and Goldberg, 1985, Cell 41:587–595). These mutations can be transduced into other strains of *E. coli* by Pl transduction according to the teaching of Miller, J. H., ed. 1972, Experiments in Molecular Genetics, Cold Spring Harbor Laboratory, Cold Spring Harbor, N.Y. Although all of the embodiments of the present invention are useful, some of the vectors and transformants are preferred. Preferred vectors include pBW32, pBW33, pBW40, pBW46, pL219, pTPA309, and pTPA311; preferred transformants include CHO-Kl/PBW32*E. coli* K12 RV308/pBW33, *E. coli* K12 N5271/pBW40, *E. coli* K12 RV308/pBW46, *E. coli* K12 RV308/pL219, CHO-Kl/pTPA309, and CHO-Kl/pTPA311.

Those skilled in the art will recognize that the expression vectors of this invention are used to transform either eukaryotic or prokaryotic host cells, such that a polypeptide with human tissue plasminogen activator activity is expressed by the host cell. If the host cell is transformed with a vector comprising a promoter that functions in the host cell and drives transcription of the mt-PA structural gene, and if the host cell possesses the cellular machinery with which to process the signal peptide, this modified t-PA molecule can be isolated from the media. Under other expression conditions, such as when plasmid pBW33 is in *E. coli* RV308, the modified t-PA molecule must be isolated from the host cell.

As stated above, recombinant mt-PA will be useful in the treatment of a wide variety of acquired disease states involving intravascular coagulation including deep vein thrombosis, pulmonary embolism, peripheral arterial thrombosis, emboli originating from the heart or peripheral arteries, acute myocardial infarction, and thrombotic strokes.

Experimental data suggest that conventional thrombolytic agents SK-plasmin and UK are useful in the treatment of invasive cancer and act to prevent or reduce the distant metastatic lesions of these malignancies. Recombinant mt-PA represents an attractive therapeutic modality in these clinical situations for the reasons detailed below.

In established objectively documented deep vein thrombosis and/or pulmonary embolism, the loading dose of mt-PA ranges from $2.5\times10^5-5\times10^6$ units followed by a continuous infusion in amounts ranging from $2.5\times10^5-5\times10^6$ units/hour. The exact dose can be predicted only from animal experiments and phase I human clinical trials. However, it is anticipated that mt-PA which interacts inefficiently with PA inhibitors can be therapeutically effective in doses ranging from one-third to two-thirds the dose of authentic t-PA. Similar dosage schedules are applicable for the treatment of peripheral arterial thrombi. In acute myocardial infarction, the estimated dose is $2.5\times7.5\times10^6$ units administered over a period of 30–90 minutes.

Because of the lower likelihood of bleeding complications from mt-PA infusions, mt-PA is an attractive alternative to conventional thrombolytic agents in the treatment of thromboembolism in the immediate postsurgical period. Also, mt-PA may be used prior to or in conjunction with thrombectomies and embolectomies, surgical procedures which are often necessary to save ischemical limbs from amputation in the setting of an acute arterial obstruction.

Arterial emboli originating from the heart are frequent complications in diseases of the heart involving heart valves, in patients with artificial heart valves, in acute myocardial infarction and in certain types of heart arrhythmias. The treatment of these problems with conventional thrombolytic agents is frequently ineffective, the risk of bleeding complications is substantial particularly if the embolus is lodged in a major cerebral artery. Recombinant mt-PA which appears to be a highly effective thrombolytic agent carrying a low risk of bleeding complications has substantial utility in the treatment of cardiogenic emboli.

Similarly, emboli originating from thrombi in peripheral arteries, most notably the carotid arteries which tend to lodge in the brain can be treated with conventional thrombolytic agents only at extremely high risk to the patient for major intracerebral bleeding complications. Recombinant mt-PA with its reduced potential for bleeding complications may well have utility in this clinical situation.

Recombinant mt-PA may also be useful in the treatment of thrombotic strokes particularly the so-called "stroke in evolution." Conventional thrombolytic agents given to patients with completed strokes or "strokes in evolution" had disastrous consequences in the form of severely debilitating or fatal intracerebral bleeds. Similarly, treatment of strokes with either heparin or oral anticoagulants, although occasionally beneficial, carry a high risk for bleeding into the infarcted brain area thereby aggravating the neurological deficit accompanying the stroke. Because of its low potential for causing bleeding complications and its selectivity, it is expected that mt-PA can be given to stroke victims and will be beneficial in dissolving the occluding thrombus thereby reducing the neurological deficit resulting from the stroke provided the agent is administered early enough after the onset of symptoms.

Recombinant mt-PA like authentic t-PA, will be a useful treatment in acute myocardial infarction. As has recently been demonstrated, authentic t-PA when administered I.V. in doses of 30–70 mg over 1–3 hours is effective in dissolving occluding coronary thrombi, reestablishing myocardial perfusion and salvaging large areas of ischemic myocardium. Because of its diminished interaction with PA inhibitors, it is anticipated that mt-PA will be as effective as authentic t-PA and conceivably that it can be administered in doses 30–60% of those doses recommended for authentic t-PA and be as clinically efficient as the authentic molecule.

Evidence has been presented in experimental animals that conventional thrombolytic agents SK plasmin and UK are useful in the treatment of invasive malignant tumors. Many tumor cells produce substances which trigger the activation of the coagulation system resulting in localized fibrin deposits. These fibrin deposits function as "nests" in which cancer cells can divide to form mestastatic lesions. The lysis of these fibrin deposits are thought to prevent the growth of metastatic malignancies. Conventional thrombolytic agents given to patients with widespread cancers probably pose an unacceptable risk for bleeding complications. Patients with invasive cancers are usually placed on aggressive chemotherapeutic regimens resulting in profound thrombocytopenia and the combined effects of thrombocytopenia and a fibrinolytic coagulation defect unquestionably will produce severe bleeding problems in the majority of patients. Because of its low potential for bleeding complications and high selectivity, it is likely that mt-PA can be given safely to patients which are thrombocytopenic as the result of aggressive cancer chemotherapy.

It has been postulated that sizable numbers of patients develop venous thromboembolism because of defective synthesis and/or secretion of endothelial cell derived t-PA. In the past, such patients have been treated effectively with a combination of anabolic steroids and phenformin which results in an increase in intrinsic t-PA synthesis. This long-term regimen was found to sharply reduce the incidence of recurrent deep-vein thrombosis, pulmonary embolism or both; however, this therapeutic regimen was abandoned because of an unacceptably high risk of serious side effects. Recombinant mt-PA administered through continuous infusion using light weight portable pump systems may have substantial utility in the prevention of recurrent thromboembolic events in suitably selected patients.

The compounds of the present invention can be formulated according to known methods to prepare pharmaceutically useful compositions, whereby the modified human t-PA product of the present invention is combined in admixture with a pharmaceutically acceptable carrier vehicle. Suitable carrier vehicles and their formulation, inclusive of other human proteins, e.g., human serum albumin, are described, for example in *Remington's Pharmaceutical Sciences* 16th ed., 1980, Mack Publishing Co., edited by Osol et al., which is hereby incorporated by reference. Such compositions will contain an effective amount of mt-PA together with a suitable amount of carrier vehicle in order to prepare pharmaceutically acceptable compositions suitable for effective administration to the host. The mt-PA composition can be administered parenterally, or by other methods that ensure its delivery to the bloodstream in an effective form.

The following examples further illustrate the invention disclosed herein. The examples describe the procedures for the construction of the present invention, and explanations of the procedures are provided where appropriate. All cited publications are herein incorporated by reference.

EXAMPLE 1

Culture of *E. coli* MM294/pTPA102 and Isolation of Plasmid pTPA102

A. Culture of *E. coli* MM294/pTPA102

One liter of M9 medium (Maniatis et al., 1982, *Molecular Cloning*, Cold Spring Harbor Laboratory) containing 0.2% casamino acids and 100 μg/ml ampicillin was innoculated with a culture of *E. coli* MM294/pTPA102 (NRRL B-15834) and incubated with shaking at 37° C. until the optical density (O.D.) at 590 nm was ~0.5 absorbance unit. At that time, chloramphenicol powder was added to a final concentration of 250 mg/ml and incubation continued overnight.

B. Isolation of Plasmid pTPA102

*E. coli* MM294/pTPA102 were harvested from the culture described in Example 1A following a procedure adapted from Maniatis et al., 1982.

The cells were harvested by centrifugation at 4000 g for 10 minutes at 4° C., and the supernatant was discarded. The cell pellet was washed in 100 ml of ice-cold STE buffer (0.1 M NaCl; 10 mM Tris-HCl, pH 7.8; and 1 mM EDTA). After washing, the cell pellet was resuspended in 10 ml of Solution 1 (50 mM glucose; 25 mM Tris-HCl, pH 8.0; and 10 mM EDTA) containing 5 mg/ml lysozyme and left at room temperature for 10 minutes. Twenty ml of Solution 2 (0.2 N NaOH and 1% SDS) were then added to the lysozyme-treated cells, and the solution was gently mixed by inversion. The mixture was incubated on ice for 10 minutes.

Fifteen ml of ice-cold 5M potassium acetate, pH 4.8, were added to the lysed-cell mixture and the solution mixed by inversion. The solution was incubated on ice for 10 minutes. The 5M potassium acetate solution was prepared by adding 11.5 ml of glacial acetic acid to 28.5 ml of water and 60 ml of 5M potassium acetate; the resulting solution is 3M with respect to potassium and 5M with respect to acetate.

The lysed cell mixture was centrifuged in a Beckman SW27 (or its equivalent) at 20,000 rpm for 20 minutes at 4° C. The cell DNA and debris formed a pellet on the bottom of the tube. About 36 ml of supernatant were recovered, and 0.6 volumes of isopropanol were added, mixed, and the resulting solution left at room temperature for 15 minutes. The plasmid DNA was collected by centrifugation at 12,000 g for 30 minutes at room temperature. The supernatant was discarded, and the DNA pellet was washed with 70% ethanol at room temperature. The ethanol wash was decanted, and the pellet was dried in a vacuum desiccator. The pellet was then resuspended in 8 ml of TE buffer.

Eight grams of CsCl were added to the DNA solution. About 0.8 ml of a 10 mg/ml solution of ethidium bromide in water were added for each 10 ml of CsCl-DNA solution. The final density of the solution was about 1.55 g/ml, and the ethidium bromide concentration was about 600 μg/ml. The solution was transferred to a Beckman Type 50 centrifuge tube, filled to the top with paraffin oil, sealed, and centrifuged at 45,000 rpm for 24 hours at 20° C. After centrifugation, two bands of DNA were visible in ordinary light. After removing the cap from the tube, the lower DNA band was removed by using a syringe with a ~21 hypodermic needle inserted through the side of the centrifuge tube.

The ethidium bromide was removed by several extractions with water-saturated 1-butanol. The CsCl was removed by dialysis against TE buffer. After extractions with buffered phenol and then chloroform, the DNA was precipitated, washed with 70% ethanol, and dried. About 1 mg of plasmid pTPA102 was obtained and stored at 4° C. in TE buffer at a concentration of about 1 μg/μl. A restriction site and function map of plasmid pTPA102 is presented in FIG. 4 of the accompanying drawings.

EXAMPLE 2

A. Construction of Intermediate Plasmid pTPA103

About 50 μg of plasmid pTPA102 isolated from *E. coli* K12 MM294 cells (NRRL B-15625) were digested to completion with 50 units of TthIII.1 restriction enzyme* in restriction buffer A (100 mM NaCl, 10 mM Tris-HCl pH 8, 10 mM MgCl₂, 1 mM dithiothreitol) at 37° C. The digestion yielded 3 fragments; 4.4 kb, 3.1 kb, and 0.5 kb in size. The separated fragments were located in an agarose gel by staining with ethidium bromide and visualizing fluorescent bands with ultraviolet light. A slice containing the 4.4 kb fragment was cut out with a razor blade and DEAE membrane (NA45, Schleicher and Schuell, Inc.) was inserted into the slit. The gel slice was then returned to its original position. Electrophoresis was continued until the DNA migrated onto the DEAE membrane. The position of the membrane containing the DNA was cut out and washed 3X with 200 μl of 150 mM NaCl in 20 mM Tris-HCl pH 8 in a 0.5 ml Eppendorf tube. The DNA was eluted off the membrane with 200 μl 1M NaCl in 20 mM Tris-HCl pH 8 at 65° C. The DNA was then precipitated with 2.5 volumes 95% ethanol, resuspended in 0.3M NaOAc, reprecipitated and collected by centrifugation.

*Restriction enzymes and instructions can be obtained from the following sources:
New England Biolabs., Inc., 32 Tozer Road, Beverly, Mass. 01915
Boehringer-Mannheim Biochemicals, 7941 Castleway Drive, Indianapolis, Ind. 46250
Bethesda Research Laboratories Inc., 8717 Grovemont Circle, Gaithersburg, Md. 20760.

About 5 μg of the DNA pellet was resuspended in 100 μl of nick-translation buffer (NTB; 50 mM Tris-HCl pH 7.2, 10 mM MgSO₄, 0.1 mM DTT) to which 1 μl of each dNTP (10 mM dATP, dTTP, dCTP, dGTP) and 10 units of Klenow enzyme, which is the large fragment of *E. coli* DNA polymerase I, (Boehringer Mannheim) were added. The reaction was carried out at room temperature (20° C.) for 30 minutes and terminated by heat treatment at 65° C. for 5 minutes. BamHI linkers (5'-CGGATCCG-3' from New England Biolabs) were kinased and ligated to the 4.4 kb fragment.

The resulting ligation mix (20 μl) was diluted into 100 μl 1XA restriction buffer and 10 units of BamHI and 1 unit of HindIII restriction enzyme were added. Incubation was at 37° C. until a 2.4 kb and a 2.0 kb fragment were generated. The fragments were separated on a 1% agarose gel and the 2.0 kb fragment was gel-purified as taught above, and then ligated between the HindIII and BamHI sites of plasmid pRC.

Before transformation, the ligation mix (20 μl) was diluted into 100 μl of restriction buffer A and 2 μl of NcoI restriction enzyme was added prior to incubation at 37° C. for 2 hours. This treatment eliminates undesired recombinants.

B. Transformation

The resultant ligation mixture was used to transform, in substantial accordance with the transformation procedure of Wensink, 1974, *Cell* 3:315, *E. coli* K12 RV308 on TY plates (1% tryptone, 0.5% yeast extract, 0.5% sodium chloride, 1.5% agar, pH 7.4) containing 50 μg/ml of ampicillin. Bacterial strain *E. coli* K12 RV308 has been deposited and made part of the permanent stock culture collection of the Northern Regional Research Laboratory, Peoria, Illinois, from which it is available to the public under the accession number NRRL B-15624.

The transformants were identified by their ampicillin resistant and kanamycin sensitive phenotype and by restriction enzyme analysis of plasmid DNA. The resultant cells were used to isolate plasmid pTPA103 in substantial accordance with the procedure of Example 1.

C. Construction of plasmid pTPA103 der NdeI

About 1 μg of plasmid pTPA103 in 20 μl of A restriction buffer was digested at 37° C. with restriction enzyme BglII to produce linears. The linearized plasmid was precipitated with 2.5 volumes of ethanol in the presence of 0.3M NaOAc and the DNA was collected by centrifugation. The DNA pellet was resuspended in 100 μl nick-translation buffer to which 1 μl of each (10 mM dATP, dTTP, dCTP dGTP) and 10 units of Klenow enzyme (Boehringer) were added. The reaction was carried out at room temperature (20° C.) for 30 minutes and terminated by heat treatment at 65° for 5 min.). About 0.1 μg of NdeI linkers (5'-CCATATGG-3', New England Biolabs) were heated to 90° C. in 10 μl of TE buffer (10 mM Tris-HCl pH 8; 1 mM EDTA) and reannealed by slowly lowering the temperature to 15° C. The linkers were added to the "filled-in" BglII fragment, in the presence of 1 μl T4 DNA ligase (40,000 units/ml) and ATP (0.5 mM final concentration). Ligation was at 15° C. for 20 hours. The ligation mix was then transformed into competent *E. coli* K12 RV308 cells. Transformants were identified by their ampicillin resistant phenotype and by restriction enzyme analysis. DNA sequencing confirmed that pTPA103 der NdeI contained the following sequence:

5'.....CCATATGGGATCTTAC...3'

EXAMPLE 3

A. Construction of Plasmid pUC19 TPA FE

About 10 μg of plasmid pTPA103 der NdeI was digested in 100 μl of restriction enzyme buffer A with 20 units AvaII at 37° C. for 5 hours. The resulting restriction fragments were separated on a 1% agarose gel and the 1400 bp fragment was purified according to the teaching of Example 2A. About 1 μg of the purified 1400 bp fragment in 20 μl NTB buffer was treated with Klenow enzyme and 55 picomoles of kinased HpaI linkers (5'-CGTTAACG-3') were ligated in 100 μl of ligation buffer according to the teaching in Example 2.

The DNA fragment used to construct the linker can be synthesized either by using a Systec 1450A DNA Synthesizer (Systec Inc., 3816 Chandler Drive, Minneapolis, Mn.) or an ABS 380A DNA Synthesizer (Applied Biosystems, Inc., 850 Lincoln Centre Drive, Foster City, Calif. 94404). Many DNA synthesizing instruments are known in the art and can be used to make the fragment. In addition, the fragment can also be conventionally prepared in substantial accordance with the procedures of Itakura et al., 1977, *Science*, 198:1056 and Crea et al., 1978, *Proc. Natl. Acad. Sci. USA*, 75:5765. After ligation, 10 μl of 1M Tris-HCl pH 8 and 5 units of EcoRI restriction enzyme were added and the digestion was carried out at 37° C. until complete. The sample was treated at 65° C. for 5 minutes and the DNA was precipitated with 2.5 volumes of 95% ethanol in the presence of 0.3M NaOAc. The DNA was collected by centrifugation and resuspended in 10 μl of ligation buffer.

About 5 μg of plasmid pUC19 (Pharmacia, Inc., 800 Centennial Dr., Piscataway, N.J.) were digested to completion at 37° C. with SmaI restriction enzyme in 100 μl restriction buffer containing 10 mM Tris-HCl, pH 8, 10 mM $MgCl_2$; 1 mM β-mercapthoethanol and 20 mM KCl. About 10 μl of 1M Tris-HCl pH 8 and 10 units of EcoRI restriction enzyme were added and incubation was continued at 37° C. until the digestion was complete. The digested plasmid DNA was run on a 1% agarose gel and the large EcoRI to SmaI restriction fragment was gel-purified. About 1 μg of the gel-purified fragment was dissolved in 10 μl ligation buffer and mixed with the 770 bp fragment from pTPA103 der NdeI prepared as described above. Two μl of 0.5 mM ATP and 1 μl of T4 DNA ligase (40,000 units/ml; NEB) were added and ligation carried out at 15° C. for 2 hours. The ligation mix was diluted into 100 μl of ligase buffer containing 500 mM ATP and 40 units of T4 DNA ligase and kept at 23° C. for 2 hours.

About 10 μl of the ligation mix was transformed into competent *E. coli* K12 RRIΔM15 cells (NRRL B-15440) which were plated on TY agar plates containing 100 μg/ml ampicillin, 40 μg/ml X-gal (Sigma) and 1 mM IPTG (Sigma). The plates were incubated at 37° C. overnight and the transformants were identified by their inability to utilize the X-gal resulting in a "white" colony phenotype. These colonies were grown in TY broth containing 100 μg/ml ampicillin and plasmid DNA was extracted for restriction analysis. The desired plasmid had an insert of about 770 bp and new restriction sites for NdeI and HpaI. The plasmid, designated pUC19 TPA FE, contains the first 96 amino acid residues of native t-PA but, due to the addition of the translational activating sequence, the amino acid sequence has been renumbered to include the amino acid residues MET and GLY as amino acid residue numbers 1 and 2, respectively.

B. Competitive t-PA Binding Studies

The 1-98 peptide of plasmid pUC19 TPA FE was purified first through differential centrifugation of disrupted *E. coli* yielding granules containing the peptide. The granules were characteristically solubilized in 7M urea. The extracted crude preparation of peptide 1-98 was carboxymethylated using iodoacetic acid in 7M urea under nonreducing conditions. This step was included to eliminate the one known free sulphydryl in the peptide (residue 85). The preparation was then dialyzed extensively against 0.1M $PO_4$, 0.15M NaCl, pH 7.4. The preparation remained clear without demonstrable precipitation after dialysis. Peptide 1-98 was next purified to apparent homogeneity either by immunoabsorption or reverse phase HPLC. Immunopurified material was adsorbed to immobilized polyclonal t-PA antibody and desorbed with 0.1M glycine buffer, pH 3.5. Reverse phase HPLC purification was readily accomplished on a C-4 (300 Å) silica based resin.

The purified "finger"-EGF peptide 1-98 was then used in competitive t-PA binding studies. Briefly, wells of 96-well microtiter plates were coated with fibronectin-free, plasminogen-free human fibrin. Authentic t-PA purified from the conditioned medium of Bowes melanoma cells in culture was added to these wells and allowed to equilibrate with the fibrin layer for 4 hours. The plates were extensively washed and to the washed plates was added the t-PA specific paranitroanilide substrate, S-2288. The substrate quantifies the t-PA firmly bound to fibrin after the washing procedures. After overnight incubation, the hydrolysis of S-2288 is quantified by reading in a plate reader the intensity of the yellow color which develops as the substrate is cleaved ($A_{405nm}$).

For quantification of fibrin-dependent t-PA plasminogen activation, plasminogen-free, fibronectin-free human fibrin coated microtiter wells were again utilized. To these wells were added authentic purified t-PA, highly purified human plasminogen and the paranitroanilide tripeptide substrate, S-2251, which is readily hydrolyzed by plasmin but not by t-PA. After 5 hours incubation, the hydrolysis of S-2251 ) was measured in the plate reader.

Figure 7:
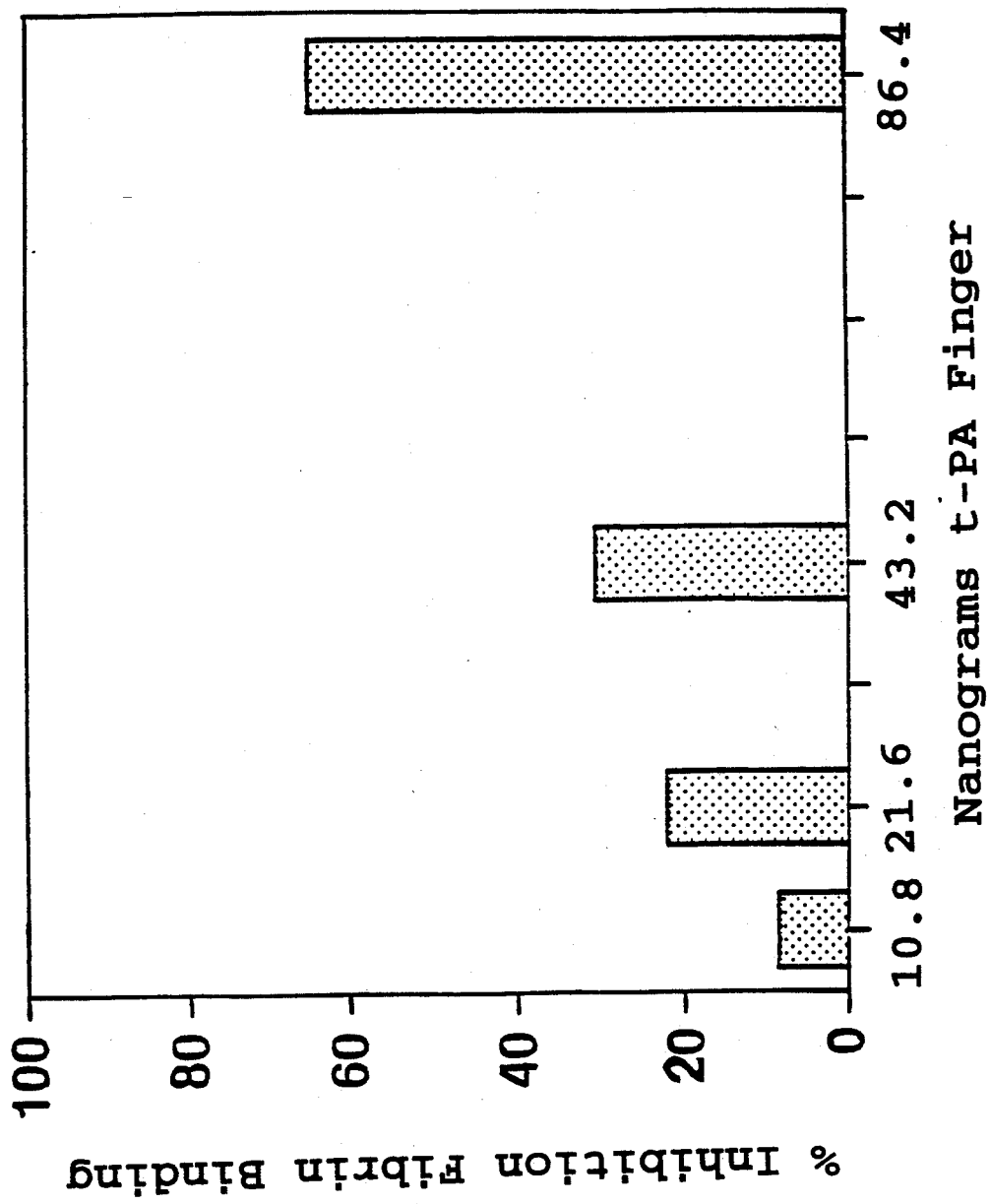
FIG. 7 shows competitive t-PA inhibition binding data.

FIG. 7 summarizes an experiment in which authentic t-PA (1,000 mU) was added to fibrin coated wells, admixed with increasing concentrations of the purified peptide 1-98 in a concentration range of 10.8-86.4 ng/well. A concentration dependent inhibition of t-PA fibrin finding increasing with increasing concentrations of the "finger" is clearly demonstrated.

When increasing concentrations of the peptide 1-98 were added to t-PA plasminogen mixtures in fibrin coated microtiter wells, this resulted in progressively increasing inhibition of plasminogen activation.

EXAMPLE 4

Construction of Plasmid pBW25

A. Isolation of pUC19 TPA FE HpaI-BamHI Fragment

Six to eight μg of pUC19 TPA FE were digested with 18 units of HpaI restriction enzyme in 100 μl of HpaI buffer for twenty minutes at 37° C. in order to achieve only partial digestion as determined by analytical gel electrophoresis. The reaction salt concentration was adjusted to 150 μl BamHI buffer (150 mM NaCl, 10 mM Tris pH 8.0, 10 mM MgCl₂) and 16 units of BamHI restriction enzyme were added. This reaction was incubated at 37° C. for 90 minutes to completion. DNA was concentrated by ethanol precipitation and electrophoresed on a preparative 1.5% agarose gel. The gel was stained in 1 μg/ml ethidium bromide and DNA bands visualized under long wave UV light. The appropriate large HpaI-BamHI band (as determined by comparison to a complete HpaI-BamHI digest and intact plasmid) was excised and frozen for one hour at −20° C. DNA was recovered by the method of freeze-squeeze (Thuring et al., 1975, *Anal. Biochem* 66:213) and precipitated twice out of 0.3M NaOAc with 2.5 volumes of 95% ethanol. The final pellet was rinsed twice with 70% ethanol, dried in vacuo and resuspended in 20 μl distilled water.

B. Isolation of the ~1015 bp ScaI-BamHI Fragment of Plasmid pTPA103

About 13 μg of pTPA103 were digested with 18 units of ScaI restriction enzyme in 100 μl ScaI buffer (100 mM NaCl, 10 mM Tris pH 7.5, 10 mM MgCl₂) at 37° C. for 90 minutes. The reaction was adjusted to 150 μl BamHI buffer and 16 units of BamHI restriction enzyme were added and the reaction incubated at 37° C. for 90 minutes. DNA was concentrated by ethanol precipitation prior to loading on a 1.5% agarose preparative gel. The ~1015 bp ScaI-BamHI band was visualized, excised and recovered as described in Example 4A.

C. Ligation

About 100 ng of each of the above fragments described in Examples 4A and 4B were ligated in a 20 μl reaction mix containing 50 mM Tris-HCl pH 7.5, 10 mM MgCl₂, 10 mM DTT, 6 μg BSA and 1 mM ATP unit ligase (Promega Biotech) for 18 hours at 16° C.

D. Transformation into *E. coli* MM294

The above ligation mix was diluted to 50 μl with 50 mM NaCl-10 mM MgCl₂-10 mM CaCl₂ and used to transform 100 μl freshly prepared competent *E. coli* MM294 cells in accordance with the teaching of Example 2B. The transformation mix was plated onto BHI (Brain Heart Infusion - Difco) plates containing 100 μg/ml ampicillin. Transformants were identified by their ampicillin resistant phenotype and restriction enzyme analysis of plasmid DNA, including the presence of an ~1079 bp EcoRI fragment.

E. Culture of *E. coli* MM294/pBW25 and Isolation of Plasmid pBW25

*E. coli* MM294/pBW25 was cultured essentially as described in Example 1A except that BHI broth was used instead of TY.

Plasmid isolation was performed essentially as taught in Example 1B except that one discontinuous CsCl gradient (density=1.80 g/ml and 1.47 g/ml) was performed instead of two successive homogenous gradients (Garger et al., 1983, *Biochemical and Biophysical Res. Comm.*, 117(3):835).

EXAMPLE 5

Construction of Plasmid pM8BW26

A. Isolation of the ~810 bp HindIII-EcoRI Fragment of Plasmid pBW25

About 5 μg of plasmid pBW25 were digested with 10 units HindIII in 150 μl 1X HindIII buffer (50 mM NaCl, 10 mM Tris-HCl pH 8.0, 10 mM NaCl₂) at 37° C. for 90 minutes. Fifteen μl 1M Tris-HCl pH 7.6 and 24 units EcoRI were added and incubation at 37° C. continued for 90 minutes. The DNA was concentrated by ethanol precipitation and electrophoresed on a 1.5% agarose preparative gel. The ~810 bp fragment was visualized and recovered as described in Example 4A.

B. Isolation of the ~7.2 kb EcoRI-HindIII M13mp8 Vector

About 4.5 μg M13mp8 DNA (available from NEB) was digested as described in Example 5A. The ~7.2 kb EcoRI-HindIII vector fragment was electrophoresed, identified and recovered as described in Example 4A.

C. Ligation and Transfection of *E. coli* JM103

About 0.1 μg each of the EcoRI-HindIII fragment from pBW25 and the EcoRI-HindIII vector from M13mp8 were ligated as described in Example 4C except that the reaction temperature was 14° C. *E. coli* JM103 cells (BRL) were made competent and transfected with the ligation mix essentially as described in the BRL M13 Cloning/'Dideoxy' Sequencing Instruction Manual except that the amount of DNA used per transfection was varied. Recombinant plaques were identified by insertional inactivation of β-galactosidase activity (white plaque formation) and verified by restriction digests of RF DNA. For screening purposes, six white plaques were picked into 2.5 ml TY broth to which was added 0.4 mls log phase JM103 (TY broth culture was innoculated from minimal media stock to insure retention of F episome which also carries proAB). Cultures were incubated at 37° C. with shaking for 8 hours. Cells from 1.5 ml aliquots were pelleted and RF DNA isolated in substantial accordance with the teaching of the alkaline miniscreen procedure of Birnboim and Doly, 1979, *Nuc. Acid Res.* 7:1513. The remainder of each culture was stored at 4° C. for stock.

D. Culture of JM103/pM8BW26 and Isolation of Single Stranded pM8BW26

Fifty mls log phase JM103 were infected with appropriate stock (described in Example 5C) and incubated at 37° C. with shaking for 18 hours. Cells were pelleted by low speed centrifugation and single stranded DNA prepared from the culture supernatant by scaling up the procedure given in the aforementioned manual.

EXAMPLE 6

Site Specific Mutagenesis to Construct Plasmid pM8BW27

A. Mutagenesis

Single-stranded pM8BW26 was mutagenized in substantial accordance with the teaching of Adelman et al., 1983, *DNA* 2(3): 183–193, except that the Klenow reaction was done at room temperature for 30 minutes, followed by 60 minutes at 37° C., followed by 10° C. for 18 hours. In addition, the S1 treatment was done at 20° C. for 5 minutes, the salt concentration was reduced in half and the M13 sequencing primer (BRL) was used. The synthetic oligodeoxyribonucleotide primer used was 5'-GGGAAGTGCTGTGAAATATCCACCTGCGGCCTGAGA-3' to delete amino acid residues 87 through 261 of the native t-PA.

B. Transfection of JM103 and Identification of Recombinants

The resulting mutagenesis mix was used to transfect JM103 as taught in Example 5C. Desired mutants were identified by restriction digest analysis of RF DNA and by Maxam and Gilbert DNA sequencing.

EXAMPLE 7
Construction of Plasmid pBW28

A. Isolation of the ~689 bp EcoRI-BamHI Fragment from Plasmid pTPA103

Plasmid pTPA103 was digested to completion in 1×BamHI buffer with BamHI restriction enzyme. The buffer concentration was adjusted to accommodate EcoRI digestion as taught in Example 5A. The fragment was isolated and recovered in substantial accordance with the teaching in Example 4A.

B. Isolation of XbaI-BamHI Vector of Plasmid pL110

Plasmid pL110 (the constructing of pL110 is disclosed in Examples 20-30) was partially digested with BamHI restriction enzyme. The reaction was extracted once with equal volume chloroform and the aqueous phase ethanol precipitated. The recovered DNA was then digested to completion with XbaI restriction enzyme in 1X XbaI buffer (150 mM NaCl, 10 mM Tris HCl pH 7.9, 10 mM MgCl$_2$) at 37° C. The ~5900 bp XbaI-BamHI linear fragment was isolated and recovered in accordance with the teaching in Example 4A.

C. Construction of a Double Cistron

A linker can be synthesized as taught in Example 3A. The sequence of this fragment is as follows:

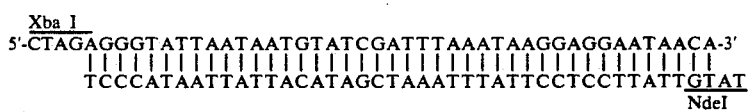

D. Isolation of the ~563 bp NdeI-EcoRI Fragment from Plasmid pM8BW27

RF pM8BW27 was digested with NdeI restriction enzyme, followed by EcoRI restriction enzyme, in substantial accordance with the teaching of Example 7A, except that the enzyme NdeI was substituted for BamHI. The fragment was isolated and recovered in substantial accordance with the teaching in Example 4A.

E. Ligation and Construction of E. coli MM294/pBW28

About 50 ng of each of the above fragments described in Examples A through D were ligated and E. coli MM294 transformed in substantial accordance with the teaching of Example 4C and 4D. Transformants were identified by their tetracycline resistant phenotype and restriction enzyme analysis of plasmid DNA.

EXAMPLE 8
Construction of Plasmid pTPA303

A. Isolation of the ~4.2 kb BglII-HindIII Restriction Fragment of Plasmid pSV2-β-globin Approximately 10 μg of plasmid pSV2-β-globin DNA (NRRL B-15928) were dissolved in 10 μl 10×HindIII reaction buffer, 5 μl (~50 units) restriction enzyme HindIII, and 85 μl H$_2$O, and the reaction was placed at 37° C. for 2 hours. The reaction mixture was then made 0.15M in LiCl, and after adding 2.5 volumes of ethanol and chilling in a dry ice-ethanol bath, the DNA was pelleted by centrifugation.

The DNA pellet was dissolved in 10 μl 10×BglII buffer, 5 μl (~50 units) restriction enzyme BglII, and 85 μl H$_2$O, and the reaction was placed at 37° C. for 2 hours. After the BglII digestion, the reaction mixture was loaded onto a 0.85% agarose gel, and the fragments were separated by electrophoresis. After inspecting the gel stained with ethidium bromide under ultraviolet light, the band containing the desired ~4.2 kb HindIII-BglII fragment was excised from the gel, and extracted as described in Example 4A. The pellet was resuspended in 10 μl of dH$_2$O and constituted ~5 μg of the desired ~4.2 kb HindIII-BglII restriction fragment of plasmid pSV2-β-globin.

B. Isolation of the ~2.0 kb HindIII-BamHI Restriction Fragment of Plasmid pTPA103.

The isolation of the desired ~2.0 kb HindIII-BamHI restriction fragment of plasmid pTPA103 from Example 2 was accomplished in substantial accordance with the above teaching. The ~5 ug of DNA obtained were suspended in 10 μl of dH$_2$O and stored at −20° C.

C. Ligation of Fragments to Construct Intermediate Plasmid pTPA301.

Two ~1 of the ~4.2 kb BglII-HindIII restriction fragment of plasmid pSV2-β-globin, 4 μl of the ~2.0 kb HindIII-BamHl fragment of plasmid pTPA103 were mixed together and then incubated with 2 μl 10×ligase buffer, 2 μl 10 mM ATP, 1 μl T4 DNA ligase (~10 units), and 9 μl of H$_2$O at 4° C. overnight. The ligated DNA constitutes the desired plasmid pTPA301; a restriction site and function map of the plasmid is presented in FIG. 13 of the accompanying drawings.

D. Construction of E. coli K12 RR1/pTPA301

The desired E. coli RR1/pTPA301 transformants were constructed in substantial accordance with the teaching of Example 2B. Plasmid DNA was obtained from the E. coli K12 RR1/pTPA301 transformants in substantial accordance with the procedure for plasmid pTPA102 DNA isolation.

E. Construction of a BamHI Recognition Sequence on Plasmid pSV2-dhfr

Ten μg of plasmid pSV2-dhfr (isolated from E. coli K12 HB101/pSV2-dhfr, ATCC 37146) were mixed with 10 μl 10×PvuII salts, 2 μl) (~20 units) PvuII restriction enzyme, and 88 μl of H$_2$O, and the resulting reaction was incubated at 37° C. for two hours. The reaction was terminated by phenol and chloroform extractions, after which the PvuII-digested plasmid pSV2-dhfr DNA was precipitated and collected by centrifugation.

BamHI linkers (5'-CGGATCCCG-3') were kinased and prepared for ligation by the following procedure.

To 1 μg of linker in 5 μl H₂O was added: 10 μl 5×Kinase salts (300 mM Tris-HCl, pH 7.8, 50 mM MgCl₂, 25 mM DTT), 5 μl 5 mM ATP, 5 μl BSA (1 mg/ml), 5 μl 10 mM spermidine, 19 μl H₂O and 1 μl polynucleotide Kinase (10 units/μl). This reaction was then incubated at 37° for 60 minutes and stored at −20° C.

Five μl (∼5 μg) of the PvuII-digested plasmid pSV2-dhfr and 12 μl (∼0.25 μg) of the kinased BamHI linkers were mixed and incubated with 15 μl of H₂O, 2 μl 10×ligase buffer, 10 μl 5 mM ATP, 2 μl BSA (1 mg/ml), 2 μl 10 mM spermidine, and 2 μl T4 DNA ligase (∼2 units), at 16° C. overnight.

Ten μl 10×BamHI reaction buffer, 10 μl (∼150 units) BamHI restriction enzyme, 2 μl BSA (1 mg/ml) and 27 μl of H₂O were added to the reaction, which was then incubated at 37° C. for 3 hours. The reaction was loaded onto a 1% agarose gel, and the desired ∼1.9 kb fragment was isolated in substantial accordance with the teaching of Example 2A. All linker additions performed in these examples were routinely purified on an agarose gel to reduce the likelihood of multiple linker sequences in the resultant vector. The ∼3 μg of fragment obtained were suspended in 10 μl of TE buffer.

F. Ligation

Next, approximately 15 μl (μl μg) of plasmid pTPA301 were digested with BamHI restriction enzyme as taught above. Since there is a unique BamHI site in plasmid pTPA301, this BamHI digestion generates a linear piece of DNA. The BamHI digested pTPA301 was ethanol precipitated and resuspended in 94 μl of dH₂O and phosphatased using 1 unit calf intestinal alkaline phosphotase (Collaborative Research, Inc., 128 Spring Street, Lexington, Mass. 02173), and 5 μl 1M Tris HCl pH 9.0 at 65° for 45 min. The DNA was then phenol: chloroform, chloroform:isoamyl alcohol extracted, ethanol precipitated and resuspended in 20 μl H₂O. Ten μl (∼0.25 μg) of phosphotased pTPA301 was added to 5 μl BamHI-dhfr fragment (∼1.5 μg), 5 μl 10×ligase salts, 5 μl BSA (1 mg/ml)), 10 μl 5 mM ATP, 3 μl T4 ligase, and 12 μl H₂O. This reaction was incubated at 15° C. overnight.

Plasmid pTPA303 was transformed into E. coli K12 RR1 (NRRL B-15210) in substantial accordance with the teaching of Example 2B and the resulting E. coli K12 RR1/pTPA303 transformants were identified by their ampicillin-resistant phenotype and by BamHI-HindIII restriction enzyme analysis of their plasmid DNA. Plasmid pTPA303 was isolated from the transformants in substantial accordance with the procedure of Example 1.

EXAMPLE 9

Construction of Plasmid pBW32

A. Isolation of the ∼2700 bp EcoRI-BglII Fragment of Plasmid pTPA303

About 10 μg of plasmid pTPA303 were digested to completion with 20 units BglII restriction enzyme in 1×BglII buffer (10 mM Tris-HCl pH 7.6, 50 mM NaCl, 10 mM MgCl₂) at 37° C. Tris-HCl concentration was adjusted to 110 mM for digestion with 20 units EcoRI restriction enzyme. The desired fragment was isolated and recovered in substantial accordance with the teaching of Example 4A.

B. Isolation of the ∼2340 bp EcoRI-HindIII Fragment from Plasmid pTPA303

Plasmid pTPA303 was double-digest HindIII and EcoRI restriction enzymes in substantial accordance with the teaching of Example 5A. The ∼2340 bp fragment was isolated and recovered as taught in Example 4A.

C. Isolation of the ∼1990 bp Fragment from Plasmid pTPA303

Plasmid pTPA303 was double digested with HindIII and SstI restriction enzymes in HindIII buffer. The ∼1990 bp fragment was isolated and recovered as taught in Example 4A.

D. Isolation of the ∼680 bp XhoII-SstI Fragment of Plasmid pBW28

About 10 μg of plasmid pBW28 were digested with XhoII enzyme to completion in XhoII buffer. The reaction was heated to 65° C. for 10 minutes to heat inactivate the enzyme and then the DNA was recovered by ethanol precipitation. The DNA was subsequently digested with SstI enzyme to completion. The desired fragment was isolated and recovered as taught in Example 4A.

E. Ligation and Transformation of E. coli MM294

About 0.1 μg each of the above fragments described in A through D were ligated in substantial accordance with the teaching of Example 4C. The ligation mix was used to transform E. coli MM294 as taught in Example 4D. Transformants were identified by their ampicillin resistant phenotype and restriction analysis of plasmid DNA.

EXAMPLE 10

Construction of CHO K1/BW32 Transformants

A. Preparation of the Cells

A culture of a Chinese hamster ovary (CHO) K1 cell line DXB11 which is dihydrofolate reductase negative (dhfr-) was used in this example. Such dhfr-CHO K1 host cells can be generated from ATCC #CCL 61 in accordance with the procedure disclosed in Urlaub and Chasin, 1980, Proc. Natl. Acad. Sci., U.S.A. 77:4216. These cells were passaged one to two days prior to the transformation, so as to provide 40–50% confluency on the day of transformation. The media was changed two to three hours before the transformation. Two 100 mm petri dishes of cells are needed for each transformation.

B. Preparation of the DNA

Plasmid DNA was transformed into CHO DXB11 cells using a calicium phosphate technique. One to two μg of plasmid pBW32 plus 18 μg Salmon sperm DNA was added to 62.5 μl of 2M CaCl₂ and 437.5 μl of H₂O. The 0.5 ml of DNA were then added dropwise to 0.5 ml of 2×HEBS (10 g/l Hepes, pH=7.5; 16 g/l dextrose), forming a milky precipitate. The mixture was allowed to stand 10–20 minutes at room temperature before it was added to the cells. A longer incubation time may result in a coarser precipitate that does not transform well, but sometimes a longer incubation may be necessary to form a precipitate. DNA can also be prepared and transformed into mammalian cells using an DEAE-Dextran technique (McCutchan and Pagano, 1968 J. Natl. Cancer Inst. 41:351) or electroporation (Potteretal, 1984 Proc. Natl. Acad. Sci., USA 81:7161) or DNA can be microinjected. The above described transformation is not limited to this calcium phosphate technique.

C. Transformation of the Cells

The 1 ml DNA solution prepared in Example 9B was added to a 100 mm petri dish of CHO (DXB11) cells with gentle agitation and incubated at 37° for 3-4 hours in a $CO_2$ incubator. Using care not to detach the cells, the cells were washed twice with serum-free growth media (Dulbecco's Modified Eagle Medium, Gibco). One ml of HEBS with 15% glycerol was added to the cells, which were then incubated at 37° for two minutes.

The "glycerol-shock" incubation was terminated by the addition of serum-free growth media, followed by two washes with serum-free growth media. Complete fresh growth media containing serum was then added, and the cells were returned to a 37° incubation.

Transformants were exposed to selection media depleted of hypoxanthine and thymidine in the presence of methotrexate (MTX). A transformant; clone 3, isolated in 25 nM, was found to produce 3.8 units mt-PA/ml whereas transformant pBW32-9 isolated in 50 nM MTX synthesized ~15-20 units mt-PA/ml. Similarly isolated CHO/pBW32 transformants express more mt-PA because more copies of the recombinant mt-PA gene are present due to the amplification of the recombinant DNA. This amplification is well known in the art (see U.S. Pat. No. 3,399,216, issued 8/16/83) and is accomplished by exposing the host cells transformed with a plasmid comprising a wild-type dhfr gene to increasing amounts of methotrexate. This methotrexate-mediated amplification can be accomplished in a wide variety of host cells and is not limited to dhfr- cell lines (Deschatrette et al., 1985, Proc. Natl. Acad. Sci., U.S.A. 82:765).

EXAMPLE 11

Inhibition of t-PA and Modified t-PA by Preparations of Plasminogen Activator Inhibitor To prepare a crude fraction containing high levels of plasminogen activator inhibitor, two units of fresh human platelet concentrates were obtained from the local blood bank. The platelet concentrates were centrifuged 2,000 rpm for 25 minutes at 20° C. The supernatants were decanted and the platelet pellets resuspended, washed, recentrifuged, washed again and recentrifuged in the original platelet concentrate volume (70 ml per unit) in acid citrate dextrose. The washed platelets were resuspended in a modified Tyrode's buffer containing no $Ca^{2+}$ or $Mg2+$ but $Na_3$ citrate to a final concentration of 0.38%. The combined platelet pellets were suspended in a final volume of 50 ml of the above buffer. A 3.33 ml aliquot of bovine fibrinogen (Miles) (20.62 mg/ml) rendered plasminogen-free through lysine-sepharose affinity chromatography was added to the platelet suspension. $CaCl_2$ was added to 1/40M and the platelet suspension activated with 400 μg/ml of adenosine 5′ diphosphate and a total of 1 mg of platelet activating factor (1-0-alkyl-2-acetyl-sn-glyceryl-3-phosphorylcholine). The activated platelets were left overnight in the cold, centrifuged at 5,000×g at 4° C. for 10 minutes and the cell-free supernatant used for further experiments. To determine the interactions between this crude human platelet derived inhibitory material and authentic t-PA as well as modified t-PA, the following methodology was utilized. Plasminogen-free bovine fibrinogen, further treated by Trasylol (Aprotinin) affinity chromatography to remove trace quantities of an unidentified serine protease was added to 50 μg/well to ninety-six well microtiter plates. The wells containing fibrinogen in solution were dried overnight in the laminar flow hood. Human plasminogen or plasmin-free thrombin (2800 NIH units/mg) was then added to the wells to a final concentration of 0.5 units of thrombin/well. After 4 hours incubation, the wells were washed extensively with phosphate-saline-gelatin buffer (0.02 M $PO_4$, 0.15 M NaCl, 0.25% gelatin, 0.01% Tween 80, pH 7.4) and the following reagents added to individual wells: highly purified authentic t-PA derived from the conditioned media of human Bowes melanoma cells in culture (specific activity approximately 100,000 International UK units/ml), modified t-PA contained in the conditioned tissue culture medium from clone 3 (see example 10) dialyzed extensively against 0.03M Tris, 0.15M NaCl, Tween 80, 0.01%, pH 7.4 (Tris saline buffer) diluted 1:2 in Tris saline buffer, human plasminogen from Behring (specific activity 20 I.U./mg) from which trace plasmin impurities had been removed by Trasylol (Aprotinin) affinity chromatography, 5 or 10 ul of the crude plasminogen activator inhibitor preparation, the synthetic paranitroanilide tripeptide substrate S-2251 (H-D-val-leu-lys-pNA, HCl) (Kabi), and Tris saline buffer. The following volumes of the following solutions were used: plasminogen (1 IU/ml), 20 ul: authentic t-PA (2 units/ml), 10 ul; clone 3 conditioned medium diluted 1:2 (approximately 2 units/ml) 10 ul; S-2251, 3 mM, 90 ul and Tris saline buffer to a total volume of 200 ul/well. The microtiter plates were read in a plate reader at times 0, 60, and 120 minutes, and A405 nm between the 1 and 2 hour readings used for calculations.

On a percentile basis, 5 ul of platelet-derived inhibitor inhibited t-PA 74%, 10 ul inhibited 87.5%. In contrast, 5 ul of platelet-derived plasminogen activator inhibitor inhibited modified t-PA 20% and 10 ul inhibited modified t-PA 45.3%. These experiments demonstrate that this crude human plasminogen activator inhibitor effectively inhibits authentic t-PA but is an inefficient inhibitor of the modified form of the enzyme.

EXAMPLE 12

Demonstration of Modified t-PA Fibrin-Dependent Plasminogen Activation

Figure 14:
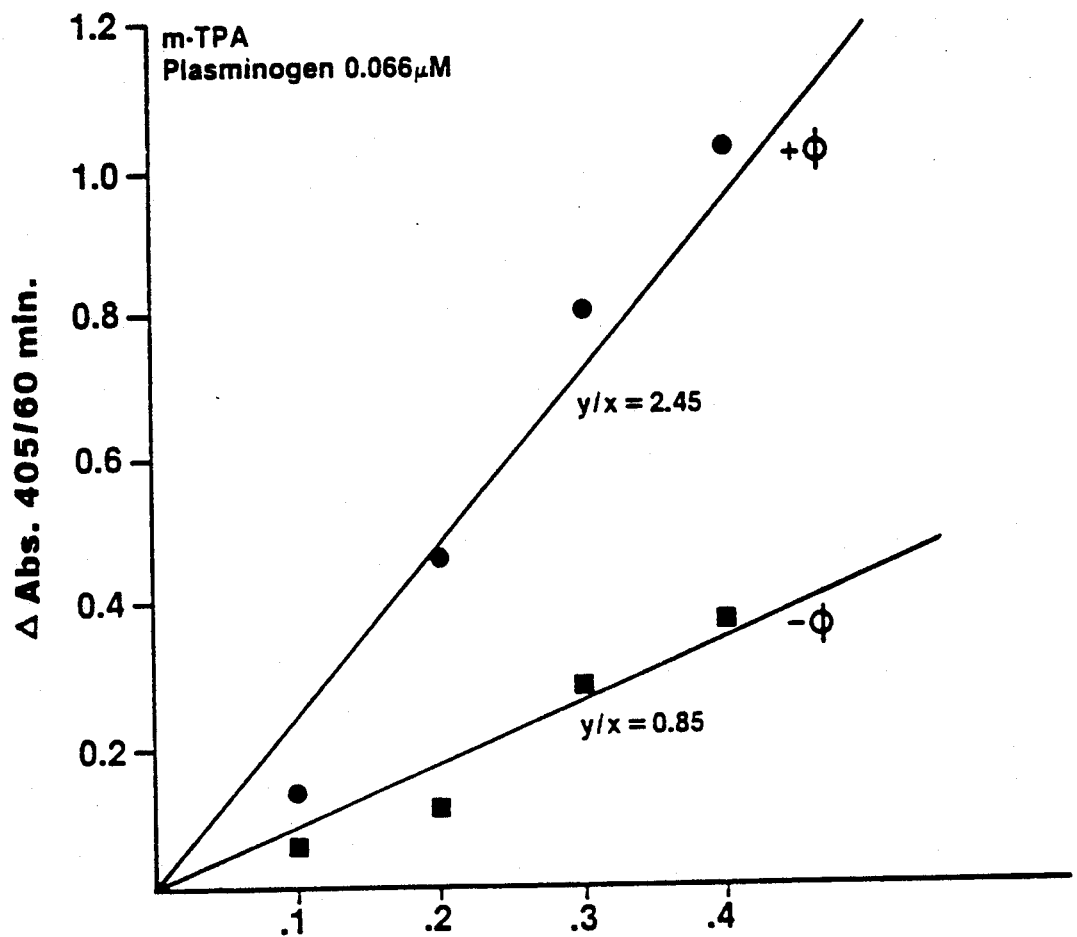
FIG. 14 displays $A_{405nm}$ values reflecting the rate of plasminogen activation as a function of the concentration of native t-PA or mt-PA in the presence or absence of fibrin.
Figure 14A:
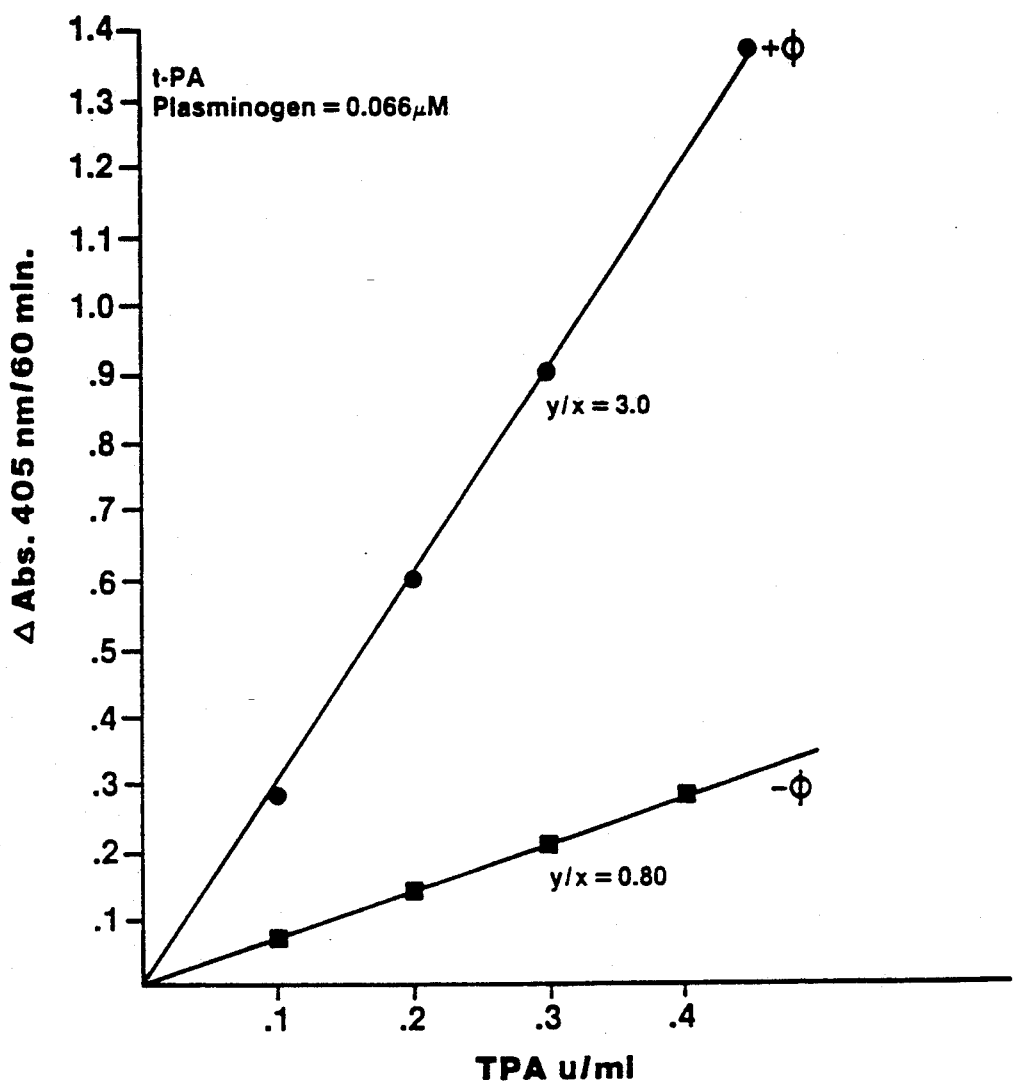

To determine rates of plasminogen activation by t-PA and mt-PA in the presence and absence of fibrin, the following reagents were prepared. Highly purified authentic t-PA derived from the conditioned media of human Bowes melanoma cells (specific activity approximately 100,000 UK units/ml), modified t-PA contained in the conditioned tissue culture medium from clone 3 (see example 10), dialyzed extensively against 0.03M Tris, 0.15M NaCl, Tween 80 0.01%, pH 7 (Tris saline buffer), human plasminogen from Behring (specific activity 20 IU/mg) from which trace plasmin impurities had been removed by Trasylol (Aprotinin) affinity chromatography, plasminogen-free fibrinogen fragmented by CnBr treatment as a soluble substitute for fibrin, the synthetic paranitroanilide tripeptide substrate, S-2251 (H-D-val-leu-lys-pNA, HCl) (Kabi) and Tris saline buffer. The following volumes of the following solutions were admixed in disposable plastic cuvettes (1 cm light path length): plasminogen 10 IU/ml of Tris saline buffer, 10 ul; authentic t-PA 1 unit/ml Tris saline buffer, 100, 200, 300 or 400 ul; dialyzed clone 3 material (mt-PA) 1.46 units/ml, 100, 200, 300 or 400 ul/ml, CnBr fragmented fibrinogen 20 ul (where appropriate) and S-2251 3.525 mM in Tris saline buffer, 175 ul and Tris saline buffer to a total volume of 1 ml. $A_{405nm}$ readings were obtained at 30, 60, 120 and 150 minutes. FIG. 14 displa A405nm values reflecting the rate of plasminogen activation as a function of the concentration of native t-PA or mt-PA in the presence and absence of fibrin (CnBr fibrinogen). A linear relationship exists in both instances and the rate of plasminogen activation with mt-PA resembles the rates for inactive t-PA in that both reactions are greatly enhanced in a fibrin containing system as opposed to a system where fibrin is absent. From this data, rate constants for t-PA and mt-PA activation of plasminogen in the presence and absence, of fibrin can be derived as outlined by Rånby and Wallén, 1981, *Prog. Fibrinolysis* 5:233. In this system two reactions occur simultaneously, the conversion of plasminogen to plasmin by t-PA and the hydrolysis of S-2251 by plasmin as described in equations 1 and 2 below:

$$d[Plasmin]/dt = K_1[t\text{-}PA]$$

$$d[pNA]/dt = K_2[Plasmin]$$

Where $K_1$ is the rate constant for the conversion of plasminogen to plasmin by t-PA and $K_2$ is the rate constant for plasmin mediated hydrolysis of the tripeptide pNA substrate. $K_2$ is known from the literature and has been reported to be $17.0 M^{-1} s^{-1}$ for 0.3 mM of S-2251. (Christensen and Ipsen, 1979, *Biochem. Biophys. Acta* 567:177). Since S-2251 is specific for plasmin and not hydrolyzed by t-PA, equations 1 and 2 can be combined to provide equation 3:

$$A_{405} = A_{405} + \epsilon_{405} K_2[Plasmin]t°$$

$$+ \epsilon_{405} K_1 K_2 [t\text{-}PA]^2$$

Where $A_{405}$ is absorption at time 0, $A_{405}$ is absorption at time X of incubation, $\epsilon_{405}$ is the molar extinction coefficient for PNA at pH 7.4 which was experimentally established to be 10,500, t° is time 0 and t is time of incubation. Equation 3 can be rearranged to provide equation 4:

$$\Delta A_{405} = 0.5 \epsilon_{405} K_1 K_2 [t\text{-}PA] t^2$$

from which $K_1$ or the rate constants for plasminogen activation by natural and modified t-PA in the presence and absence of fibrin can be calculated. Table 1 provides these rate constants which are derived from experiments in which natural t-PA and mt-PA were added to the reaction mixtures at 100 ul. These experiments demonstrate that mt-PA contained in dialyzed conditioned medium from CHO cells expressing and secreting this mutant protein has preserved its fibrin dependence and kinetically resembles natural t-PA very closely.

TABLE 1

| Rate Constants, $K_1$ ($M^{-1}s^{-1}$) | |
|---|---|
| t-PA +F | 0.012 |
| t-PA −F | 0.0045 |
| mt-PA +F | 0.013 |
| mt-PA −F | 0.0047 |

EXAMPLE 13

Determination of Natural t-PA and mt-PA $M_r$ by SDS PAGE and PA Activity Measurements To determine the $M_r$ of the recombinant mt-PA contained in conditioned medium from clone 3 and compare it to the $M_r$ of authentic full-length t-PA, the following experimental conditions were used.

Figure 15:
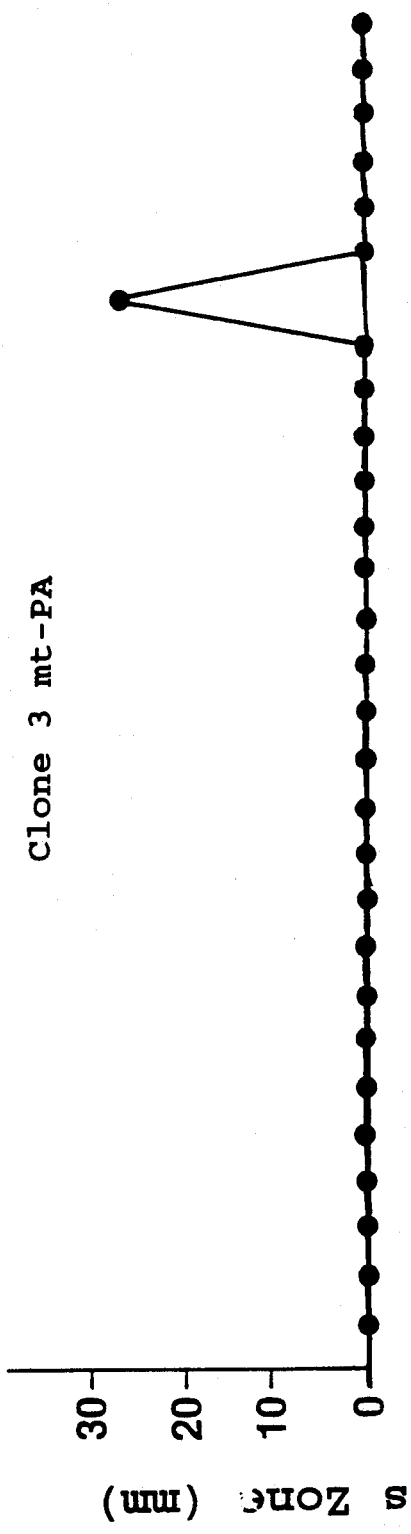
FIG. 15 plots the diameter of lysis zones in mm against gel slice number to determine the molecular weight ($M_r$) by PA activity measurement.
Figure 15:
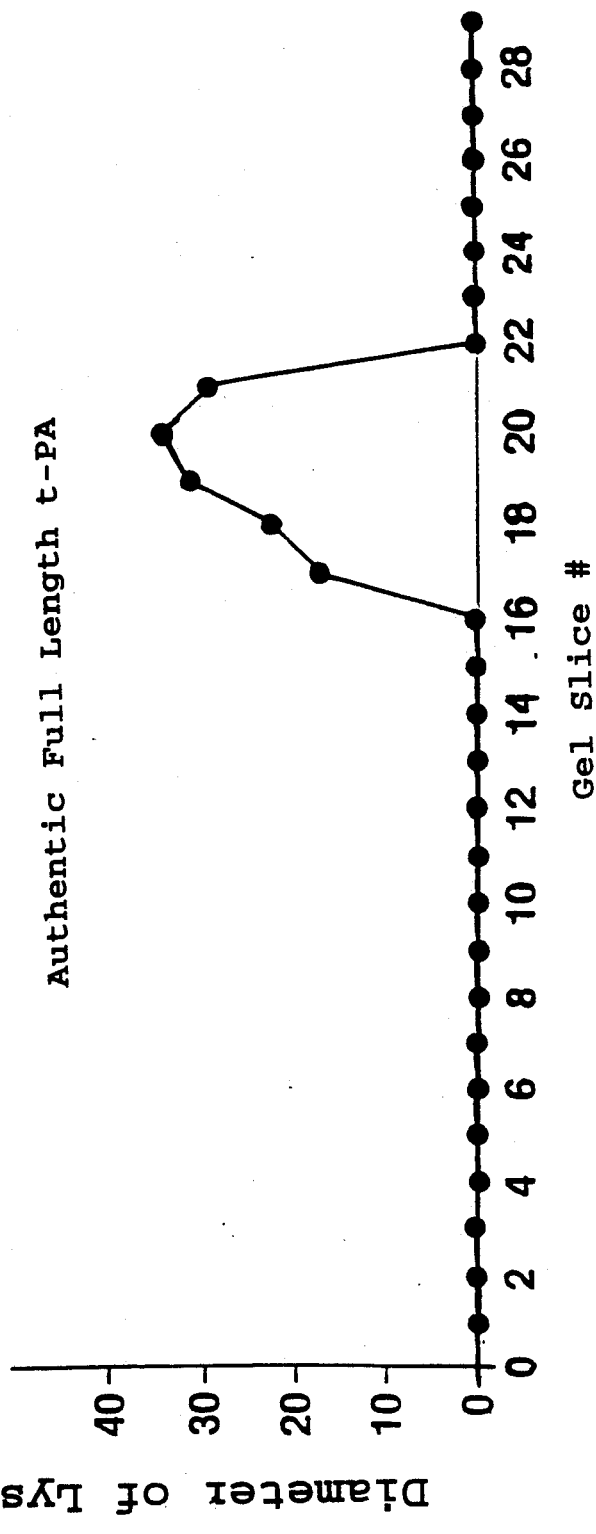
Figure 16:
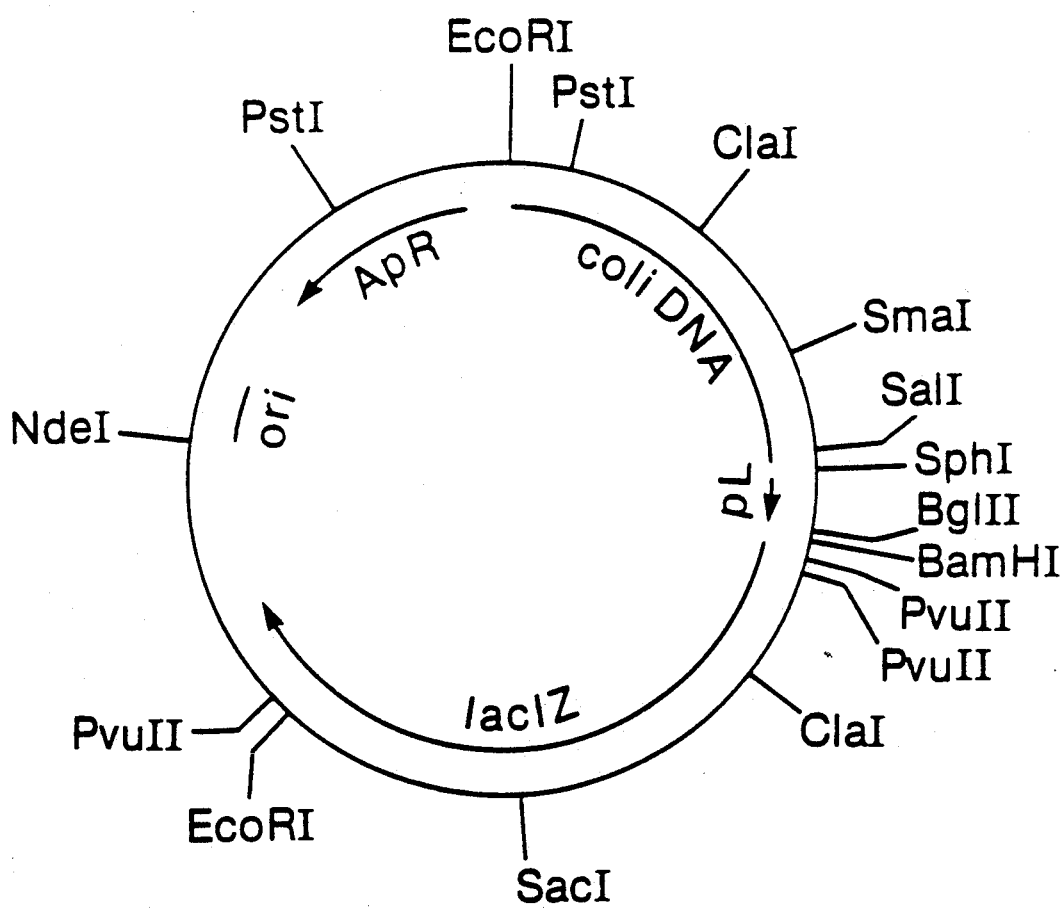
FIG. 16 is a restriction site and function map of plasmid pKC283.
Figure 17:
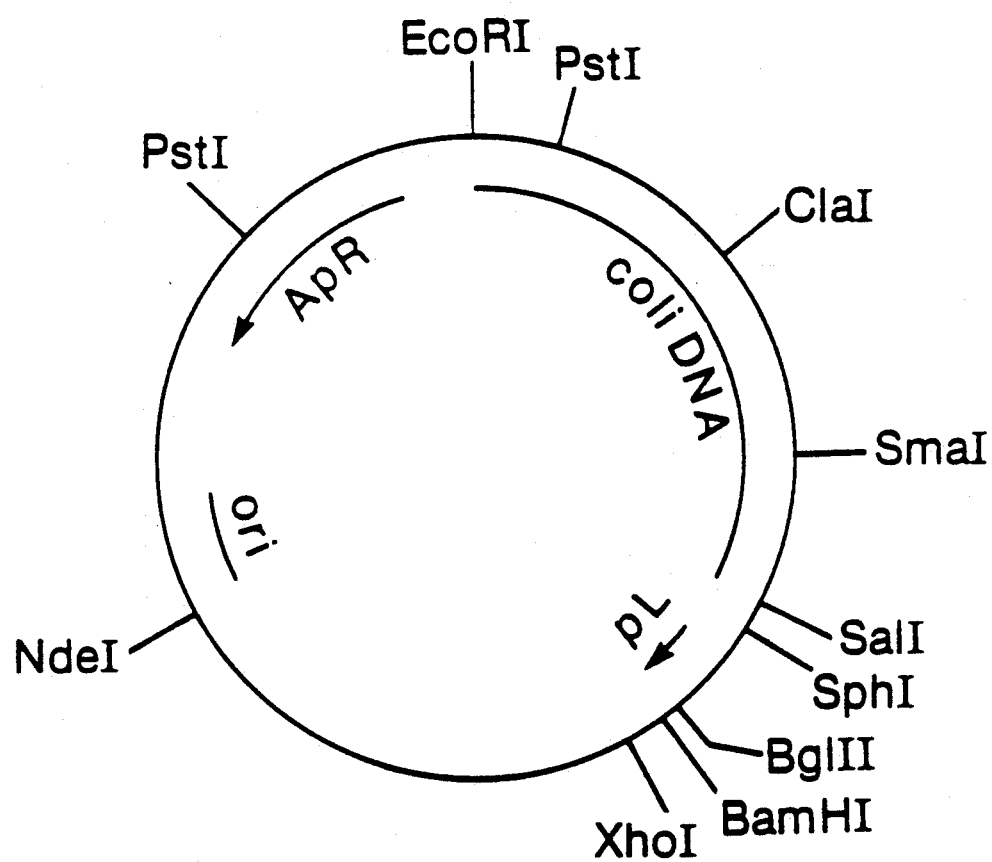
FIG. 17 is a restriction site and function map of plasmid pKC283PX.
Figure 18:
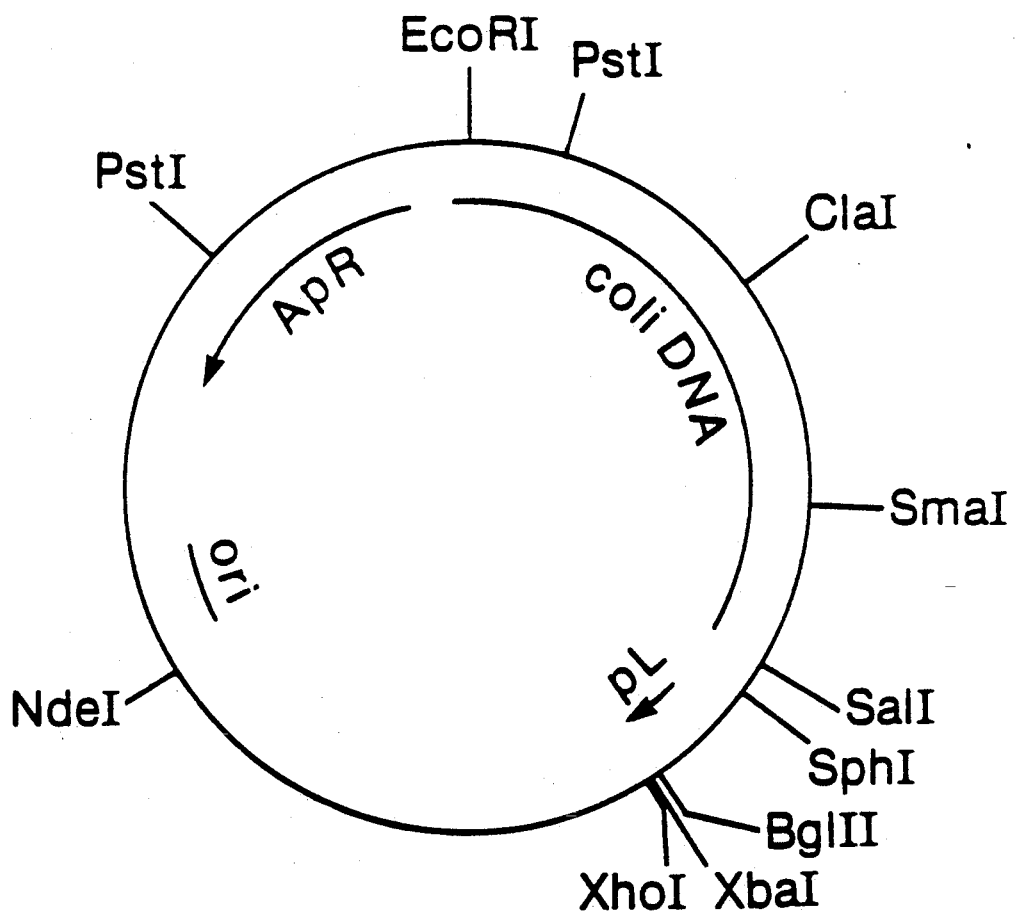
FIG. 18 is a restriction site and function map of plasmid pKC283-L.
Figure 19:
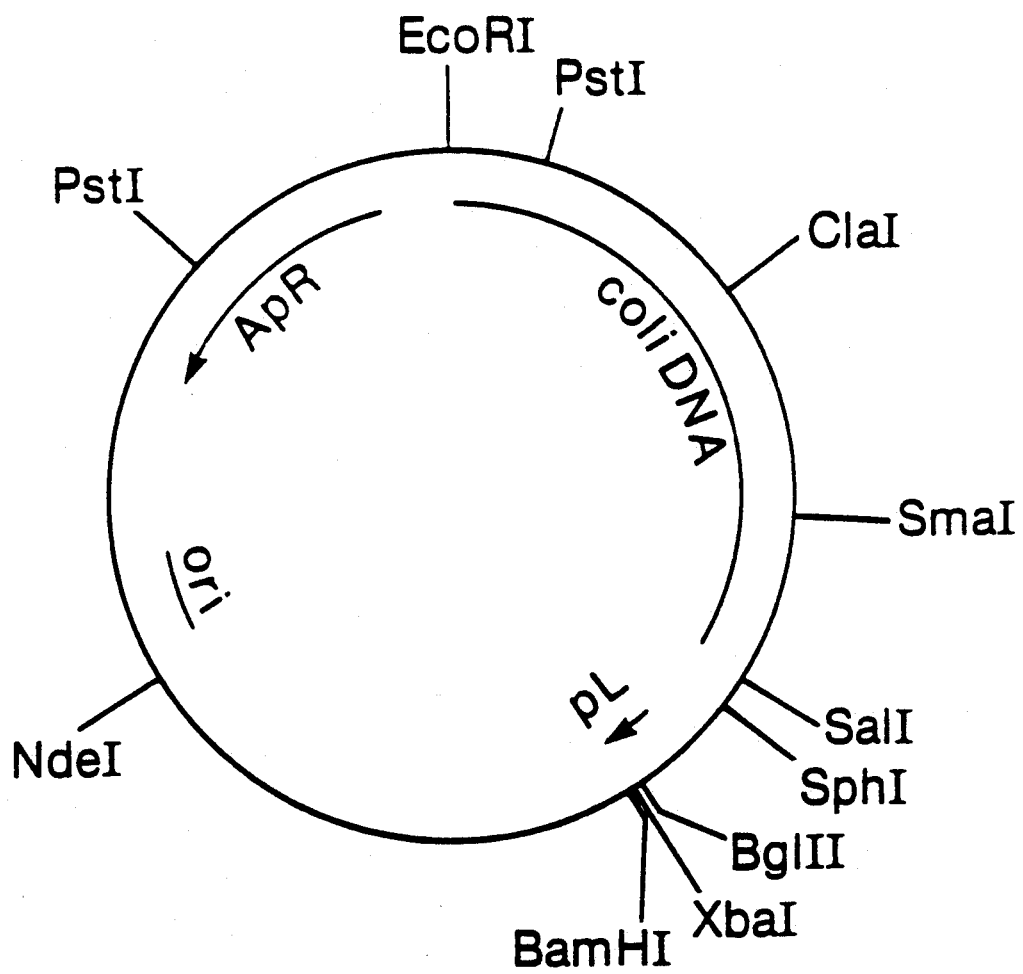
FIG. 19 is a restriction site and function map of plasmid pKC283-LB.
Figure 20:
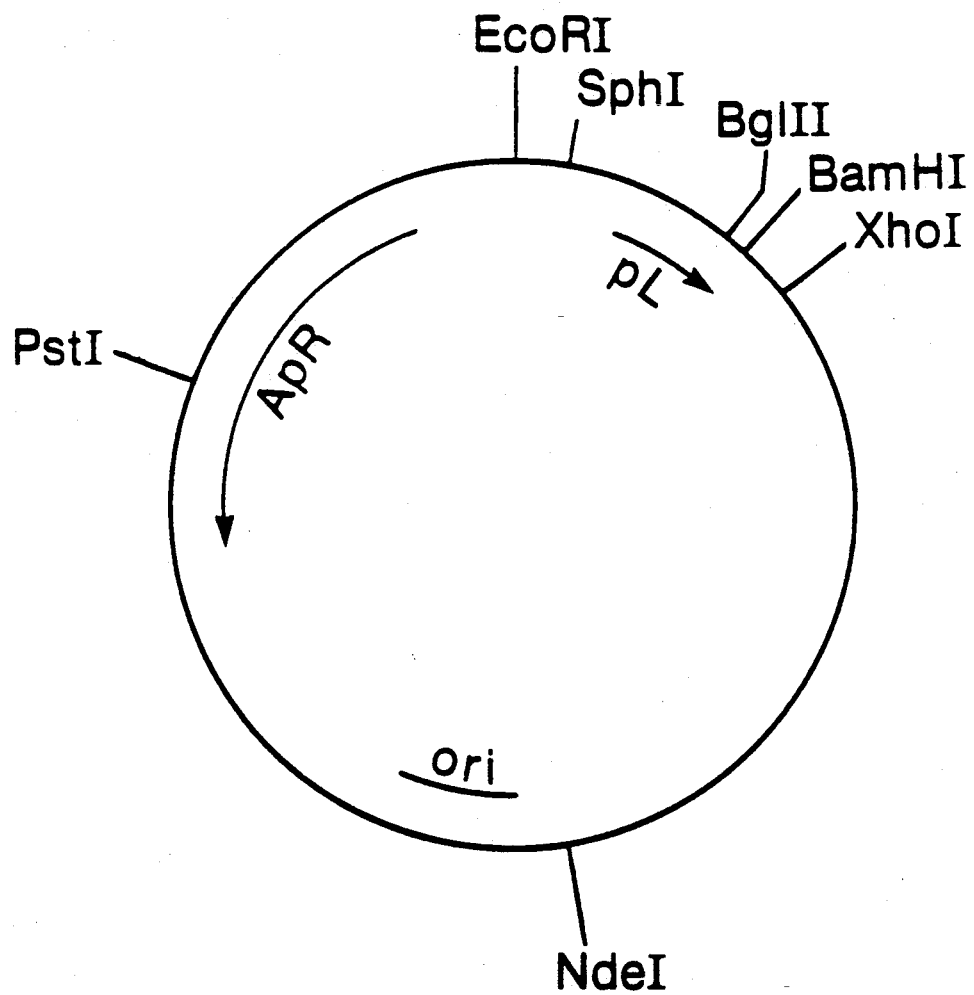
FIG. 20 is a restriction site and function map of plasmid pKC283PRS.
Figure 21:
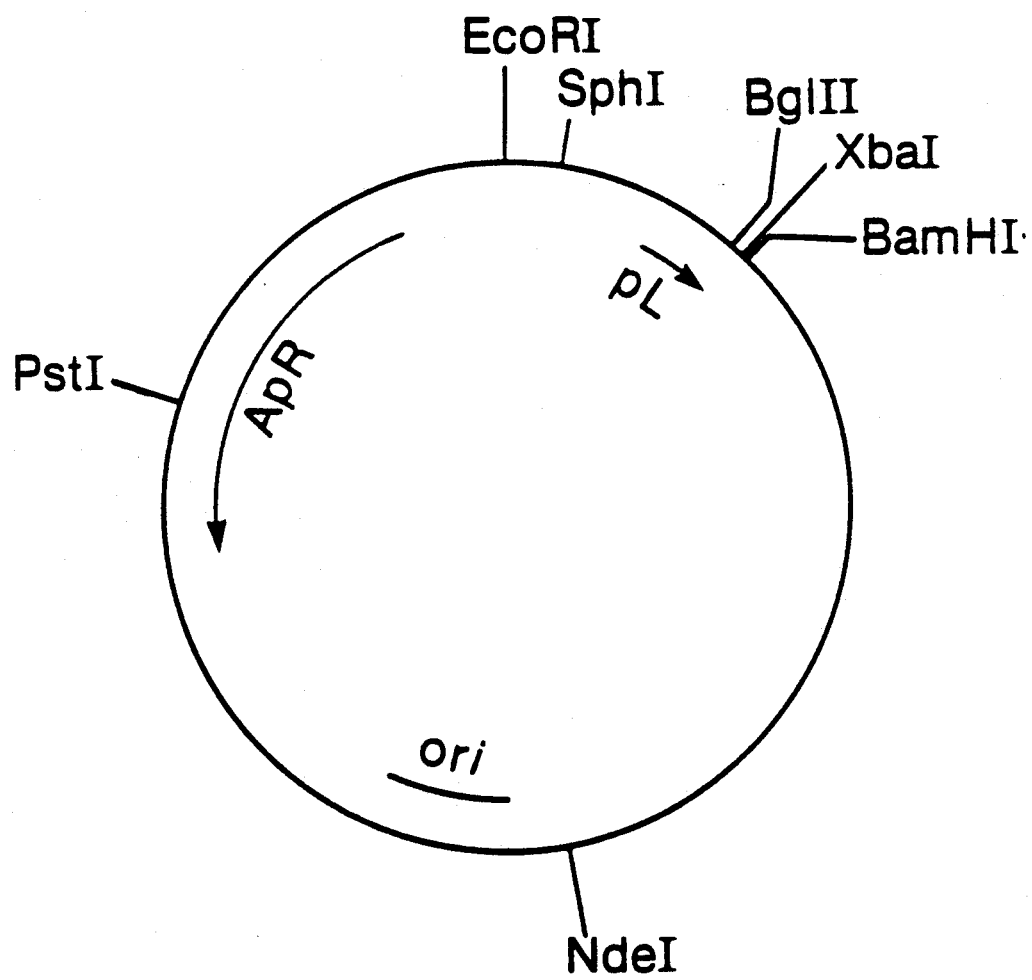
FIG. 21 is a restriction site and function map of plasmid pL32.
Figure 22:
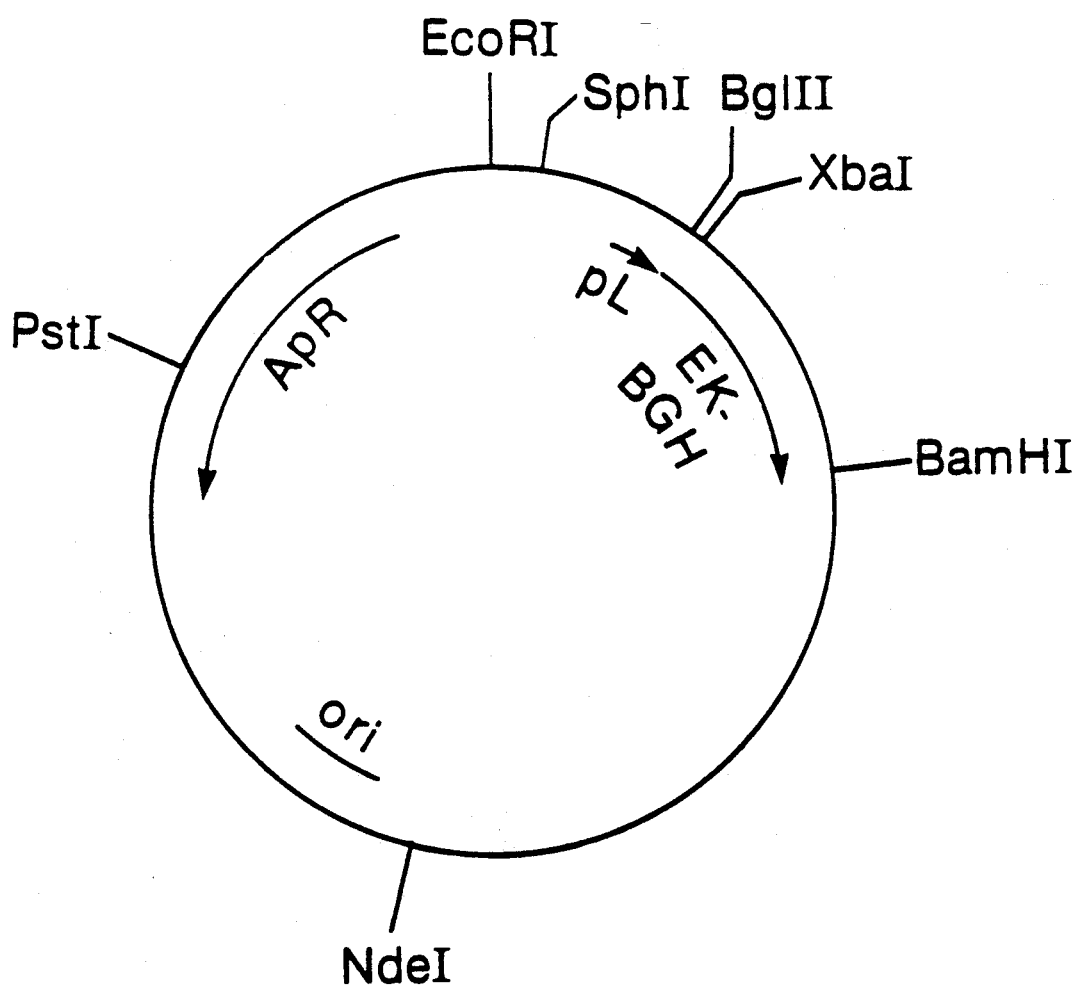
FIG. 22 is a restriction site and function map of plasmid pL47.
Figure 23:
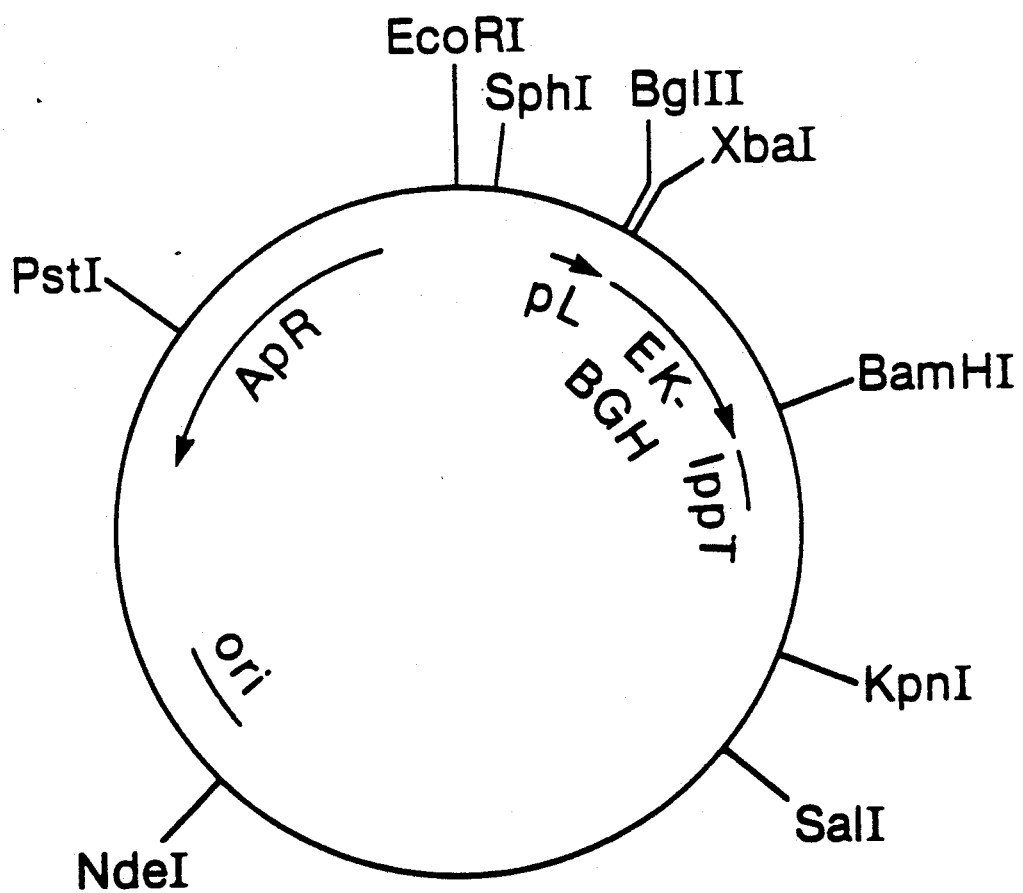
FIG. 23 is a restriction site and function map of plasmid pL84.
Figure 24:
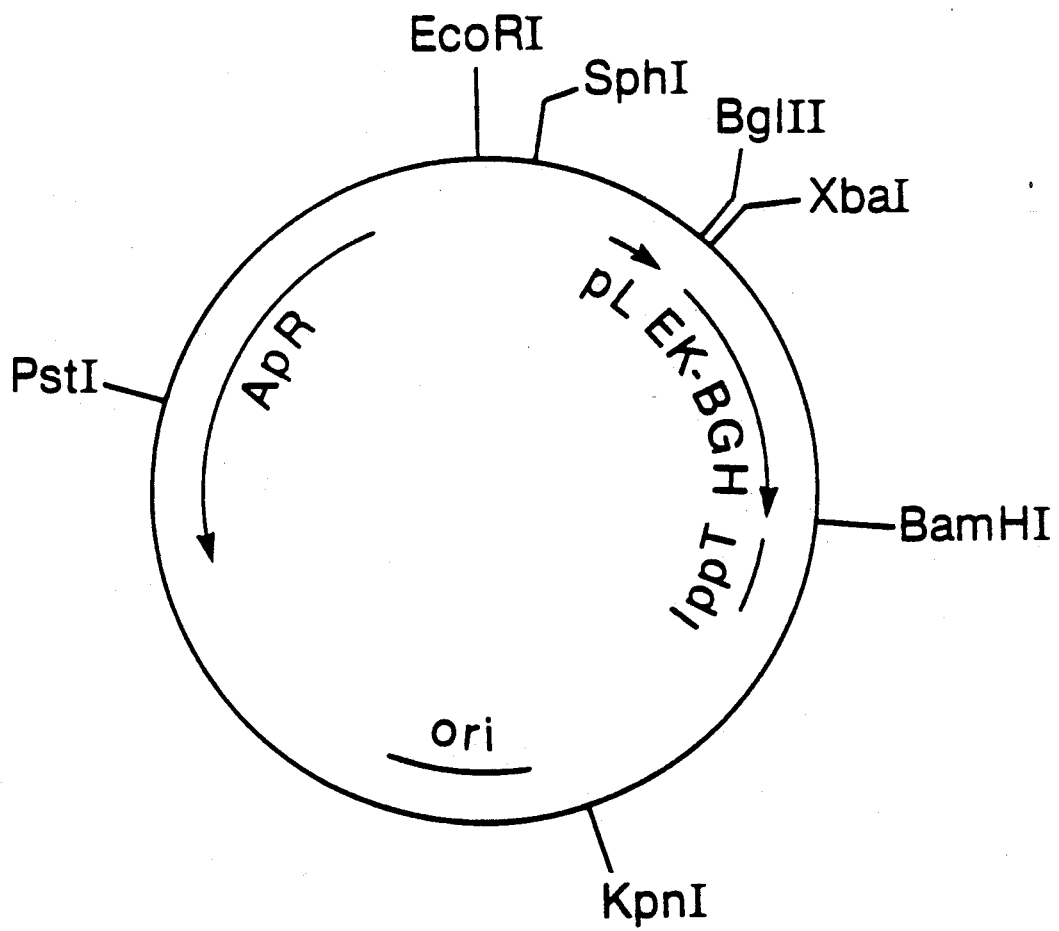
FIG. 24 is a restriction site and function map of plasmid pL95.
Figure 25:
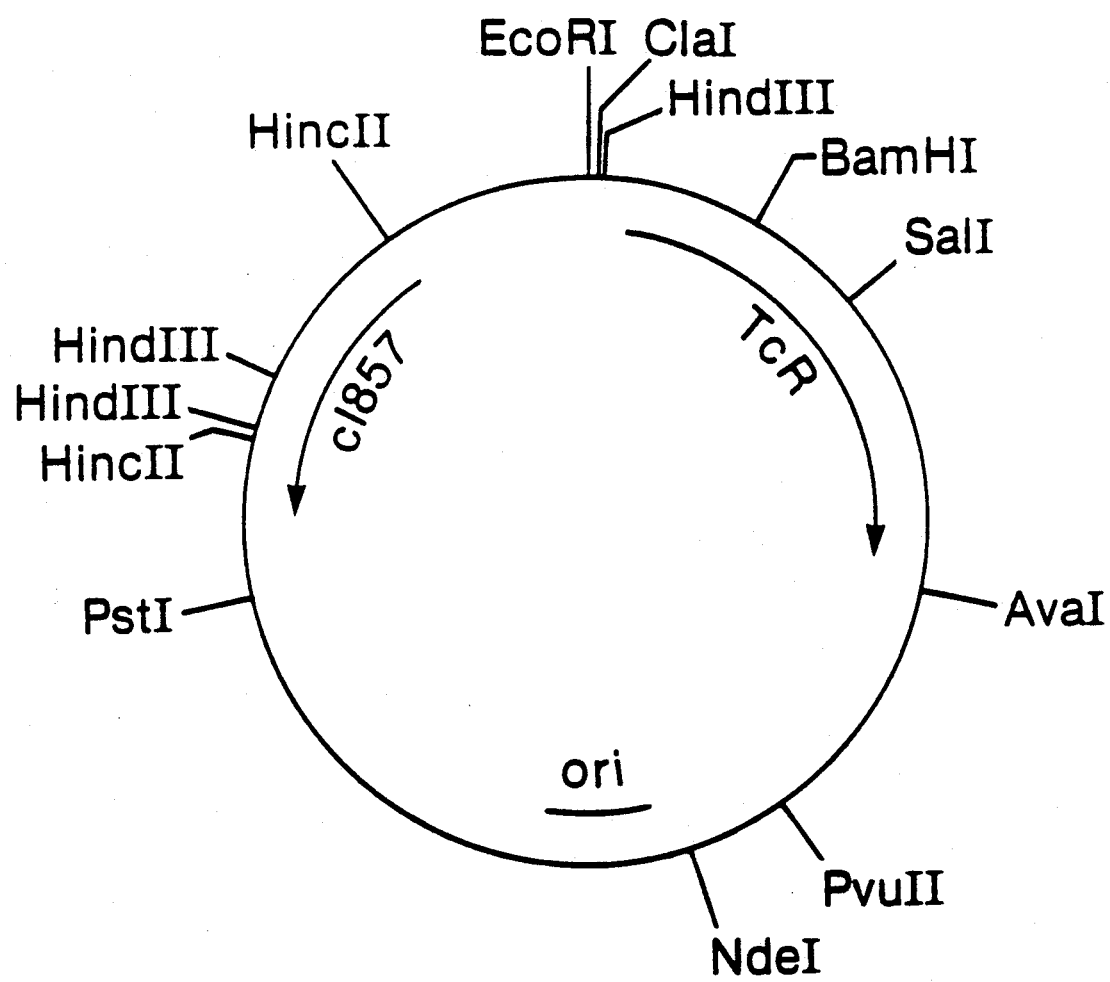
FIG. 25 is a restriction site and function map of plasmid pPR12.
Figure 26:
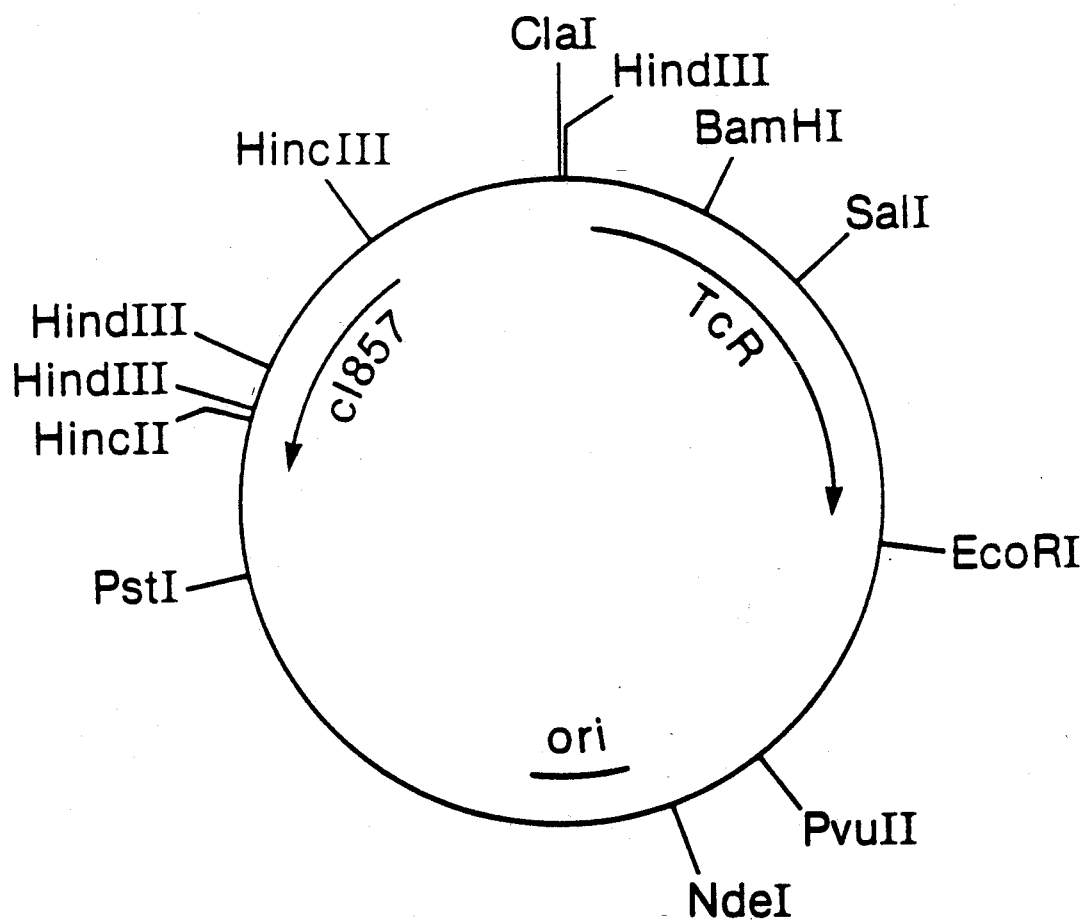
FIG. 26 is a restriction site and function map of plasmid pPR12AR1.
Figure 27:
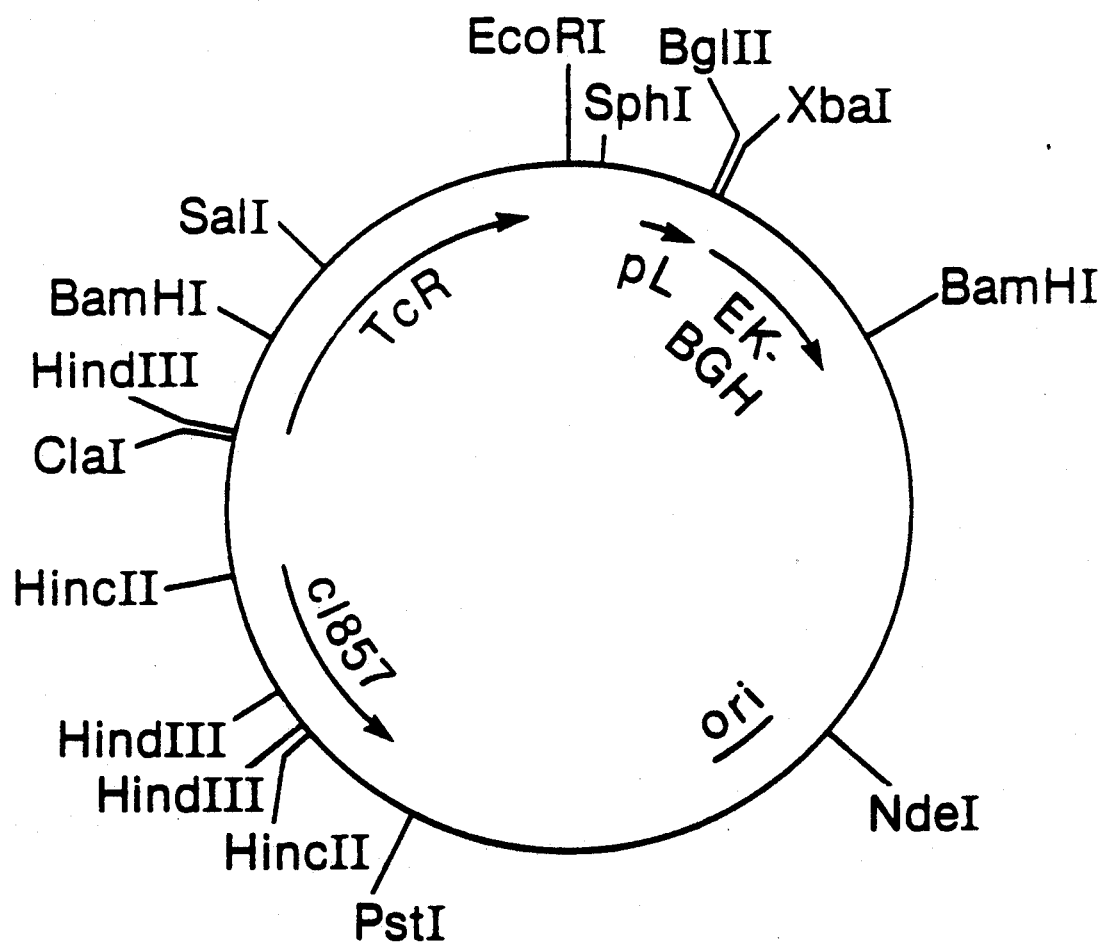
FIG. 27 is a restriction site and function map of plasmid pL110.
Figure 28:
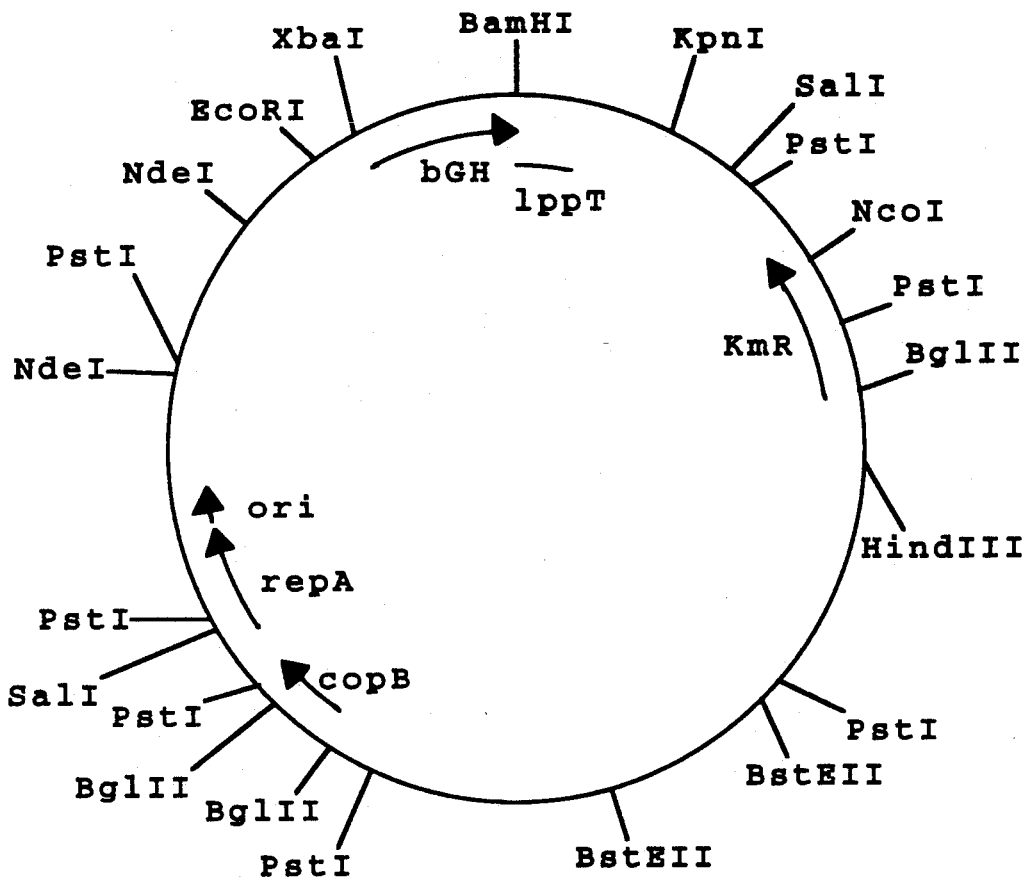
FIG. 28 is a restriction site and function map of plasmid pCC101, also referred to as pCZ101.

Clone 3 mt-PA conditioned medium was extensively dialyzed against 0.03M Tris, 0.15 M NaCl, 0.01% Tris, pH 7.4 and adjusted to 1.4 units/ml. Highly purified native human t-PA derived from the conditioned media of Bowes melanoma cells in culture was diluted in the same Tris saline buffer to a final concentration of 2.5 units/ml. About 200 ul of sample was applied to 6 cm SDS PAGE tube gels prepared according to Laemmli (1971) (2.0% stacking gels, 8.5% running gels, non-reducing conditions). After electrophoretical separation, the tube gels were placed in a 1.5% solution of Triton X-100, soaked for 45 minutes, transferred to another bath of Triton X-100 and soaked for an additional 45 minutes. The Triton treated gels were snap-frozen, kept at −20° C. overnight and sliced into 2 mm slices the following morning. Each slice was placed on standard fibrin plates and incubated for 96 hours. At this time, the circular zones of lysis around the gel slices were measured. FIG. 15 plots the diameter of lysis zones in mm against gel slice number. The peak fibronolytic activity for melanoma-derived natural t-PA is in slice 20 and the peak of activity is clone 3 mt-PA is in slice 23. When migration of protein in these peak slices was compared to the migration of marker proteins in separate Coomassie blue stain gels, the calculated $M_r$ for t-PA was approximately 64 kd and the value for clone 3 mt-PA approximately 38 kd.

EXAMPLE 14

Construction of Plasmid pBW33

A. ClaI Partial Digest of Plasmid pBW28

About 10 μg of plasmid pBW28 were diluted into 100 μl ClaI buffer (10 mM Tris-HCl pH 7.9, 10 mM MgCl$_2$, 50 mM NaCl) in each of 3 tubes. Five units of ClaI restriction enzyme was added to each tube and incubations at 37° C. done for 30 seconds, 1 minute, and 2 minutes, respectively. Reactions were stopped by the addition of EDTA to 25 mM. After chloroform extraction, the DNA was ethanol precipitated.

B. Klenow Blunting of ClaI Ends

ClaI digests of pBW28 described in 14A were blunted by 4.5 units Klenow per sample in 50 mM Tris-HCl pH 7.6, 10 mM MgCl$_2$, 250 mM dATP, 250 mM dGTP, 250 mM dCTP, 250 mM TTP. The reaction was incubated at 20° C. for 30 minutes, then stopped by heat inactivation of the enzyme. The DNA was recovered by ethanol precipitation.

The DNA was run on a 0.6% low-gelling-temperature agarose (Sea Plaque, FMC Corp., Marine Colloids, Rockland, Me. 04841) gel for 2-3 hours at ~130V and ~75 mA. The gel was stained in a dilute solution of ethidium bromide, and the bands visualized under long wave UV light. The largest linear band, which was cut at only one of the two ClaI sites present on the plasmid DNA, was excised. The bands from all three samples were pooled and the DNA religated in substantial accordance with *Methods In Enzymology* 101:85 (Academic Press, Wu and Grossman, Eds.) except that the procedure was scaled down to 100 μl

C. Transformation of *E. coli* MM294

Competent *E. coli* MM294 were prepared and transformed with the ligation mix as taught in Example 4D except that 0.3 mls competent cells were used per 100 μl ligation mix and the procedure was scaled up accordingly. Transformants were identified by their tetracycline resistant phenotype and restriction digest analysis of plasmid DNA. The sequence of pBW33 differs from that of pBW28 as shown below.

```
   XbaI                                      1         2
5'-CTAGAGGGTATTAATAATGTATCGCGATTTAAATAAGGAGGAATAACA-3'
   ||||||||||||||||||||||||||||||||||||||||||||||||
3'-    TCCCATAATTATTACATAGCGCTAAATTATTCCTCCTTATTGTAT-5'
                                                  NdeI
```

The insertion of two bases in the cistron changes the phasing so that stop 2 is used in pBW33 rather than stop 1 used in pBW28.

EXAMPLE 15

Construction of Plasmid pBW35

A. Isolation of the 6.4 kb XbaI-SstI Fragment from pBW28

Plasmid pBW28 was digested with SstI restriction enzyme to completion. Buffer conditions were adjusted and the DNA was further digested to completion with XbaI. DNA was concentrated by ethanol precipitation and the 6.4 kb fragment was isolated and recovered as taught in Example 4A.

B. Isolation of the ~700 bp SstI-NdeI Fragment from Plasmid pBW28

Digestion and isolation of this fragment was performed as described in Example 15A except that NdeI restriction enzyme was substituted for XbaI.

C. Construction of XbaI-NdeI Linker

The following linker was synthesized:

```
   XbaI
5'-CTAGAGGGTATTAAA-3'
   |||||||||||||
3'-    TCCCATAATTTAT-5'
```

After synthesis, 200 pmols of each linker were kinased in 20 μl reactions containing 50 mM Tris-HCl pH 7.6, 10 mM MgCl₂, 10 mM dithiothreitol, 2 nmols ATP, 50 μCi γ³²P-ATP (NEN) and 11 Richardson units T4 polynucleotide kinase for 30 minutes at 37° C. The enzyme addition and incubation steps were repeated. The reaction was terminated by heat inactivation of the enzyme at 70° C. for 10 minutes. Kination efficiency was verified by descending paper chromatography on DE81 paper in 0.35M ammonium formate.

Following kination, aliquots from each kination reaction were mixed, heated at 90° C for 2 minutes and slow cooled in the water bath for 5 hours to room temperature to allow for annealing of strands.

D. Ligation and Transformation into *E. coli* MM294

The fragments and linker described above were ligated in substantial accordance with the teaching of Example 14B using 50 pmols annealed linker in a 100 μl reaction. *E. coli* MM294 was transformed with the ligated material as taught in Example 14C. Transformants were identified by their tetracycline resistant phenotype and restriction digest analysis of plasmid DNA. Although the linker will ligate with another NdeI-digested fragment, the NdeI restriction site will not be regenerated upon ligation. Thus, plasmid pBW35 does not contain an NdeI site common to both plasmids pBW33 and pBW36.

EXAMPLE 16

Construction of Plasmid pBW36

Plasmid pBW36 was constructed exactly as that taught for plasmid pBW35 except that the following linker was substituted for the linker identified in Example 15C:

```
5'-CTAGAGGGTATTACA-3'
   |||||||||||||
3'-    TCCCATAATGTAT-5'
                NdeI
```

EXAMPLE 17

Transformation of *E. coli* K12 RV308

About 0.1 μg each of plasmid pBW33, pBW35, and pBW36 DNA were transformed into *E. coli* RV308 in substantial accordance with the teaching of Example 2B, except that the competent cells were stored in 20% glycerol at −90° C. prior to transformation.

The transformants were identified by their tetracycline resistant phenotype and by restriction enzyme analysis of plasmid DNA. The resultant cells were used to isolate their respective plasmid DNA in substantial accordance with the procedure of Example 1.

EXAMPLE 18

Construction of Runaway Replicon-containing Plasmids

A. Isolation of a Runaway Replicon-containing Fragment

Plasmid pCZ106 (NRRL B-15959) is double-digested with the restriction enzymes EcoRI and BamHI in substantial accordance with the teaching of Example 7A. The desired ~10 kb EcoRI-BamHI vector fragment can be isolated in accordance with the teaching of Example 4A.

B. Isolation of the Promoter-Containing Fragment

Plasmid pL110 is double-digested with EcoRI and XbaI restriction enzymes. The desired ~1.9 kb fragment can be isolated and recovered as taught in Example 7B.

C. Isolation of the ~1.3 kb XbaI-BamHI Fragment

Plasmids pBW35 and pBW36 were individually double digested in separate reactions with XbaI and BamHI restriction enzymes. The desired fragments were isolated and recovered as taught in Example 7B.

In addition, one skilled in the art could isolate the ~1.3 kb XbaI-BamHI fragment from plasmid pBW33 and substitute this fragment for the desired ~1.3 kb XbaI-BamHI fragments from plasmids pBW35 and pBW36. The individual ~1.3 kb XbaI-BamHI fragments from plasmid pBW35 and pBW36 were used in the subsequent ligation to construct plasmids pBW41 and pBW42 respectively.

D. Ligations and Transformations

The ~10 kb XbaI-BamHI vector, the ~1.9 kb EcoRI-XbaI fragment from pL110, and the respective XbaI-BamHI fragments from plasmids pBW35 and pBW36 were individually ligated in substantial accordance with the teaching of Example 4C. The ligation was split and used to transform *E. coli* K12 RV308/pRK248cIts and *E. coli* N5271 host cells in substantial accordance with the teaching of Example 4D except that both host strains were grown at 32° C. rather than 37° C.

Plasmid pRK248cIts can be isolated from E. coli K12 JMB9/pRK248cIts, also known as *E. coli* K12 MCB3604, a strain deposited and made part of the permanent culture collection of the Northern Regional Research Laboratories. Plasmid pRK248cIts can be obtained from the NRRL under the accession number NRRL B-15631. Plasmid pRK248cIts comprises a temperature-sensitive mutant of the lambda pL repressor gene cI; the construction of plasmid pRK248cIts is described in Bernard and Helinski, 1979, *Methods of Enzymology* 68:482, and Bernard et al., 1979, *Gene* 5:59. Plasmid pRK248cIts was isolated and purified in substantial accordance with the procedure of Example 1 and then transformed into *E. coli* K12 RV308 in substantial accordance with the procedure of Example 2B. Because plasmid pRK248cIts comprises a tetracycline resistance-conferring gene, and not the ampicillin resistance-conferring gene, tetracycline resistance was used as the basis for selection of the *E. coli* K12 RV308/pRK248cIts transformants.

However, a variety of plasmids could be used in place of plasmid pRK248cIts for the purposes of this Example. Such plasmids would necessarily comprise a temperature-sensitive lambda pL repressor gene, a selectable marker independent of the ampicillin resistance-conferring gene, and a replicon, such as the replicon from plasmid pACYC184 or an R factor, that is compatible with the replicon of plasmid pBR322. Furthermore, temperature-sensitive control of the novel activating sequence of the present invention could also be obtained by using a host cell, such as *E. coli* N5271 (Lautenberger et al., 1983, *Gene* 23:75), that comprises a chromosomally-integrated, temperature-sensitive cI repressor gene.

The *E. coli* K12 RV308/pRK248cIts transformants and the *E. coli* N5271 host cells were made competent for transformation in substantial accordance with the procedure of Example 2B, except that the host cultures were grown at 32° C. rather than 37° C. In separate transformations, plasmids pBW41 and pBW42 were transformed into *E. coli* K12 RV308/pRK248cIts and *E. coli* N5271 competent cells. Generally, it is believed that an expression plasmid need not carry the cI857 gene to repress the pL promoter, nor is it necessary to resort to heat inactivation to allow induction. As the copy number of the plasmid is increased, the repressor should be outstripped.

The resulting *E. coli* N5271 transformants were then used to isolate their respective runaway replicon-containing plasmids pBW41 and pBW42.

EXAMPLE 18B

Construction of Runaway Replicon Plasmid pBW40

Plasmid pBW40 can be constructed substantially as taught for the construction of plasmids pBW41 and pBW42 except that the ~1.3 kb XbaI-BamHI fragment from pBW33 is substituted for the similar XbaI-BamHI fragment from pBW35 or pBW36. After transformation into *E. coli*, the resulting transformants can then be used to isolate plasmid pBW40 DNA.

EXAMPLE 19

Molecular Weight Determination and Demonstration of Fibrin Dependency

Frozen *E coli* cells containing the modified t-PA from Example 14 were stirred with 25 volumes of a pH 8.0 buffered solution of 7M urea for one hour. After centrifugation, the *E. coli* cell extract was dialyzed against an aqueous buffer (pH 7-8.5) containing a mixed disulfide pair such as cysteine and cystine (Saxena V. P. and Westlaufer, D. B., 1970, *Biochemistry* 9:5012). Finally, the cell extract was dialyzed against the aqueous buffer without the mixed disulfide pair.

This solution was then chromatography on an affinity matrix such as p-amino-benzamidine-agarose. The bound modified t-PA was eluted from the affinity matrix by buffered aqueous solutions of guanidine or arginine. The fractions having t-PA activity were pooled, concentrated, dialyzed and then chromatographed on a molecular sizing column such as Fractogel TSK55S which had been previously calibrated with proteins of known molecular weight so that the molecular weight of the modified t-PA could be determined by this methodolgy (Whitaker, J. R., 1963, *Anal. Chem.* 35:1950).

The purification of modified t-PA from 2g *E. coli* is summarized in the following table:

| Sample | Total Protein | Total t-PA | Fibrin Dependency |
| --- | --- | --- | --- |
| E. coli cell extract | 496 mg | 46.4 | 1.2 |
| PAB-Agarose Pool | 177 | 34.5 | 1.7 |
| Fractogel TSK55 Pool | 107 | 27.3 | 4.1 |

Fibrin dependency is defined as the ratio of plasminogen activator activity measured using D-val-leu-lys-p-nitroanilide as the substrate in the presence and absence of soluble fibrin monomer or CNBr fragments of fibrinogen.

The peak of the modified t-PA activity elutes from the calibrated molecular sizing column at a position corresponding to the correct molecular weight, 39.4kD, for the molecule.

The above data clearly demonstrate that the recombinant modified t-PA expressed in *E. coli* has the correct molecular weight and is fibrin dependent for plasminogen activation.

EXAMPLE 20

Isolation of Plasmid pKC283

Lyophils of *E. coli* K12 BE1201/pKC283 are obtained from the Northern Regional Research Laboratory, Peoria, Ill. 61604, under the accession number NRRL B-15830. The lyophils are decanted into tubes containing 10 ml LB medium (10 g Bacto-tryptone, 5 g Bacto-yeast extract, and 10 g NaCl per liter; pH is adjusted to 7.5) and incubated two hours at 32° C., at which time the cultures are made 50 μg/ml in ampicillin and then incubated at 32° C. overnight. The *E. coli* K12 BE1201/pKC283 cells were cultured at 32° C., because the cells comprise a temperature-sensitive cI repressor gene integrated into the cellular DNA. When cells that comprise a wild-type lambda pL repressor gene or do not comprise a lambda pL promoter are utilized in this plasmid isolation procedure, as described in subsequent Examples herein, the temperature of incubation is 37° C.

A small portion of the overnight culture is placed on LB-agar (LB medium with 15 g/l Bacto-agar) plates containing 50 μg/ml ampicillin in a manner so as to obtain a single colony isolate of *E. coli* K12 BE1201/pKC283. The single colony obtained was inoculated into 10 ml of LB medium containing 50 μg/ml ampicillin and incubated overnight at 32° C. with vigorous shaking. The 10 ml overnight culture was inoculated into 500 ml LB medium and incubated at 32° C. with vigorous shaking until the culture reached stationary phase. The plasmid DNA was isolated in accordance with the teaching of Example 1B. A restriction site and function map of plasmid pKC283 is presented in FIG. 16 of the accompanying drawings.

EXAMPLE 21

Construction of Plasmid pKC283PX

About 10 μl of the plasmid pKC283 DNA prepared in Example 20 were mixed with 20 μl 10×medium-salt restriction buffer (500 mM NaCl; 100 mM Tris-HCl, pH 7.5; 100 mM MgCl$_2$; and 10 mM DTT), 20 μl mg/ml BSA, 5 μl restriction enzyme PvuII (~50 Units), and 145 μl of water, and the resulting reaction was incubated at 37° C. for 2 hours. Restriction enzyme reactions described herein were routinely terminated by phenol and then chloroform extractions, which were followed by precipitation of the DNA, an ethanol wash, and resuspension of the DNA in TE buffer. After terminating the PvuII digestion as described above, the PvuII-digested plasmid pKC283 DNA was precipitated and then resuspended in 5 μl of TE buffer.

About 600 picomoles (pM) of XhoI linkers (5'-CCTCGAGG-3') were kinased in accordance with the teaching of Example 8E and then about 12.5 μl of the kinased XhoI linkers were added to 5 μl of PvuII-digested plasmid pKC283 DNA. Next, 2.5 μl of 10×ligase buffer (300 mM Tris-HCl, pH 7.6; 100 mM MgCl$_2$; and 50 mM DTT), 2.5 μl of 1 mg/ml BSA, 7 μl of 5 mM ATP, 2.5 μl (about 2.5 units as defined by P-L Biochemicals) of T4 DNA ligase, 2.5 μl of 10 mM spermidine, and 3 pl of water were added to the DNA. The resulting ligation reaction was incubated at 4° C. overnight. After the ligation reaction, the reaction mixture was adjusted to have the composition of high-salt buffer (0.1 M NaCl; 0.05M Tris-HCl, pH 7.5; 10.0 mM MgCl$_2$; and 1 mM DTT). About 10 μl (100 units) of restriction enzyme XhoI were added to the mixture, and the resulting reaction was incubated at 37° C. for 2 hours.

The reaction was terminated, and the XhoI-digested DNA was precipitated, resuspended, and ligated as described above, except that no XhoI linkers were added to the ligation mixture. The ligated DNA constituted the desired plasmid pKC283PX.

EXAMPLE 22

Construction of *E. coli* K12 MO(λ+)/pKC283PX

*E. coli* K12 MO(λ+)can be obtained from the Northern Regional Research Laboratories in lyophilized form under the accession number NRRL B-15993. *E. coli* K12 MO(λ+) comprises the wild-type lambda pL cI repressor gene, so that transcription from the hybrid pL-1pp promoter of the present invention does not occur in *E. coli* K12 MO(λ+) cells. The lyophils are reconstituted, single colonies of MO(λ+) are isolated, and a 10 ml overnight culture of the MO(λ+)cells is prepared in substantial accordance with the procedure of Example 20, except that the temperature of incubation is 37° C. and no ampicillin is used in the growth media.

Fifty μl of the overnight culture were used to inoculate 5 ml of LB media which also contained 10 mM MgSO$_4$ and 10 mM MgCl$_2$. The culture was incubated at 37° C. overnight with vigorous shaking. The following morning, the culture was diluted to 200 ml with LB media containing 10 mM MgSO$_4$ and 10 mM MgCl$_2$. The diluted culture was incubated at 37° C. with vigorous shaking until the absorbance at 550 nm A550) was about 0.5, which indicated a cell density of about 1×10$^8$ cells/ml. The culture was cooled for ten minutes in an ice-water bath, and the cells were then collected by centrifugation at 4000 g for 10 minutes at 4° C. The cell pellet was resuspended in 100 ml of cold 10 mM NaCl and then immediately re-pelleted by centrifugation. The cell pellet was resuspended in 100 ml of 30 mM CaCl$_2$ and incubated on ice for 20 minutes.

The cells were again collected by centrifugation and resuspended in 10 ml of 30 mM CaCl$_2$. A one-half ml aliquot of the cells was added to the ligated DNA prepared in Example 21; the DNA had been made 30 mM in CaCl$_2$. The cell-DNA mixture was incubated on ice for one hour, heat-shocked at 42° C. for 90 seconds, and then chilled on ice for about two minutes. The cell-DNA mixture was diluted into 10 ml of LB media in 125 ml flasks and incubated at 37° C. for one hour. One hundred μl aliquots were plated on LB-agar plates containing ampicillin and incubated at 37° C. until colonies appeared.

The colonies were individually cultured, and the plasmid DNA of the individual colonies was examined by restriction enzyme analysis and gel electrophoresis. Plasmid DNA isolation was performed on a smaller scale in accordance with the procedure of Example 20, but the CsCl gradient step was omitted until the desired *E. coli* K12 MO(λ+)/pKC283PX transformants were identified. A restriction site and function map of plasmid pKC283PX is presented in FIG. 17 of the accompanying drawings.

EXAMPLE 23

Construction of *E. coli* K12 MO(λ+)/pKC283-L

Ten μg of plasmid pKC283PX DNA prepared in accordance with the procedure of Example 20 were dissolved in 20 μl of 10X high-salt buffer, 20 μl mg/ml BSA, 5 μl (~50 units) restriction enzyme BglII, 5μl (~50 units) restriction enzyme XhoI, and 150 μl of water, and the resulting reaction was incubated at 37° C. for two hours. The reaction was stopped, and after precipitating the BglII-XhoI-digested DNA, the DNA was resuspended in 5 μl of TE buffer.

A DNA linker with single-stranded DNA ends characteristic of BglII and XhoI restriction enzyme cleavage was synthesized and kinased. The linker was kinased in substantial accordance with the procedure of Example 8E. The DNA linker had the following structure:

```
5'-GATCTATTAACTCAATCTAGAC-3'
   ||||||||||||||||||||
3'-ATAATTGAGTTAGATCTGAGCT-5'
```

The linker and BglII-XhoI-digested plasmid pKC283PX were ligated in substantial accordance with the procedure of Example 21. The ligated DNA constituted the desired plasmid pKC283-L. A restriction site and function map of plasmid pKC283-L is presented in FIG. 18 of the accompanying drawings. The plasmid pKC283-L DNA was used to transform E. coli K12 MO(λ+) and the resulting E. coli K12 MO(λ+)/pKC283-L transformants were identified in substantial accordance with the procedure of Example 22.

EXAMPLE 24

Construction of E. coli K12 MO(λ+)/pKC283-LB

About 10 μg of plasmid pKC283-L DNA, prepared in substantial accordance with the procedures of Example 20, were dissolved in 20 μl 10×high-salt buffer, 20 μl 1 mg/ml BSA, 5 μl (~50 units) restriction enzyme XhoI, and 155 μl of H₂O, and the resulting reaction was incubated at 37° C. for two hours. The XhoI-digested plasmid pKC283-L DNA was then precipitated from the reaction mixture by the addition of three volumes of 95% ethanol and one-tenth volume of 3M sodium acetate, incubation in a dry ice-ethanol bath for five minutes, and centrifugation. The resulting DNA pellet was washed with 70% ethanol, dried, and resuspended in 2 μl 10×nick-translation buffer (0.5M Tris-HCl, pH 7.2; 0.1M M MgSO₄; and 1 mM DTT), 1 μl of a solution 2 mM in each of the deoxynucleotide triphosphates, 15 μl of H₂O, 1 μl (~6 units) of Klenow, and 1 μl of 1 mg/ml BSA. The resulting reaction was incubated at 25° C. for 30 minutes; the reaction was stopped by incubating the solution at 70° C. for five minutes.

BamHI linkers (5'-CGGGATCCCG-3') were kinased and ligated to the XhoI-digested, Klenow-treated plasmid pKC283-L DNA in substantial accordance with the procedure of Example 21. After the ligation reaction, the DNA was digested with about 100 units of BamHI for about 2 hours at 37° C. in high-salt buffer. After the BamHI digestion, the DNA was prepared for ligation in substantial accordance with the procedure of Example 21.

The ~5.9 kb BamHI restriction fragment was circularized by ligation and transformed into E. coli K12 MO(λ+) in substantial accordance with the procedures of Examples 20 and 21. The E. coli K12 MO(λ+)/pKC283-LB transformants were identified, and then plasmid pKC283-LB DNA was prepared in substantial accordance with the procedure of Example 20. A restriction site and function map of plasmid pKC283-LB is presented in FIG. 19 of the accompanying drawings.

EXAMPLE 25

Construction of E. coli K12 MO(λ+)/pL32

About 10 μg of plasmid pKC283PX were digested with restriction enzyme SalI in high-salt buffer, treated with Klenow, and ligated to EcoRI linkers (5'-GAG-GAATTCCTC-3') in substantial accordance with the procedure of Example 24, with the exception of the starting plasmid, restriction enzymes, and linkers used. After digestion with restriction enzyme EcoRI, which results in the excision of ~2.1 kb of DNA, the ~4.0 kb EcoRI restriction fragment was circularized by ligation to yield plasmid pKC283PRS. The ligated DNA was used to transform E. coli K12 MO(λ+) in substantial accordance with the procedure of Example 22. After the E. coli K12 MO(λ+)/pKC283PRS transformants were identified, plasmid pKC283PRS DNA was prepared in substantial accordance with the procedure of Example 20. A restriction site and function map of plasmid pKC283PRS is presented in FIG. 20 of the accompanying drawings.

About 10 μg of plasmid pKC283PRS were digested in 200 μl of high-salt buffer with about 50 units each of restriction enzymes PstI and SphI. After incubating the reaction at 37° C. for about 2 hours, the reaction mixture was electrophoresed on a 0.6% low-gelling-temperature agarose gel for 2-3 hours at ~130V and ~75 mA in Tris-Acetate buffer.

The gel was stained in a dilute solution of ethidium bromide, and the band of DNA constituting the ~0.85 kb PstI-SphI restriction fragment, which was visualized with long-wave UV light, was cut from the gel in a small segment. The volume of the segment was determined by weight and density of the segment, and an equal volume of 10 mM Tris-HCl, pH 7.6, was added to the tube containing the segment. The segment was then melted by incubation at 72° C. About 1 μg of the ~0.85 kb PstI-SphI restriction fragment of plasmid pKC283PRS was obtained in a volume of about 100 μl. In an analogous manner, plasmid pKC283-LB was digested with restriction enzymes PstI and SphI, and the resulting ~3.0 kb restriction fragment was isolated by agarose gel electrophoresis and prepared for ligation.

The ~0.85 kb PstI-SphI restriction fragment of plasmid pKC283PRS was ligated to the ~3.0 kb PstI-SphI restriction fragment of plasmid pKC283-LB in substantial accordance with the procedure of Example 21. The ligated DNA constituted the desired plasmid pL32. A restriction site and function map of plasmid pL32 is presented in FIG. 21 of the accompanying drawings. Plasmid pL32 was transformed into E. coli K12 MO(λ+) cells in substantial accordance with the procedure of Example 22. Plasmid pL32 DNA was prepared from the E. coli K12 MO(λ+)/pL32 transformants in substantial accordance with the procedure of Example 20. Analysis of the plasmid pL32 DNA demonstrated that more than one EcoRI linker attached to the Klenow-treated, SalI ends of plasmid pKC283PX. The presence of more than one EcoRI linker does not affect the utility of plasmid pL32 or derivatives of plasmid pL32 and can be detected by the presence of an XhoI restriction site, which is generated whenever two of the EcoRI linkers are ligated together.

EXAMPLE 26

Construction of E. coli K12 MO(λ+)/pL47

Plasmid pCC101 is disclosed in Example 3 of U.S. Pat. No. 4,745,069, issued May 17, 1988 incorporated herein by reference. A restriction site and function map of plasmid pCC101 is presented in FIG. 28 of the accompanying drawings. To isolate the EK-BGH-encoding DNA, about 10 μg of plasmid pCC101 were digested in 200 μl of high-salt buffer containing about 50 units each of restriction enzymes XbaI and BamHI. The digestion products were separated by agarose gel electrophoresis, and the ~0.6 kb XbaI-BamHI restriction fragment which encodes EK-BGH was isolated and prepared for ligation in substantial accordance with the procedure of Example 25.

Plasmid pL32 was also digested with restriction enzymes XbaI and BamHI, and the ~3.9 kb restriction fragment was isolated and prepared for ligation. The ~3.9 kb XbaI-BamHI restriction fragment of plasmid pL32 was ligated to the ~0.6 kb XbaI-BamHI restriction fragment of plasmid pCC101 in substantial accordance with the procedure of Example 21 to yield plasmid pL47. A restriction site and function map of plasmid pL47 is presented in FIG. 22 of the accompanying drawings. Plasmid pL47 was transformed into $E.$ $coli$ K12 MO($\lambda$+) in substantial accordance with the procedure of Example 22, and the $E.$ $coli$ K12 MO($\lambda$+)/pL47 transformants were identified. Plasmid pL47 DNA was prepared from the transformants in substantial accordance with the procedures of Example 20.

EXAMPLE 27

Construction of $E.$ $coli$ K12 MO($\lambda$+)/pL84

About 10 μg of plasmid pL32 were digested with about 50 units of restriction enzyme BamHI in 200 μl of high-salt buffer at 37° C. for about two hours. The BamHI-digested plasmid pL32 DNA was precipitated, treated with Klenow, and ligated to SalI linkers (5'-CGTCGACG-3') in substantial accordance with the procedure of Example 24. After the SalI linkers were ligated, about 100 units of restriction enzyme SalI and about 50 units of restriction enzyme XbaI were added to the ligation mixture, which was adjusted to have the composition of high-salt buffer, and the resulting reaction was incubated at 37° C. for two hours. The reaction products were separated by agarose gel electrophoresis, and the ~3.9 kb SalI-XbaI restriction fragment was isolated and prepared for ligation in substantial accordance with the procedure of Example 25.

About 10 μg of plasmid pCC101 were digested with about 50 units each of restriction enzymes SalI and XbaI in 200 μl of high-salt buffer at 37° C. for 2 hours. The reaction products were separated by agarose gel electrophoresis, and the ~1.6 kb SalI-XbaI restriction fragment which encodes EK-BGH and the transcription terminator of the $E.$ $coli$ lpp gene was isolated and prepared for ligation in substantial accordance with the procedure of Example 25.

The ~3.9 kb SalI-XbaI restriction fragment derived from plasmid pL32 was ligated to the ~1.6 kb SalI-XbaI restriction fragment of plasmid pCC101 in substantial accordance with the procedure of Example 21. The ligated DNA constituted the desired plasmid pL84. A restriction site and function map of pL84 is presented in FIG. 23 of the accompanying drawings. The ligated DNA was used to transform $E.$ $coli$ K12 MO($\lambda$+) cells in substantial accordance with the procedure of Example 22. Plasmid pL84 DNA was prepared from the $E.$ $coli$ K12 MO($\lambda$+)/pL84 transformants in substantial accordance with the procedure of Example 20.

EXAMPLE 28

Construction of $E.$ $coli$ K12 MO($\lambda$+)/pL95

About 10 μg of plasmid pL84 were digested with about 50 units restriction enzyme NdeI in about 200 μl of high-salt buffer for two hours at 37° C. The NdeI-digested DNA was then precipitated and treated with Klenow in substantial accordance with the procedure of Example 24. The NdeI-digested, Klenow-treated plasmid pL84 DNA was then ligated to KpnI linkers (5'-GGGTACCC-3') in substantial accordance with the procedure of Example 21. After the linker ligation, the DNA was precipitated and the resulting DNA pellet was resuspended in 20 μl of 10×low-salt buffer (0.1M Tris-HCl, pH 7.6; 0.1M MgCl$_2$; and 10 mM DTT), 20 μl of 1 mg/ml BSA, 5 μl (about 50 units) restriction enzyme KpnI, and 155 μl of H$_2$O. The resulting reaction was incubated at 37° C. for two hours.

After the KpnI digestion, the DNA was loaded onto a low-melting-temperature agarose gel, and the ~3.8 kb restriction fragment was isolated and recircularized by ligation in substantial accordance with the procedure of Example 25. The ligated DNA constituted plasmid pL95, which was used to transform $E.$ $coli$ K12 MO($\lambda$+) in substantial accordance with the procedure of Example 22. A restriction site and function map of plasmid pL95 is presented in FIG. 24 of the accompanying drawings.

EXAMPLE 29

Construction of $E.$ $coli$ K12 RV308/pPR12ΔR1

Plasmid pPR12 comprises the temperature-sensitive pL repressor gene cI857 and the plasmid pBR322 tetracycline resistance-conferring gene. Plasmid pPR12 is disclosed and claimed in U.S. Pat. No. 4,436,815, issued Mar. 13, 1984. A restriction site and function map of plasmid pPR12 is presented in FIG. 25 of the accompanying drawings.

About 10 μg of plasmid pPR12 were digested with about 50 units of restriction enzyme EcoRI in 200 μl of high-salt buffer at 37° C. for two hours. The EcoRI-digested plasmid pPR12 DNA was precipitated and treated with Klenow in substantial accordance with the procedure of Example 24. After the Klenow reaction, the EcoRI-digested, Klenow-treated plasmid pPR12 DNA was recircularized by ligation in substantial accordance with the procedure of Example 21. The ligated DNA, which constituted the desired plasmid pPR12ΔR1, was used to transform $E.$ $coli$ K12 RV308 in substantial accordance with the procedure of Example 22 except that selection was based on tetracycline (5 ug/ml) resistance, not ampicillin resistance. $E.$ $coli$ K12 RV308 is available from the NRRL under the accession number NRRL B-15624. After the $E.$ $coli$ K12 RV308/pPR12ΔR1 transformants were identified, plasmid pPR12ΔRI DNA was prepared transformants in substantial accordance with the procedure of Example 20.

About 10 μg of plasmid pPR12ΔR1 was digested with about 50 units of restriction enzyme AvaI in 200 μl of medium-salt buffer at 37° C. for 2 hours. The AvaI-digested plasmid pPR12ΔR1 DNA was precipitated and treated with Klenow in substantial accordance with the procedure of Example 24. After the Klenow reaction, the AvaI-digested, Klenow-treated plasmid pPR12ΔR1 DNA was ligated to EcoRI linkers (5'-GAGGAATTCCTC-3') in substantial accordance with the procedure of Example 21. After the linker ligation, the DNA was precipitated and then resuspended in about 200 μl of high-salt buffer containing about 50 units of restriction enzyme EcoRI. The resulting reaction was incubated at 37° C. for about 2 hours. After the EcoRI digestion, the reaction mixture was loaded onto an agarose gel, and the ~5.1 kb EcoRI restriction fragment was purified in substantial accordance with the procedure of Example 25. The ~5.1 kb EcoR1 restriction fragment was recirculated by ligation in substantial accordance with the procedure of Example 21. The ligated DNA constituted the desired plasmid pPR12AR1. The plasmid pPR12AR1 DNA was transformed into *E. coli* K12 RV308 in substantial accordance with the procedure of Example 22 except that selection was based on tetracycline resistance, not ampicillin resistance. After identifying the *E. coli* K12 RV308/pPR12AR1 transformants, plasmid pPR12AR1 DNA was prepared in substantial accordance with the procedure of Example 20. A restriction site and function map of plasmid pPR12AR1 is presented in FIG. 26 of the accompanying drawings.

EXAMPLE 30

Construction of *E. coli* K12 RV308/pL110

About 10 μg of plasmid pPR12AR1 DNA were suspended in about 200 ml of high-salt buffer containing about 50 units each of restriction enzymes PstI and EcoRI, and the digestion reaction was incubated at 37° C. for about 2 hours. The reaction mixture was then loaded onto an agarose gel, and the ~2.9 kb PstI-EcoRI restriction fragment of plasmid pPR12AR1 was isolated and prepared for ligation in substantial accordance with the procedure of Example 25.

About 10 μg of plasmid pL47 were digested with restriction enzymes PstI and BamHI in 200 μl of high-salt buffer at 37° C. for two hours. The PstI-BamHI digested DNA was loaded onto an agarose gel, and the ~2.7 kb PstI-BamHI restriction fragment that comprised the origin of replication and a portion of the ampicillin resistance-conferring gene was isolated and prepared for ligation in substantial accordance with the procedure of Example 25. In a separate reaction, about 10 ug of plasmid pL47 DNA were digested with restriction enzymes EcoRI and BamHI in 200 μl of high-salt buffer at 37° C. for two hours, and the ~1.03 kb EcoRI-BamHI restriction fragment that comprised the novel transcriptional and translational activating sequence and the EK-BGH-encoding DNA was isolated and prepared for ligation in substantial accordance with the procedure of Example 25. The ~2 ug of the ~1.03 kb EcoRI-BamHI restriction fragment obtained were used in the construction of plasmid pL110.

The ~2.7 kb PstI-BamHI and ~1.03 kb EcoRI-BamHI restriction fragments of plasmid pL47 were ligated to the ~2.9 kb PstI-EcoRI restriction fragment of plasmid pPR12AR1 to construct plasmid pL110, and the ligated DNA was used to transform *E. coli* K12 RV308 in substantial accordance with the procedure of Examples 21 and 22, except that tetracycline resistance, not ampicillin resistance, was used as the basis for selecting transformants.

Two PstI restriction enzyme recognition sites are present in the EK-BGH coding region that are not depicted in the restriction site and function maps presented in the accompanying drawings. A restriction site and function map of plasmid pL110 is presented in FIG. 27 of the accompanying drawings.

EXAMPLE 31

Construction of Plasmid pBW46

A. Construction of Plasmid pBW44

Plasmid pBW44 was constructed in a three-piece ligation reaction using restriction fragments from pBW33 and pL195. Two fragments from pBW33 were isolated and which, upon religation, collectively reconstitute the plasmid except for the coding region of the carboxy-terminus of the t-PA gene. The third fragment, isolated from plasmid pL195, contains the coding region of the carboxy-terminus of the t-PA gene minus much of the 3'-non-coding sequence.

The ~3.9 kb BamHI-ClaI and ~2.7 kb ClaI-SstI restriction fragments from plasmid pBW33 were isolated in substantial accordance with the teaching of Example 4A substituting the appropriate restriction enzymes and buffers where necessary. In accordance, the ~0.3 kb SstI-BamHI fragment from pL195 was isolated, mixed with the two pBW33 restriction fragments, and ligated in accordance with the teaching of Example 4C except that the final concentration of ATP was increased to 500 μM. The ligation product was used to transform *E. coli* MM294 cells in substantial accordance with the teaching of Example 1B except tetracycline at a concentration of 15 μg/ml was used and the transformants were incubated at 32° C.

B. Construction of Plasmid mp8BW45

This vector was constructed from single-stranded pM8BW27 following the site specific mutagenesis procedure of Adelman et al., 1983, except that the S1 treatment was performed for 10 minutes at 20° C. and the following synthetic oligodeoxyribonucleotide primer was substituted:

5'-GGATTTGCTGGGAAGTCCTGT-
GAAATATCCACC-3'

This primer was used to change nucleotide number 437 in $CYS_{83}$ from guanine to cytosine, thereby changing $CYS_{83}$ to $SER_{83}$.

The resulting mutagenesis mix was used to infect *E. coli* JM109 cells (commercially available from BRL) as taught in Example 5C. Desired mutants were identified by hybridization with the synthetic oligodeoxyribonucleotide 5'-GGGAAGTCCTGTGAAA-3'. Briefly, the filters were prepared as described by Hanahan and Meselson, 1980, *Gene* 10:63-67 except that Millipore 82 mm HATF filters were substituted and these filters were steamed instead of autoclaved.

Plaque lifts were performed by placing filters on top of prechilled (4° C. for 60 minutes) overlay plates for 1-2 minutes. Next, the filters were transferred to Whatman 3MM filter paper saturated with the following solutions: 0.1M NaOH, 1.5M NaCl for 5 minutes and 0.5M Tris pH 7.5, 3M NaCl for an additional 5 minutes. The filters were air dried and then baked for 2 hours at 80° C. The filters were prehybridized at 45° C. for 90 minutes in a solution of 6×SSC (0.9 M NaCl and 0.09M Na Citrate), 0.1% NaPPi, 0.1% SDS, 10×Denhardt's (0.2% Ficoll, 0.2% polyvinylpyrolidone, 0.2% BSA) and 1 μg/ml *E. coli* DNA.

Next, the filters were hybridized in 0.23 pmols/ml of hybridization buffer (6×SSC, 0.1% NaPPi, 10×Denhardt's) and the radioactive probe (specific activity=0.72 μCi/pmol) at 45° C. for 2 hours. The filters were rinsed with 6×SSC according to the following schedule:

| No. of washes | Temperature (°C.) | Time (minutes) |
| --- | --- | --- |
| 1 | 25 | 2 |
| 2 | 25 | 20 |
| 1 | 37 | 10 |

| No. of washes | Temperature (°C.) | Time (minutes) |
|---|---|---|
| 2 | 50 | 3 |

The filters were exposed to X-ray film at −70° C. for one hour with an intensifying screen. The DNA from the plaques which hybridized to the probe was extracted and identified by dideoxy sequencing.

C. Final Construction

Plasmid pBW46 was constructed in a three-piece ligation using restriction fragments from pBW44 and mp8BW45. A fragment from mp8BW45 containing the section of t-PA encoding sequence wherein the cysteine substitution was made, was ligated to two fragments from plasmid pBW44 thereby forming a new gene sequence coding for a kringle-less form of t-PA that does not contain any free sulfhydryl residues.

The ∼4440 bp EcoRI-ClaI and ∼1950 ClaI-NdeI restriction fragments from pBW44 were isolated in substantial accordance with the teaching of Example 4A substituting the appropriate restriction enzymes and buffers where necessary. In accordance, the ∼562 bp NdeI-EcoRI fragment from mp8BW45 was isolated, mixed with the above fragments and ligated in substantial accordance with the teaching of Example 31. The ligation product was used to transform E. coli MM294 cells and the RF DNA was isolated in substantial accordance with the alkaline miniscreen procedure of Birnboim and Doly, 1979. E. coli K12 RV308 was transformed with this plasmid DNA for expression of the SER$_{83}$mt-PA3.

EXAMPLE 32

Construction of Plasmid mp18BW50

A. Construction of mp18BW47

The construction of this vector was performed substantially as taught in Example 5 with the conditions modified accordingly for the use of different restriction enzymes. Thus, the ∼7250 bp HindIII-SstI restriction fragment from mp18 (BRL) was ligated to the ∼1440 HindIII-SstI fragment from pTPA103. This ligated material was used to transfect E. coli JM109 cells (BRL) and the transfectants were cultured and single-stranded DNA was prepared for use as a starting material in the following mutagenesis example.

B. Site Specific Mutagenesis

Single-stranded mp18BW47 was mutagenized in substantial accordance with the teaching of Example 6 except that the Klenow reaction was done at room temperature for 60 minutes, followed by 4 hours at 37° C., and then overnight at 4° C. In addition, the S1 treatment was for 20 minutes at 20° C. The synthetic oligodeoxyribonucleotide primer used was

5'-GGATTTGCTGGGAAGTCCTGT-
GAAATAGGAAACAGTGACTGCTAC-3' to delete amino acid residues 87 through 175 of native t-PA.

The resulting mutagenesis mix was used to transfect E. coli JM109 cells and desired mutants were identified by hybridization with a synthetic oligodeoxyribonucleotide probe (5'-GTCCTGTGAAATAGGAA-3') according to the teaching of Example 31. These positives were further confirmed by M13 sequencing using the M13 sequencing primer (5'-GTGCCCCGAAG-GATTTG-3') and the recombinant clones were designated mp18BW50.

EXAMPLE 33

Construction of Plasmid pL219

Figure 29:
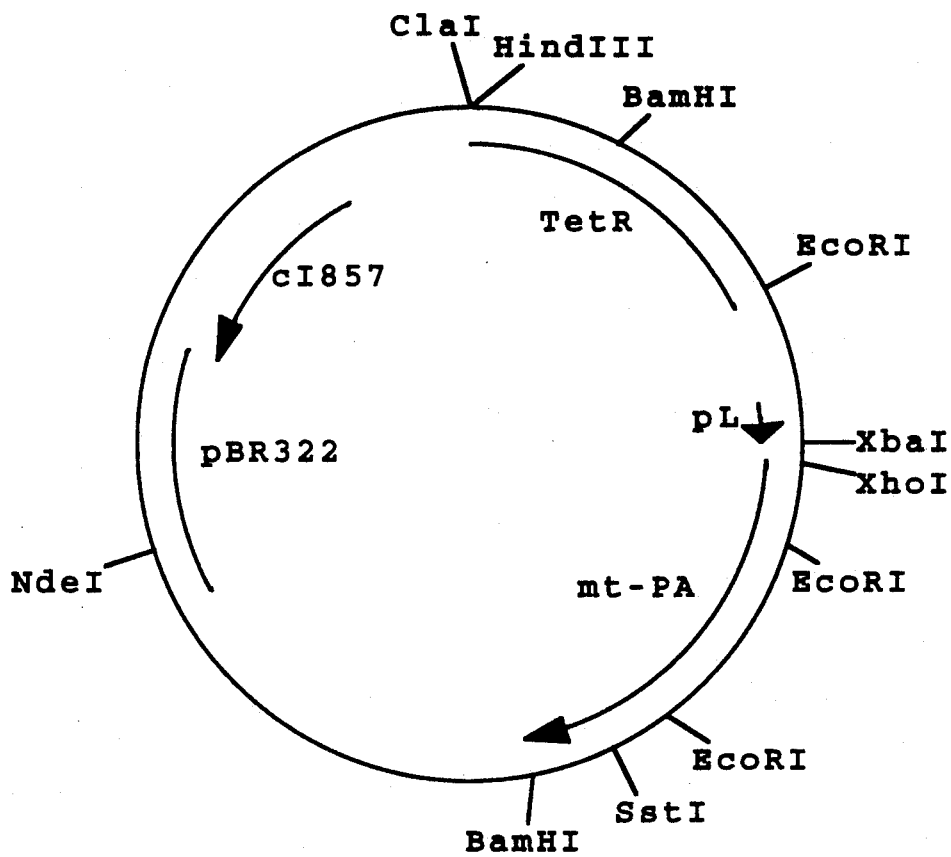
FIG. 29 is a restriction site and function map of plasmid pL219.

Plasmid pL219 is a prokaryotic expression vector which contains a modified t-PA encoding gene sequence designated mt-PA4, wherein the first kringle (K1) domain, spanning amino acid residues 87 through 175, has been deleted and the C$_{83}$ residue has been changed to SER$_{83}$. To construct this derivative, restriction fragments from three previously constructed vectors were isolated and joined by T4 ligase in a multiple ligation reaction. Accordingly, the ∼1.0 kb BglII-SstI fragment comprising the 5' amino-terminus of the mt-PA4 gene, including the K1 domain deletion, was isolated from the replicative form of mp18BW50. The ∼50 bp XbaI-XhoII restriction fragment containing the two cistron construction was isolated from plasmid pBW33. These two fragments were mixed with the ∼6.1 kb SstI-XbaI fragment from pBW46, ligated and used to transform E. coli RV308. A restriction site and function map of plasmid pL219 is presented in FIG. 29 of the accompanying drawings. Plasmid pL219 DNA was prepared from the E. coli RV308/pL219 transformants in substantial accordance with the procedure of Example 31.

EXAMPLE 34

Construction of mt-PA3-containing Mammalian Expression Vectors

A. Construction of Intermediate Plasmid pTPA308

Vector pTPA301, constructed in Example 8C, was digested with BglII and SstI restriction enzymes to delete ∼1.2 kb of the native t-PA gene encoding sequence. Approximately 5.3 μg of plasmid pTPA301 DNA were dissolved in 2 μl 10×BglII reaction buffer, 2 μl (∼16 units) restriction enzyme BglII, and 16 μl H$_2$O, and the reaction was placed at 37° C. for two hours. The reaction mixture was then made 0.15M LiCl, and after adding 2.5 volumes of ethanol and chilling in a dry ice-ethanol bath, the DNA was pelleted by centrifugation.

The DNA pellet was dissolved in 2 μl 10×SstI buffer, 2 μl (∼20 units) restriction enzyme SstI, and 16 μl H$_2$O, and the reaction was placed at 37° C. for two hours. After the SstI digestion, the reaction mixture was loaded onto a 0.8% agarose gel, and the fragments were separated by electrophoresis. After inspecting the gel stained with ethidium bromide under ultraviolet light, the band containing the desired ∼5 kb BglII-SstI fragment was excised from the gel and extracted as described in Example 4A. The pellet was resuspended in 10 μl of dH$_2$O and constituted ∼4.3 μg of the desired ∼5 kb BglII-SstI restriction fragment of plasmid pTPA301.

Next, vector pBW46, constructed in Example 31, was digested with XhoII and SstI restriction enzymes to obtain ∼700 bp of the modified t-PA sequence. Thus, ∼2 μg of plasmid pBW46 DNA were digested with XhoII and SstI restriction enzymes as taught above, except that XhoII is substituted for BglII. The desired ∼700 bp XhoII-SstI restriction fragment was isolated on a 0.8% agarose gel, excised and extracted as described previously. The pellet was resuspended in 5 μl of dH$_2$O.

The ~5 kb BglII-SstI fragment from pTPA301 was ligated to the ~700 bp XhoII-SstI fragment of pBW46 according to the teaching of Example 8C. The ligated DNA constitutes the intermediate plasmid pTPA308. Plasmid pTPA308 was transformed into *E. coli* K12 SF8 (NRRL B-15835). Plasmid DNA was obtained from the *E. coli* K12 SF8/pTPA308 transformants in substantial accordance with the procedure for plasmid pTPA102 DNA isolation.

B. Construction of Plasmid pTPA309

Figure 30:
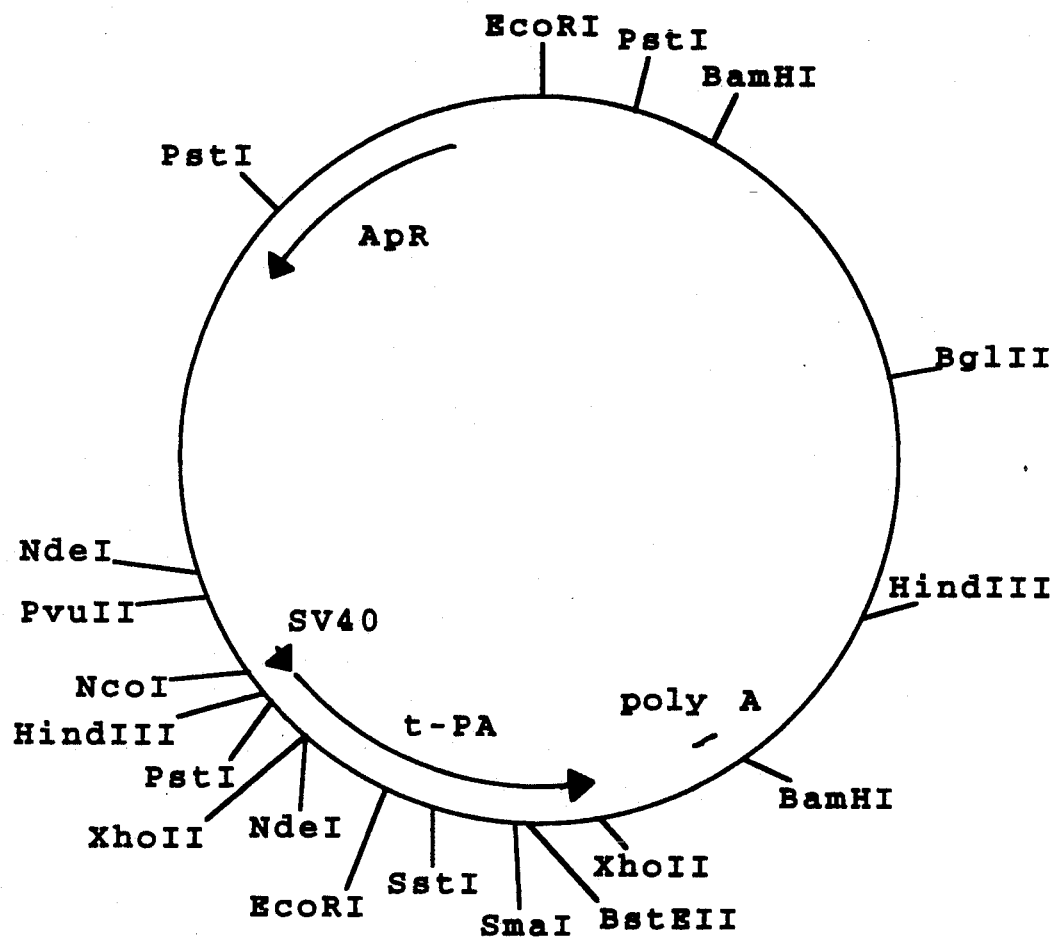
FIG. 30 is a restriction site and function map of plasmid pTPA309.

For the construction of pTPA309, ~100 μl (2 μg) of plasmid pTPA308 was digested with BamHI restriction enzyme and phosphatased using 1 μl (~1 unit Boehringer Mannheim) calf intestinal alkaline phosphatase in substantial accordance with the teaching of Example 8F. The linearized pTPA308 vector fragment was ligated to the ~1.9 kb BamHI fragment containing the dhfr gene (isolated in Example 8E) according to the teaching of Example 8F. A restriction site and function map of plasmid pTPA309 is presented in FIG. 30 of the accompanying drawings.

Plasmid pTPA309 was transformed into *E. coli* K12 SF8 in substantial accordance with the teaching of Example 2B and the resulting *E. coli* K12 SF8/pTPA309 transformants were identified by their ampicillin-resistant phenotype and by restriction enzyme analysis of their plasmid DNA. Plasmid pTPA309 was isolated from the transformants and used to transfect CHO K1dhfr-) cells according to the teaching of Example 10. The resultant colonies were isolated and characterized. The desired pTPA309 plasmids expressed a modified t-PA similar to that expressed by plasmid BW32 except that the amino acid residue at position 83 is serine, not cysteine.

EXAMPLE 35

Construction of mt-PA4-containing Mammalian Expression Vectors

A. Construction of Intermediate Plasmid pTPA310

Vector pTPA301 was prepared as taught in Example 34A to isolate the ~5 kb BglII-SstI restriction fragment. Next, a restriction fragment containing the mutagenized gene from Example 32, wherein the Kringle 1 domain was deleted and the $CYS_{83}$ to $SER_{83}$ modification was performed, was isolated for ligation to the ~5 kb BglII-SstI restriction fragment of pTPA301. Vector pL217 was used to isolate the ~1 kb BglII-SstI restriction fragment containing the modified t-PA gene. However, the equivalent fragment is contained in plasmid pL219, described in Example 33. Thus, this vector can be digested with BglII and SstI restriction enzymes as taught in Example 34 to isolate the desired ~1 kb BglII-SstI fragment. After ligating the ~1 kb BglII-SstI fragment to the ~5 kb BglII-SstI fragment of pTPA301, the resultant ligated DNA was used to transform *E. coli* K12 SF8. *E. coli* K12 SF8/pTPA310 transformants were identified by their ampicillin-resistant phenotype and by enzyme analysis of their plasmid DNA. Plasmid DNA was isolated from the transformants and used in the construction of pTPA311, below.

B. Construction of Plasmid pTPA311

Figure 31:
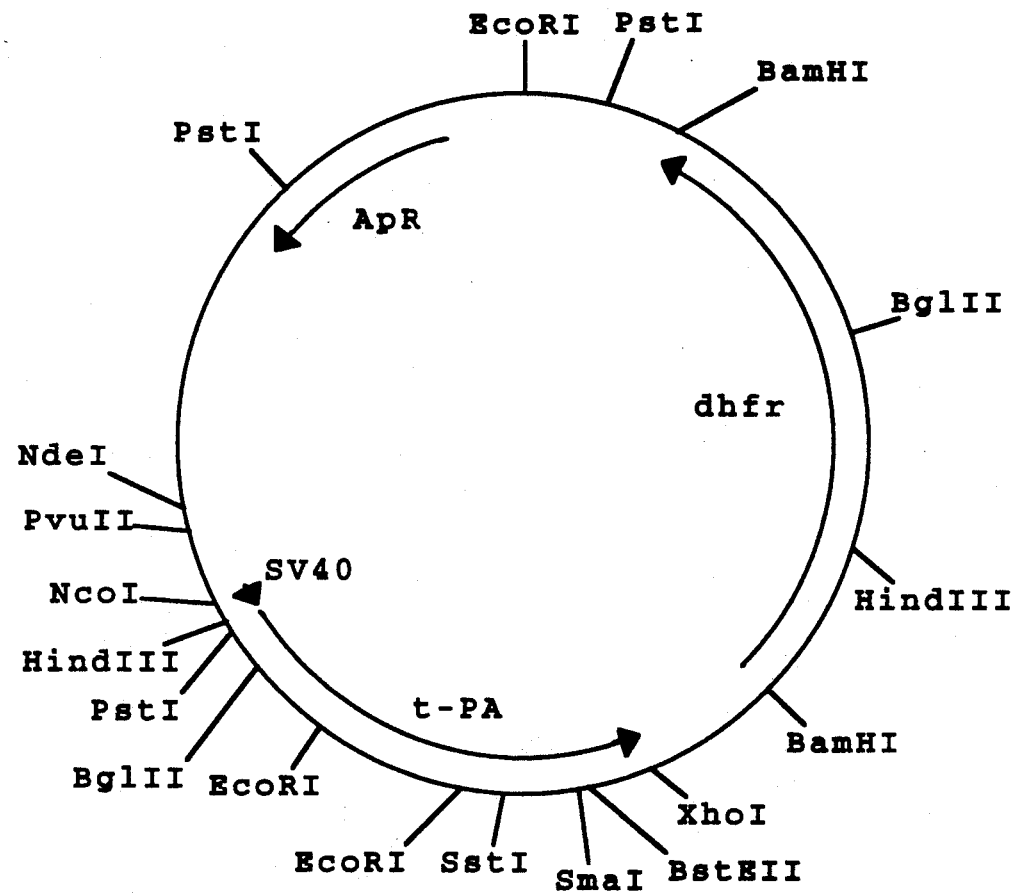
FIG. 31 is a restriction site and function map of plasmid pTPA311.

Vector pTPA310 was digested with BamHI restriction enzyme and phosphatased with calf intestinal alkaline phosphatase as described in Example 34B. The ~2 kb BamHI fragment containing the dhfr gene (isolated in Example 8E) was ligated to the BamHI-digested pTPA310 linear DNA. The ligated DNA was used to transform *E. coli* K12 SF8 cells from which plasmid pTPA311 DNA was isolated. A restriction site and function map of plasmid pTPA311 is presented in FIG. 31 of the accompanying drawings.

Plasmid pTPA311 was used to transfect CHO K1 (dhfr-) cells and the resultant colonies were isolated and characterized. One of the transformants was designated clone 4. The desired pTPA311 plasmids expressed a modified t-PA with a $CYS_{83}$ to $SER_{83}$ switch and a deleted K1 domain.

EXAMPLE 36

Purification of mt-PA2 and mt-PA3

The mutant proteins mt-PA2 and mt-PA3 were purified from conditioned media of CHO clones transfected with the plasmids described in Examples 10 and 34, respectively. Gene amplification through the exposure of the clones to increasing concentrations of methotrexate was accomplished as described in Example 10 and resulted in conditioned media usually containing between 50 and 200 units of activity by standard fibrin plate assays. From 1–40 liters of conditioned media were initially purified on a 2.5×50 cm column packed with benzamidine coupled to agarose (Pierce). The column was equilibrated with 0.05M Tris, 0.15M NaCl, 0.02% $NaN_3$, and 0.01% Tween 80, pH 7.5 for mt-PA 2. The column was washed with 10 column volumes equilibration buffer with NaCl increased to 0.5M NaCl and desorption was accomplished with the washing buffer with 1.5M $NH_4SCN$ plus 0.5M arginine added. The fractions from the benzamidine column containing PA activity were pooled and dialyzed against 0.05M Tris 0.15M NaCl, 0.01% Tween 80, and 0.2% $NaN_3$, pH 7.5. The next step in the purification of mt-PA2 was affinity chromatography on a lysine Sepharose column (1.5×30 cm) equilibrated with the same Tris buffer of the pooled fractions from the benzamidine step. Unabsorbed material from the lysine column containing PA activity was pooled and concentrated through dialysis against PEG 2,000. The lysine step served to remove endogenous full-length t-PA synthesized in small quantities by normal as well as transfected CHO cells. The second kringle structure of the full-length t-PA secreted by CHO cells binds to immobilized lysine whereas mt-PA2 containing no kringle structures fails to absorb to immobilized lysine.

After concentration of active fractions from the lysine column to approximately 10 ml, the concentrated material was applied either to a Sephacryl 200 or Sephadex G100 column (2.5×100 cm) equilibrated with 0.05M Tris, 0.25M NaCl, 0.025M EDTA, 0.01% Tween 80, and 0.02% $NaN_3$, pH 7.5. These active fractions from Sephacryl or G100 columns were usually concentrated five-fold through dialysis against PEG 20,000 and stored at −80°. The purification efforts for mt-PA2 resulted in different preparations with different specific activities and different dependence on fibrin for activation of plasminogen. The final gel filtration steps routinely resulted in the emergence of at least two peaks of activity, one with $M_r$ of approximately 100 kd and one in the $M_r$ range of 30–45 kd. Each time complete purification was attempted, only very limited quantities of material suitable for testing (i.e. specific activity of approximately 500,000 iu/mg) were available for functional studies.

The following purification scheme for mt-PA3 was adopted. The starting material was serum free conditioned media containing traysylol ~100 KI/ml from CHO cell clones. A 2.5×50 benzamidine agarose column was equilibrated with 0.5M Tris, 0.15M NaCl, 0.02% NaN$_3$, 0.01% Tween 80, Trasylol 100 KI units/ml, pH 7.5. Conditioned media from 10–50 liters containing Trasylol 100 KI units/ml were passed over the benzamidine agarose column at the flow rate of approximately 15–20 ml/hour. The column was washed with equilibration buffer with the NaCl concentration increased to 0.5M and desorption was accomplished with 1.5M NH$_4$SCN plus 0.5M arginine added to the washing buffer. The fractions containing plasminogen activator activity were pooled and concentrated through dialysis against PEG 20,000. The approximately 10–15 fold concentrated material was further purified through isoelectric precipitation, through extensive dialysis against 0.02M acetate, 15M NaCl, 0.02% NaN$_3$, 0.01% Tween 80, and Trasylol 100 KI units/ml, pH 4.5. Approximately 90% of the protein including the endogenous CHO cell native t-PA was found in the precipitate and mt-PA3 (pI: pH 7.5) was recovered at 100% in the supernatant. After concentration of the supernatant from the isoelectric precipitation to a total volume of approximately 10 ml through dialysis against PEG 20,000, this material was applied to a Sephadex G100 column equilibrated with 0.05M acetate, 0.15M NaCl, 0.01% Tween 80, 0.02% NaN$_3$, and Trasylol 100 KI units/ml, pH 4.5. An additional step of fibrin-celite chromatography essentially according to the procedure of Husain et al., 1981, *Proc. Natl. Acad. Sci., USA* 78:4265–4269 was occasionally interposed between the isoelectric precipitation and the G100 gel filtration steps. A 2.5×30 fibrin celite column equilibrated with 0.05M PO$_4$, 0.02% NaN$_3$, 0.01% Tween 80, and 100 KI units/ml Trasylol, pH 7.5, was loaded with the supernatant from the isoelectric precipitation step. The column was first washed with 0.2M NaCl-0.2M arginine. The second wash utilized a 0.5M NaCl, 0.5M arginine, and 0.2M NH$_4$SCN, and the third wash 0.5M NaCl, 0.5M arginine, and 1.5M NH$_4$SCN. Significant quantities of PA activity eluted with each change of buffer but the most tightly bound material desorbed with 1.5M NH$_4$SCN possessed highest specific activity after the subsequent Sephadex G100 gel filtration step.

Characterization of mt-PA2 or mt-PA3

For mt-PA2, SDS PAGE, "fibrin autography" and Western blots readily identified a discrete band, M$_r$41.5 kd when run under nonreducing conditions. Under reducing conditions 2 bands were regularly observed. mt-PA3 purified by the 3 or the 4 step procedure was nearly homogenous by SDS PAGE with a faint band of approximately 12 kd appearing as a constant contaminant. SDS PAGE under reducing conditions revealed the molecule to be approximately 60–70% single chain with the remaining 30–40% in the two-chain form.

Functional Characterization mt-PA2 was assayed for fibrin dependent plasminogen activation according to Ranby and Wallén, 1981 and the result is expressed as the ratio of the rate constants (k$_1$) for plasminogen activation in the presence and absence of fibrin monomer. The rate constants were calculated according to Ranby and Wallén. The "fibrin dependence ratios" for mt-PA2 range from 1.1 (no fibrin dependence) to 5.5 (equivalent to the WHO standard reference t-PA). The fibrin dependence ratios for mt-PA3 have ranged between 3.5 and 11.5 with "large-scale preparations" averaging about 7–8.

The specific activities for mt-PA2 have ranged from 50–500,000 iu/mg; for mt-PA3 purified by the 3 step procedure, the specific activity is approximately 350,000 iu/mg and for material purified by the 4 step procedure, 5–600,000 iu/mg. One international unit is derived from the issued WHO standard reference t-PA preparation.

EXAMPLE 37

Purification and Characterization of mt-PA4

A. Purification of mt-PA4 from Conditioned Medium

Clone 4 mt-PA conditioned medium was centrifuged to remove cell debris. Tween 80 was added to the clear supernatant to give a final concentration of 0.01%. Trasylol was included in the conditioned medium at a level of ~100 KI units/ml to ensure that the modified t-PA would remain in a one-chain form. The conditioned medium was applied to an affinity column of benzamidine agarose equilibrated at 5° with 0.05M Tris, 0.25M NaCl, 0.01% Tween 80, and 100 KI units/ml Trasylol pH 8.0. After application of all the conditioned medium, the column was eluted with equilibration buffer. The mt-PA4 activity was eluted from the affinity column with 1.6M KSCN and 0.5M arginine in the starting buffer. The pooled active fractions were then dialyzed against 0.05M Tris, 0.25M NaCl, 0.01% Tween 80 and 100 KI units/ml Trasylol, pH 8.0 to remove the KSCN and arginine.

Further purification was accomplished by chromatography on a second affinity column, lysine Sepharose. The dialyzed, pooled fractions from the previous column were applied to the lysine Sepharose column equilibrated with the dialysis buffer. After application of the sample, the column was eluted with the equilibration buffer. The mt-PA4 activity was eluted from the affinity column with 0.2M epsilon-amino caproic acid in the equilibration buffer. The pooled active fractions from the column were concentrated by ultrafiltration on a YM10 membrane to a volume suitable for chromatography on a Sephadex G100 column. The concentrated sample was adjusted to pH 4.5.

Final purification of the mt-PA4 was accomplished by gel filtration on a column of Sephadex G100 equilibrated at 5° with 0.02M sodium acetate, and 0.25M NaCl, pH 4.5. The concentrated sample from the previous column was applied to the Sephadex G100 column, and the column was then eluted with the equilibration buffer. The active fractions were pooled.

B. Identification of Number of Chains in mt-PA4 mt-PA4, freshly prepared by the above procedure exists in a one chain form as evidenced by SDS PAGE. The samples were applied to a gel having a 9–18% polyacrylamide gradient. Samples of mt-PA4 were applied to the gel under non-reducing and reducing conditions. The one chain mt-PA4 exhibits the same apparent molecular weight, approximately 62 kD, in the SDS PAGE system run under reducing and non-reducing conditions.

C. Fibrin Dependency of mt-PA4

The fibrin dependent activation of plasminogen by mt-PA4 was demonstrated in the same manner as described in Example 12. In the evaluation of mt-PA4, however, rate constants were not calculated, but rather the rates of plasminogen activation by mt-PA4 were compared in the presence of CNBr fragments of fibrinogen(FP) and fibrin monomer(FM) to the rate in the absence of these modifiers. The results obtained were:

|  | Fibrin Dependency | |
| --- | --- | --- |
|  | FP | FM |
| native t-PA (Melanoma cells) | 14.0 | 6.1 |
| mt-PA4 (one chain) | 16.5 | 6.3 |
| mt-PA4 (two chain) | 17.0 | 7.2 |

These experiments demonstrate that mt-PA4 purified from conditioned medium from CHO cells expressing and secreting this modified t-PA has preserved its fibrin dependence.

EXAMPLE 38

Plasminogen Activator Inhibitor Studies

Reagents and Assay

Fibrinogen is bovine fibrinogen from Miles Laboratories (Elkhart, Indiana) rendered plasminogen free through lysine sepharose chromatography and freed of trace impurities of an additional unknown protease through affinity chromatography on immobilized Trasylol.

Thrombin is human alpha-thrombin, specific activity approximately 3,000 NIH units/mg and containing no plasminogen or plasmin impurities.

Reference standard t-PA was purified to apparent homogeneity ($\sim$500,000 iu/mg) from conditioned media from Bowes melanoma cell cultures. On SDS PAGE this preparation consisted of approximately equal parts of single and two-chain material.

Semipurified plasminogen activator inhibitor (PAI) was prepared from human platelets. Two units of freshly separated human platelet concentrates were purchased from a blood bank. The platelets were separated from the plasma in the bag through three-fold washing in ACD solution, pH 6.4, and finally suspended to half original volume in a modified Tyrode's buffer containing no calcium but Na$_3$ citrate to 0.38%. To activate platelets and produce the release reaction, human fibrinogen (Kabi Grade L) was added to 1 mg/ml. The release reaction was produced first by adding adenosine diphosphate (Sigma) to 10 mM, reconstituting with calcium to 25 mM and finally thrombin to 10 units/ml. The platelet-fibrin pellet was removed by centrifugation and the supernatant used for additional purification. Residual fibrinogen and non-clottable fibrinogen/fibrin degradation products were removed through ammonium sulfate precipitation at 50% saturation resulting in no loss of PI activity. Trace contaminants in the preparation of alpha-two plasmin inhibitor, alpha-two macroglobulin, alpha-one antitrypsin and C1 esterase inhibitor were eliminated through acid treatment of the releasate for 20 minutes (pH 3, room temperature). The inhibitor was "activated" through the addition of quanidine HCl to 4M, incubation at room temperature for two hours followed by extensive dialysis against the standard buffer used throughout the assay: 0.03M Tris, 0.15M NaCl, and 0.01% Tween 80, pH 7.5.

Reagents were admixed in the fibrin coated microtiter wells (as taught in Example 11) as follows: Ten $\mu$l of purified preparations of reference t-PA, mt-PA2, mt-PA3 or mt-PA4, all of similar specific activity ($\sim$500,000 iu/mg), all diluted to 0.5 iu/10 $\mu$l; 0, 5 or 10 $\mu$l semipurified "activated" PAI, 20 $\mu$l of plasminogen (final concentration 0.15 $\mu$M), 90 $\mu$l of 3 mM S2251 in standard buffer and standard buffer to a total volume of 200 $\mu$l. The plates were incubated at 37° C. and A$_{405nm}$ readings done in a plate reader every hour for 6–8 hours. Percent inhibition of t-PA activity was calculated from $\Delta A_{405nm}/2$ h in the wells containing 5 or 10 $\mu$l of PAI divided by $\Delta A_{405nm}/2$ h for wells containing 0 PAI.

Results

Table[I outlines the percent inhibition by 5 and 10 $\mu$l PAI of t-PA, mt-PA2, mt-PA3 or mt-PA4. It is evident that mt-PA2 and mt-PA3 lacking the kringle structures are inhibited far less than t-PA by PAI whereas mt-PA4 containing kringle two is inhibited at least as much as reference t-PA.

TABLE II

Inhibition of purified native t-PA, mt-PA2, mt-PA3 and mt-PA4 by plasminogen activator inhibitor (PAI, 5 and 10 $\mu$l)

|  | Percent Inhibition | |
| --- | --- | --- |
|  | 5 $\mu$l | 10 $\mu$l PAI |
| native t-PA | 66 | 89 |
| mt-PA2, Expt 1* | ND | 19 |
| mt-PA2, Expt 2* | ND | 9 |
| mt-PA3 | 8.9 | 46.4 |
| mt-PA4 | 87.9 | 91.7 |

*Experiment 1 and 2 were done with two different preparations of mt-PA2
ND = not done

We claim:

1. A deoxyribonucleic acid (DNA) molecule encoding a modified tissue plasminogen activator characterized in that the deoxyribonucleic acid comprises the following sequence, wherein the coding strand is:

5'-R-TCT TAC CAA GTG ATC TGC

AGA GAT GAA AAA ACG CAG

ATG ATA TAC CAG CAA CAT

CAG TCA TGG CTG CGC CCT

GTG CTC AGA AGC AAC CGG

GTG GAA TAT TGC TGG TGC

ACC AGT GGC AGG GCA CAG

TGC CAC TCA GTG CCT GTC

AAA AGT TGC AGC GAG CCA

AGG TGT TTC AAC GGG GGC

ACC TGC CAG CAG GCC CTG

TAC TTC TCA GAT TTC GTG

TGC CAG TGC CCC GAA GGA

TTT GCT GGG AAG TXC TGT

GAA ATA TCC ACC TGC GGC

CTG AGA CAG TAC AGC AAG

CCT CAG TTT CGC ATC AAA

GGA GGG CTC TTC GCC GAC

-continued

ATC GCC TCC CAC CCC TGG

CAG GCT GCC ATC TTT GCC

AAG CAC AGG AGG TCG CCC

GGA GAG CGG TTC CTG TGC

GGG GGC ATA CTC ATC AGC

TCC TGC TGG ATT CTC TCT

GCC GCC CAC TGC TTC CAG

GAG AGG TTT CCG CCC CAC

CAC CTG ACG GTG ATC TTG

GGC AGA ACA TAC CGG GTG

GTC CCT GGC GAG GAG GAG

540
    CAG AAA TTT GAA GTC GAA

AAA TAC ATT GTC CAT AAG

GAA TTC GAT GAT GAC ACT

TAC GAC AAT GAC ATT GCG

CTG CTG CAG CTG AAA TCG

GAT TCG TCC CGC TGT GCC

CAG GAG AGC AGC GTG GTC

CGC ACT GTG TGC CTT CCC

CCG GCG GAC CTG CAG CTG

CCG GAC TGG ACG GAG TGT

720
    GAG CTC TCC GGC TAC GGC

AAG CAT GAG GCC TTG TCT

CCT TTC TAT TCG GAG CGG

CTG AAG GAG GCT CAT GTC

AGA CTG TAC CCA TCC AGC

CGC TGC ACA TCA CAA CAT

TTA CTT AAC AGA ACA GTC

ACC GAC AAC ATG CTG TGT

GCT GGA GAC ACT CGG AGC

GGC GGG CCC CAG GCA AAC

TTG CAC GAC GCC TGC CAG

GGC GAT CGG GGA GGC CCC

CTG GTG TGT CTG AAC GAT

GGC CGC ATG ACT TTG GTG

GGC ATC ATC AGC TGG GGC

CTG GGC TGT GGA CAG AAG

GAT GTC CCG GGT GTG TAC

ACC AAG GTT ACC AAC TAC

CTA GAC IGG ATT CGT GAC

AAC ATG CGA CCG TGA-3' wherein
  A is deoxyadenyl,
  G is deoxyguanyl,
  C is deoxycytidyl,
  T is thymidyl,
  R is 5'-ATG GAT GCA ATG AAG AGA GGG CTC TGC TGT
    GTG CTG CTG CTG TGT GGA GCA GTC TTC GTT
    TCG CCC AGC CAG GAA ATC CAT GCC CGA TTC
    AGA AGA GGA GCC AGA-3' or 5'-ATG GGA-3' and
X is G or C.

2. The DNA molecule of claim 1 wherein X is G.

3. The DNA molecule of claim 1 wherein X is C.

4. A deoxyribonucleic acid molecule encoding a modified t-PA comprising the following sequence, wherein the coding strand is:

```
                10              20              30              40
5'-R—TCT TAC CAA GTG ATC TGC AGA GAT GAA AAA ACG CAG ATG ATA TAC CAG 50              60              70              80              90
    CAA CAT CAG TCA TGG CTG CGC CCT GTG CTC AGA AGC AAC CGG GTG GAA 100             110             120             130             140
    TAT TGC TGG TGC AAC AGT GGC AGG GCA CAG TGC CAC TCA GTG CCT GTC 150             160             170             180             190
    AAA AGT TGC AGC GAG CCA AGG TGT TTC AAC GGG GGC ACC TGC CAG CAG 200             210             220             230             240
    GCC CTG TAC TTC TCA GAT TTC GTG TGC CAG TGC CCC GAA GGA TTT GCT 250             260             270             280
    GGG AAG TCC TGT GAA ATA GGA AAC AGT GAC TGC TAC TTT GGG AAT GGG 290             300             310             320             330
    TCA GCC TAC CGT GGC ACG CAC AGC CTC ACC GAG TCG GGT GCC TCC TGC 340             350             360             370             380
    CTC CCG TGG AAT TCC ATG ATC CTG ATA GGC AAG GTT TAC ACA GCA CAG 390             400             410             420             430
    AAC CCC AGT GCC CAG GCA CTG GGC CTG GGC AAA CAT AAT TAC TGC CGG
```

```
                440         450         460         470         480
            AAT CCT GAT GGG GAT GCC AAG CCC TGG TGC CAC GTG CTG AAG AAC CGC 490         500         510         520
            AGG CTG ACG TGG GAG TAC TGT GAT GTG CCC TCC TGC TCC ACC TGC GGC 530         540         550         560         570
            CTG AGA CAG TAC AGC CAG CCT CAG TTT CGC ATC AAA GGA GGG CTC TTC 580         590         600         610         620
            GCC GAC ATC GCC TCC CAC CCC TGG CAG GCT GCC ATC TTT GCC AAG CAC 630         640         650         660         670
            AGG AGG TCG CCC GGA GAG CGG TTC CTG TGC GGG GGC ATA CTC ATC AGC 680         690         700         710         720
            TCC TGC TGG ATT CTC TCT GCC GCC CAC TGC TTC CAG GAG AGG TTT CCG 730         740         750         760
            CCC CAC CAC CTG ACG GTG ATC TTG GGC AGA ACA TAC CGG GTG GTC CCT 770         780         790         800         810
            GGC GAG GAG GAG CAG AAA TTT GAA GTC GAA AAA TAC ATT GTC CAT AAG 820         830         840         850         860
            GAA TTC GAT GAT GAC ACT TAC GAC AAT GAC ATT GCG CTG CTG CAG CTG 870         880         890         900         910
            AAA TCG GAT TCG TCC CGC TGT GCC CAG GAG AGC AGC GTG GTC CGC ACT 920         930         940         950         960
            GTG TGC CTT CCC CCG GCG GAC CTG CAG CTG CCG GAC TGG ACG GAG TGT 970         980         990         1000
            GAG CTC TCC GGC TAC GGC AAG CAT GAG GCC TTG TCT CCT TTC TAT TCG 1010        1020        1030        1040        1050
            GAG CGG CTG AAG GAG GCT CAT GTC AGA CTG TAC CCA TCC AGC GCC TGC 1060        1070        1080        1090        1100
            ACA TCA CAA CAT TTA CTT AAC AGA ACA GTC ACC GAC AAC ATG CTG TGT 1110        1120        1130        1140        1150
            GCT GGA GAC ACT CGG AGC GGC GGG CCC CAG GCA AAC TTG CAC GAC GCC 1160        1170        1180        1190        1200
            TGC CAG GGC GAT TCG GGA GGC CCC CTG GTG TGT CTG AAC GAT GGC CGC 1210        1220        1230        1240
            ATG ACT TTG GTG GGC ATC ATC AGC TGG GGC CTG GGC TGT GGA CAG AAG 1250        1260        1270        1280        1290
            GAT GTC CCG GGT GTG TAC ACA AAG GTT ACC AAC TAC CTA GAC TGG ATT 1300        1310
            CGT GAC AAC ATG CGA CCG TGA-3'
``` wherein

A is deoxyadenyl, G is deoxyguanyl, C is deoxycytidyl and T is thymidyl;

R is

```
5'-ATG GAT GCA ATG AAG AGA GGG CTC TGC TGT
    GTG CTG CTG CTG TGT GGA GCA GTC TTC GTT
```

-continued
```
    TCG CCC AGC CAG GAA ATC CAT GCC CGA TTC
    AGA AGA GGA GCC AGA-3'
``` or 5'-ATG GGA-3'.

5. A DNA molecule which encodes a modified tissue plasminogen activator having the amino acid sequence:

```
R—SER TYR GLN VAL ILE CYS ARG ASP GLU LYS THR GLN MET ILE
                     5                              10

TYR GLN GLN HIS GLN SER TRP LEU ARG PRO VAL LEU ARG SER
    15                      20                      25

ASN ARG VAL GLU TYR CYS TRP CYS ASN SER GLY ARG ALA GLN
                30                      35                  40

CYS HIS SER VAL PRO VAL LYS SER CYS SER GLU PRO ARG CYS
                45                      50                  55
```

```
               PHE ASN GLY GLY THR CYS GLN GLN ALA LEU TYR PHE SER ASP
                              60              65              70

PHE VAL CYS GLN CYS PRO GLU GLY PHE ALA GLY LYS Z  CYS
                          75                  80

GLU ILE SER THR CYS GLY LEU ARG GLN TYR SER GLN PRO GLN
               85                  90                  95

PHE ARG ILE LYS GLY GLY LEU PHE ALA ASP ILE ALA SER HIS
                   100             105                 110

PRO TRP GLN ALA ALA ILE PHE ALA LYS HIS ARG ARG SER PRO
                       115             120                 125

GLY GLU ARG PHE LEU CYS GLY GLY ILE LEU ILE SER SER CYS
                           130             135                 140

TRP ILE LEU SER ALA ALA HIS CYS PHE GLN GLU ARG PHE PRO
                               145                 150

PRO HIS HIS LEU THR VAL ILE LEU GLY ARG THR TYR ARG VAL
               155             160                 165

VAL PRO GLY GLU GLU GLU GLN LYS PHE GLU VAL GLU LYS TYR
                   170                 175                 180

ILE VAL HIS LYS GLU PHE ASP ASP ASP THR TYR ASP ASN ASP
                           185                 190                 195

ILE ALA LEU LEU GLN LEU LYS SER ASP SER SER ARG CYS ALA
                               200                 205             210

GLN GLU SER SER VAL VAL ARG THR VAL CYS LEU PRO PRO ALA
                               215                 220

ASP LEU GLN LEU PRO ASP TRP THR GLU CYS GLU LEU SER GLY
               225                 230                 235

TYR GLY LYS HIS GLU ALA LEU SER PRO PHE TYR SER GLU ARG
                   240                 245                 250

LEU LYS GLU ALA HIS VAL ARG LEU TYR PRO SER SER ARG CYS
                       255                 260                 265

THR SER GLN HIS LEU LEU ASN ARG THR VAL THR ASP ASN MET
                           270                 275                 280

LEU CYS ALA GLY ASP THR ARG SER GLY GLY PRO GLN ALA ASN
                               285                 290

LEU HIS ASP ALA CYS GLN GLY ASP SER GLY GLY PRO LEU VAL
               295                 300                 305

CYS LEU ASN ASP GLY ARG MET THR LEU VAL GLY ILE ILE SER
                   310                 315                 320

TRP GLY LEU GLY CYS GLY GLN LYS ASP VAL PRO GLY VAL TYR
                       325                 330                 335

THR LYS VAL THR ASN TYR LEU ASP TRP ILE ARG ASP ASN MET
                           340                 345                 350

ARG PRO
``` wherein
R is

```
                              -30
               MET ASP ALA MET LYS ARG GLY LEU

-25
               CYS CYS VAL LEU LEU LEU LYS GLY ALA

-15                 -10
               VAL PHE VAL SER PRO SER GLN GLU ILE

-5
               HIS ALA ARG PHE ARG ARG GLY ALA ARG
``` or MET GLY and
$Z_{83}$ is CYS or SER.

6. A recombinant DNA expression vector comprising the DNA molecule of claim 2.

7. The expression vector of claim 6 that is plasmid pBW28.

8. The expression vector of claim 3 that is plasmid pBW32.

9. The expression vector of claim 6 that is plasmid pBW33.

10. The expression vector of claim 6 that is plasmid pBW35.

11. The expression vector of claim 6 that is plasmid pBW36.

12. The expression vector of claim 6 that is plasmid pBW40.

13. The expression vector of claim 6 that is plasmid pBW41.

14. The expression vector of claim 6 that is plasmid pBW42.

15. A recombinant DNA expression vector comprising the DNA molecule of claim 3.

16. A recombinant DNA expression vector comprising the DNA molecule of claim 4.

17. A transformed host cell comprising a recombinant DNA expression vector of claim 6.

18. The transformed host cell of claim 17 that is a prokaryote.

19. The transformed host cell of claim 18 that is *E. coli*.

20. The transformed host cell of claim 19 that is *E. coli* K12 RV308/pBW33.

21. The transformed host cell of claim 19 that is *E. coli* K12 RV308/pBW35.

22. The transformed host cell of claim 19 that is *E. coli* K12 RV308/pBW36.

23. The transformed host cell of claim 17 that is a eukaryote.

24. The transformed host cell of claim 23 that is CHO K1/pBW32.

25. A transformed host cell comprising a recombinant DNA expression vector of claim 15.

26. The transformed host cell of claim 25 that is *E. coli*.

27. The transformed host cell of claim 27 that is a eukaryote.

28. A transformed host cell comprising a recombinant DNA expression vector of claim 16.

29. The transformed host cell of claim 28 that is *E. coli*.

30. The transformed host cell of claim 28 that is a eukaryote.

* * * * *